(12) United States Patent
Tau et al.

(10) Patent No.: US 6,946,535 B2
(45) Date of Patent: Sep. 20, 2005

(54) FILMS COMPRISING ISOTACTIC PROPYLENE COPOLYMERS

(75) Inventors: Li-Min Tau, Lake Jackson, TX (US); Pak-Wing S. Chum, Lake Jackson, TX (US); Seema Karande, Pearland, TX (US); Clive Bosnyak, Missouri City, TX (US)

(73) Assignee: Dow Global Technologies Inc., Midland, MI (US)

( * ) Notice: Subject to any disclaimer, the term of this patent is extended or adjusted under 35 U.S.C. 154(b) by 4 days.

(21) Appl. No.: 10/967,849

(22) Filed: Oct. 18, 2004

(65) Prior Publication Data

US 2005/0054800 A1 Mar. 10, 2005

Related U.S. Application Data

(63) Continuation of application No. 10/289,168, filed on Nov. 5, 2002
(60) Provisional application No. 60/338,881, filed on Nov. 6, 2001.

(51) Int. Cl.[7] .............................................. C08F 10/00
(52) U.S. Cl. .................... 526/348.1; 526/351; 526/352; 525/55
(58) Field of Search ............................. 526/348.1, 352, 526/351; 525/55

(56) References Cited

U.S. PATENT DOCUMENTS

| 3,520,861 A | 7/1970 | Thomson et al. ........... 260/88.1 |
| 4,076,698 A | 2/1978 | Anderson et al. ......... 526/348.6 |

(Continued)

FOREIGN PATENT DOCUMENTS

| EP | 0 277 003 A1 | 8/1988 | ............. C08F/4/64 |
| EP | 0229476 | * 10/1991 | |

(Continued)

OTHER PUBLICATIONS

Alt, Helmut G., et al., *Chem. Rev. 2000*, 100, 1205–1221.

(Continued)

*Primary Examiner*—William K. Cheung
(74) *Attorney, Agent, or Firm*—Whyte Hirschboeck Dudek SC

(57) ABSTRACT

Films with excellent machine direction (MD) tear properties comprise at least one layer made from a polymer comprising:

(A) at least 50 weight percent (wt %) propylene; and
(B) at least 5 wt % ethylene and/or one or more unsaturated comonomers.

Representative of component (B) unsaturated comonomers are the $C_{4-20}$ α-olefins, $C_{4-20}$ dienes, styrenic compounds, and the like. Preferably, the film has at least one of a (i) haze value of less than about 10, (ii) 45 degree gloss of greater than about 65, and (iii) dart value of greater than about 100 g/mil. In one preferred embodiment, the layer comprises a compolymer characterized as having at least one of the following properties: (i) $^{13}C$ NMR peaks corresponding to a regio-error at about 14.6 and about 15.7 ppm, the peaks of about equal intensity, (ii) a B-value greater than about 1.4 when the comonomer content, i.e., the units derived from ethylene and/or the unsaturated comonomer(s), of the copolymer is at least about 3 wt %, (iii) a skewness index, $S_{ix}$, greater than about −1.20, (iv) a DSC curve with a $T_{me}$ that remains essentially the same and a $T_{max}$ that decreases as the amount of comonomer, i.e., the units derived from ethylene and/or the unsaturated comonomer(s), in the copolymer is increased, and (v) an X-ray diffraction pattern that reports more gamma-form crystals than a comparable copolymer prepared with a Ziegler-Natta (Z-N) catalyst.

20 Claims, 34 Drawing Sheets

U.S. PATENT DOCUMENTS

| | | |
|---|---|---|
| 4,542,199 A | 9/1985 | Kaminsky et al. ............ 526/160 |
| 4,543,399 A | 9/1985 | Jenkins, III et al. .......... 526/70 |
| 4,544,762 A | 10/1985 | Kaminsky et al. ............ 556/179 |
| 4,588,790 A | 5/1986 | Jenkins, III et al. .......... 526/70 |
| 4,599,392 A | 7/1986 | McKinney et al. ........ 526/318.6 |
| 4,874,880 A | 10/1989 | Miya et al. .................... 556/53 |
| 4,960,878 A | 10/1990 | Crapo et al. ................. 556/179 |
| 4,988,781 A | 1/1991 | McKinney et al. ............ 526/68 |
| 5,015,749 A | 5/1991 | Schmidt et al. .............. 556/179 |
| 5,028,670 A | 7/1991 | Chinh et al. ................... 526/73 |
| 5,032,562 A | 7/1991 | Lo et al. ...................... 502/111 |
| 5,041,583 A | 8/1991 | Sangokoya ................. 556/179 |
| 5,041,584 A | 8/1991 | Crapo et al. ................. 556/179 |
| 5,041,585 A | 8/1991 | Deavenport et al. ........ 556/179 |
| 5,044,438 A | 9/1991 | Young ......................... 166/250 |
| 5,057,475 A | 10/1991 | Canich et al. ................ 502/104 |
| 5,064,802 A | 11/1991 | Stevens et al. ............... 502/155 |
| 5,093,415 A | 3/1992 | Brady, III et al. ............. 525/53 |
| 5,096,867 A | 3/1992 | Canich ........................ 502/103 |
| 5,106,804 A | 4/1992 | Bailly et al. ................. 502/108 |
| 5,132,380 A | 7/1992 | Stevens et al. .............. 526/126 |
| 5,134,209 A | 7/1992 | Job et al. ..................... 526/141 |
| 5,153,157 A | 10/1992 | Hlatky et al. ................ 502/117 |
| 5,198,401 A | 3/1993 | Turner et al. ................ 502/155 |
| 5,218,071 A | 6/1993 | Tsutsui et al. ............... 526/348 |
| 5,272,236 A | 12/1993 | Lai et al. .................. 526/348.5 |
| 5,278,272 A | 1/1994 | Lai et al. .................. 526/348.5 |
| 5,296,433 A | 3/1994 | Siedle et al. ................. 502/117 |
| 5,324,800 A | 6/1994 | Welborn, Jr. et al. ........ 526/160 |
| 5,350,723 A | 9/1994 | Neithamer et al. .......... 502/104 |
| 5,352,749 A | 10/1994 | DeChellis et al. ............. 526/68 |
| 5,384,373 A | 1/1995 | McKinney et al. .......... 526/212 |
| 5,405,922 A | 4/1995 | DeChellis et al. ............. 526/68 |
| 5,408,017 A | 4/1995 | Turner et al. ................ 526/134 |
| 5,427,991 A | 6/1995 | Turner ......................... 502/103 |
| 5,436,304 A | 7/1995 | Griffin et al. .................. 526/68 |
| 5,453,471 A | 9/1995 | Bernier et al. ................. 526/68 |
| 5,461,123 A | 10/1995 | Song et al. .................... 526/74 |
| 5,462,999 A | 10/1995 | Griffin et al. .................. 526/68 |
| 5,473,028 A | 12/1995 | Nowlin et al. ............... 526/114 |
| 5,504,049 A | 4/1996 | Crowther et al. ............ 502/117 |
| 5,504,172 A | 4/1996 | Imuta et al. ................. 526/351 |
| 5,541,270 A | 7/1996 | Chinh et al. ................... 526/68 |
| 5,556,238 A | 9/1996 | Chinh ......................... 406/136 |
| 5,556,928 A | 9/1996 | Devore et al. ............... 526/127 |
| 5,599,761 A | 2/1997 | Turner ......................... 502/152 |
| 5,608,019 A | 3/1997 | Cheruvu et al. ............. 526/129 |
| 5,616,661 A | 4/1997 | Eisinger et al. ................ 526/88 |
| 5,616,664 A | 4/1997 | Timmers et al. ............ 526/127 |
| 5,621,127 A | 4/1997 | Langhauser et al. ......... 556/11 |
| 5,625,087 A | 4/1997 | Devore et al. ............... 556/468 |
| 5,637,660 A | 6/1997 | Nagy et al. .................. 526/160 |
| 5,685,128 A | 11/1997 | Chum et al. ................... 53/441 |
| 5,703,187 A | 12/1997 | Timmers ..................... 526/282 |
| 5,703,257 A | 12/1997 | Rosen et al. .................... 556/7 |
| 5,710,224 A | 1/1998 | Alt et al. ..................... 526/160 |
| 5,721,185 A | 2/1998 | LaPointe et al. ............ 502/117 |
| 5,728,855 A | 3/1998 | Smith et al. ................. 556/179 |
| 5,731,253 A | 3/1998 | Sangokoya ................. 502/102 |
| 5,767,208 A | 6/1998 | Turner et al. ................ 526/160 |
| 5,874,505 A | 2/1999 | Saito et al. .................. 525/240 |
| 5,883,188 A | 3/1999 | Hwang et al. ................ 525/71 |
| 5,883,204 A | 3/1999 | Spencer et al. .............. 526/134 |
| 5,907,021 A | 5/1999 | Turner et al. ................ 526/160 |
| 5,919,983 A | 7/1999 | Rosen et al. .................... 568/3 |
| 5,962,714 A | 10/1999 | McCullough et al. ......... 556/11 |
| 5,965,677 A | 10/1999 | Stephan et al. .............. 526/129 |
| 5,965,756 A | 10/1999 | McAdon et al. ............. 556/11 |
| 5,972,822 A | 10/1999 | Timmers et al. ............ 502/103 |
| 5,977,251 A | 11/1999 | Kao et al. ..................... 525/53 |
| 5,998,039 A | 12/1999 | Tanizaki et al. ............. 428/516 |
| 6,013,819 A | 1/2000 | Stevens et al. ................ 556/11 |
| 6,015,868 A | 1/2000 | Nickias et al. ............... 526/127 |
| 6,034,021 A | 3/2000 | Wilson et al. ............... 502/103 |
| 6,034,240 A | 3/2000 | La Pointe ..................... 546/24 |
| 6,043,363 A | 3/2000 | LaPointe et al. ............ 544/225 |
| 6,074,977 A | 6/2000 | Rosen et al. ................ 502/103 |
| 6,103,657 A | 8/2000 | Murray ....................... 502/155 |
| 6,150,297 A | 11/2000 | Campbell, Jr. et al. ...... 502/152 |
| 6,207,756 B1 | 3/2001 | Datta et al. .................. 525/191 |
| 6,245,856 B1 | 6/2001 | Kaufman et al. ............ 525/240 |
| 6,268,438 B1 | 7/2001 | Ellul et al. ................... 525/240 |
| 6,268,444 B1 | 7/2001 | Klosin et al. ................ 526/127 |
| 6,288,171 B2 | 9/2001 | Finerman et al. ............ 525/192 |
| 6,303,719 B1 | 10/2001 | Murray et al. ............... 526/161 |
| 6,326,433 B1 | 12/2001 | Wang et al. ................. 525/191 |
| 6,342,565 B1 | 1/2002 | Cheng et al. ................ 525/191 |
| 6,444,302 B1 | 9/2002 | Srinivas et al. ........... 428/315.5 |
| 6,500,563 B1 | 12/2002 | Datta et al. .................. 428/521 |
| 6,515,155 B1 | 2/2003 | Klosin et al. .................. 556/11 |
| 6,525,157 B2 | 2/2003 | Cozewith et al. ............ 526/348 |
| 6,635,715 B1 | 10/2003 | Datta et al. .................. 525/240 |
| 6,642,316 B1 | 11/2003 | Datta et al. .................. 525/240 |
| 6,747,114 B2 | 6/2004 | Karandinos et al. ...... 526/348.2 |
| 6,750,284 B1 | 6/2004 | Dharmarajan et al. ....... 524/515 |
| 2002/0062011 A1 | 5/2002 | Campbell, Jr. et al. ........ 534/15 |
| 2002/0137845 A1 | 9/2002 | Boussie et al. .............. 525/170 |
| 2002/0142912 A1 | 10/2002 | Boussie et al. .............. 502/152 |
| 2002/0147288 A1 | 10/2002 | Boussie et al. .............. 526/160 |
| 2002/0156279 A1 | 10/2002 | Boussie et al. ................ 546/13 |
| 2002/0165329 A1 | 11/2002 | Klosin et al. ................ 526/126 |
| 2002/0173419 A1 | 11/2002 | Boussie et al. .............. 502/117 |
| 2002/0177711 A1 | 11/2002 | LaPointe et al. .............. 546/13 |
| 2003/0004286 A1 | 1/2003 | Klosin et al. ................ 526/126 |
| 2003/0130430 A1 | 7/2003 | Cozewith et al. ............ 525/240 |
| 2004/0116609 A1 | 6/2004 | Datta et al. .................. 525/240 |

FOREIGN PATENT DOCUMENTS

| | | | |
|---|---|---|---|
| EP | 0 468 537 A1 | 1/1992 | ............ C08F/10/00 |
| EP | 0 468 651 A1 | 1/1992 | ............ C08F/4/74 |
| EP | 0 514 828 A1 | 11/1992 | ............ C07F/7/28 |
| EP | 0 515 203 A2 | 11/1992 | ............ C08L/67/04 |
| EP | 0 515 203 A3 | 11/1992 | ............ C08L/67/04 |
| EP | 0 593 083 A1 | 4/1994 | ............ C08F/2/34 |
| EP | 0 628 343 A1 | 12/1994 | ............ B01J/3/02 |
| EP | 0 659 773 A1 | 6/1995 | ............ C08F/10/00 |
| EP | 0 663 422 A2 | 7/1995 | ............ C08L/23/06 |
| EP | 0 676 421 A1 | 10/1995 | ............ C08F/10/02 |
| EP | 0 683 176 A1 | 11/1995 | ............ C08F/6/00 |
| EP | 0 692 500 B1 | 1/1996 | ........ C08F/210/00 |
| EP | 0 697 420 A1 | 2/1996 | ............ C08F/10/06 |
| EP | 0 699 213 B1 | 3/1996 | ............ C08F/2/34 |
| EP | 0 716 121 A1 | 6/1996 | ............ C08L/23/10 |
| EP | 0 721 798 A2 | 7/1996 | ............ B01J/8/44 |
| EP | 0 728 150 B1 | 8/1996 | ............ C08F/2/34 |
| EP | 0 728 151 B1 | 8/1996 | ............ C08F/2/34 |
| EP | 0 728 771 A1 | 8/1996 | ............ C08F/10/00 |
| EP | 0 728 772 A1 | 8/1996 | ............ C08F/10/00 |
| EP | 0 735 058 A1 | 10/1996 | ............ C08F/10/00 |
| EP | 0 748 846 A2 | 12/1996 | ............ C08L/67/04 |
| EP | 0 721 798 A3 | 1/1997 | ............ B01J/8/44 |
| EP | 0 748 846 A3 | 2/1997 | ............ C08L/67/04 |
| EP | 0 780 404 A2 | 6/1997 | ............ C08F/10/02 |
| EP | 0 780 404 A3 | 12/1997 | ............ C08F/10/02 |
| EP | 0 949 278 A2 | 10/1999 | ............ C08F/10/00 |
| EP | 0 949 279 A2 | 10/1999 | ............ C08F/10/00 |
| EP | 0 949 278 A3 | 9/2000 | ............ C08F/10/00 |
| EP | 0 949 279 A3 | 9/2000 | ............ C08F/10/00 |
| EP | 1 063 244 A2 | 12/2000 | ......... C08F/210/18 |
| WO | 88/05792 A1 | 8/1988 | ............ C08F/4/64 |
| WO | 88/05793 A1 | 8/1988 | ............ C08F/4/64 |

| | | | | |
|---|---|---|---|---|
| WO | 90/01521 A1 | 2/1990 | ............ | C08L/67/04 |
| WO | 90/07526 A1 | 7/1990 | ............ | C08F/10/00 |
| WO | 93/11171 A1 | 6/1993 | ............ | C08F/10/00 |
| WO | 93/18106 | 9/1993 | .......... | C09J/123/16 |
| WO | 93/19104 A1 | 9/1993 | ............ | C08F/10/00 |
| WO | 93/21238 A2 | 10/1993 | ............ | C08F/10/00 |
| WO | 93/21238 A3 | 10/1993 | ............ | C08F/10/00 |
| WO | 93/21242 A1 | 10/1993 | ......... | C08F/210/16 |
| WO | 93/25590 A1 | 12/1993 | ............ | C08F/10/00 |
| WO | 94/00500 A1 | 1/1994 | ............ | C08F/10/00 |
| WO | 94/03506 A1 | 2/1994 | ............. | C08F/4/64 |
| WO | 94/25495 A1 | 11/1994 | ............. | C08F/2/34 |
| WO | 94/25497 A1 | 11/1994 | ............ | C08F/10/00 |
| WO | 94/26793 A1 | 11/1994 | ............ | C08F/10/00 |
| WO | 94/28032 A1 | 12/1994 | ............. | C08F/2/34 |
| WO | 94/29032 A1 | 12/1994 | ............. | B05B/7/16 |
| WO | 95/00526 A1 | 1/1995 | ............ | C07F/17/00 |
| WO | 95/07942 A1 | 3/1995 | ............ | C08F/10/02 |
| WO | 95/13305 A1 | 5/1995 | ............. | C08F/2/34 |
| WO | 95/13306 A1 | 5/1995 | ............. | C08F/2/34 |
| WO | 96/00244 A1 | 1/1996 | ............ | C08F/10/00 |
| WO | 96/13530 A1 | 5/1996 | ............ | C08F/10/00 |
| WO | 96/23010 A2 | 8/1996 | ......... | C08F/210/16 |
| WO | 97/22635 A1 | 6/1997 | ............ | C08F/10/00 |
| WO | 97/25355 A1 | 7/1997 | ............ | C08F/10/00 |
| WO | 97/42241 A1 | 11/1997 | ......... | C08F/212/04 |
| WO | 98/41529 A1 | 9/1998 | ............ | C07F/17/00 |
| WO | 98/50392 A1 | 11/1998 | ......... | C07F/9/6568 |
| WO | 99/14250 A1 | 3/1999 | ............ | C08F/10/00 |
| WO | 00/01745 A1 | 1/2000 | ......... | C08F/210/16 |
| WO | 02/051634 A1 | 7/2002 | ............ | B32B/27/32 |
| WO | 02/051928 A3 | 7/2002 | ............ | B32B/27/32 |
| WO | 2004/035681 A2 | 4/2004 | ............ | C08L/23/10 |
| WO | 2004/060994 A1 | 7/2004 | ............ | C08L/23/10 |
| WO | 2004/063270 A3 | 7/2004 | ............ | B32B/27/32 |

OTHER PUBLICATIONS

Brintzinger, Hans H., et al., *Angew. Chem. Int. Ed. Engl.,* 1995, 34, 1143–1170.

Chen, Eugene You–Xian, et al., *Chem. Rev. 2000,* 100, 1391–1434.

Coates, Geoffrey W., *Chem. Rev. 2000,* 100, 1223–1252.

Hazlitt, Lonnie G., *Journal of Applied Polymer Science: Applied Power Symposium* 45, 25–37 (1990).

Herzog, Timothy A., et al., *J. Am. Chem. Soc.* 1996, 118, 11988–11989.

Ittel, Steven D., et al., *Chem Rev. 2000,* 100, 1169–1203.

*The Encyclopedia of Chemical Technology,* Kirk–Othmer, Third Edition, John Wiley & Sons, New York, 1981, vol. 1981, pp. 191–192.

*The Encyclopedia of Chemical Technology,* Kirk–Othmer, Third Edition, John Wiley & Sons, New York, 1981, vol. 1981, vol. 16, pp. 416–417.

Lambert, Joseph B., et al., *J. Chem. Soc., Chem. Commun,* 1993, 383–384.

Mathur, Naresh C., et al., *Tetrahedron,* vol. 41, No. 8, 1509–1516, 1985.

Otocka, E.P., et al., *Macromolecules,* vol. 4, No. 4, Jul.–Aug. 1971, 507–514.

Randall, James C., *JMS–Rev. Macromol. Chem. Phys.,* C29(2 & 3), 201–317, 1989.

Resconi, Luigi, et al., *Chem., Rev. 2000,* 100, 1253–1345.

Scholte, Th. G., et al., *Journal of Applied Polymer Science,* vol. 29, 3763–3782, 1984.

Scollard, John D., et al., *J. Am. Chem. Soc.* 1996, 118, 10008–10009.

Veghini, Dario, et al., *J. Am. Chem. Soc.* 1999, 121, 564–573.

Wang, Chunming, et al., *Organometallics,* vol. 17, No. 15, 1998, 3149–3151.

Wild, L. et al., *Journal of Polymer Science Polymer Physics Edition,* vol. 20, 1982, 441–455.

Younkin, Todd R., et al., *Science,* vol. 287, Issue 5452, 2000, 460–462.

News Release, Japan Polychem Launches WINTEC Metal-locene–Based PP Random Copolymer, Oct. 25, 2001, http://www.m–kagaku.co.jp/english/rel/2001/102501.htm.

\* cited by examiner

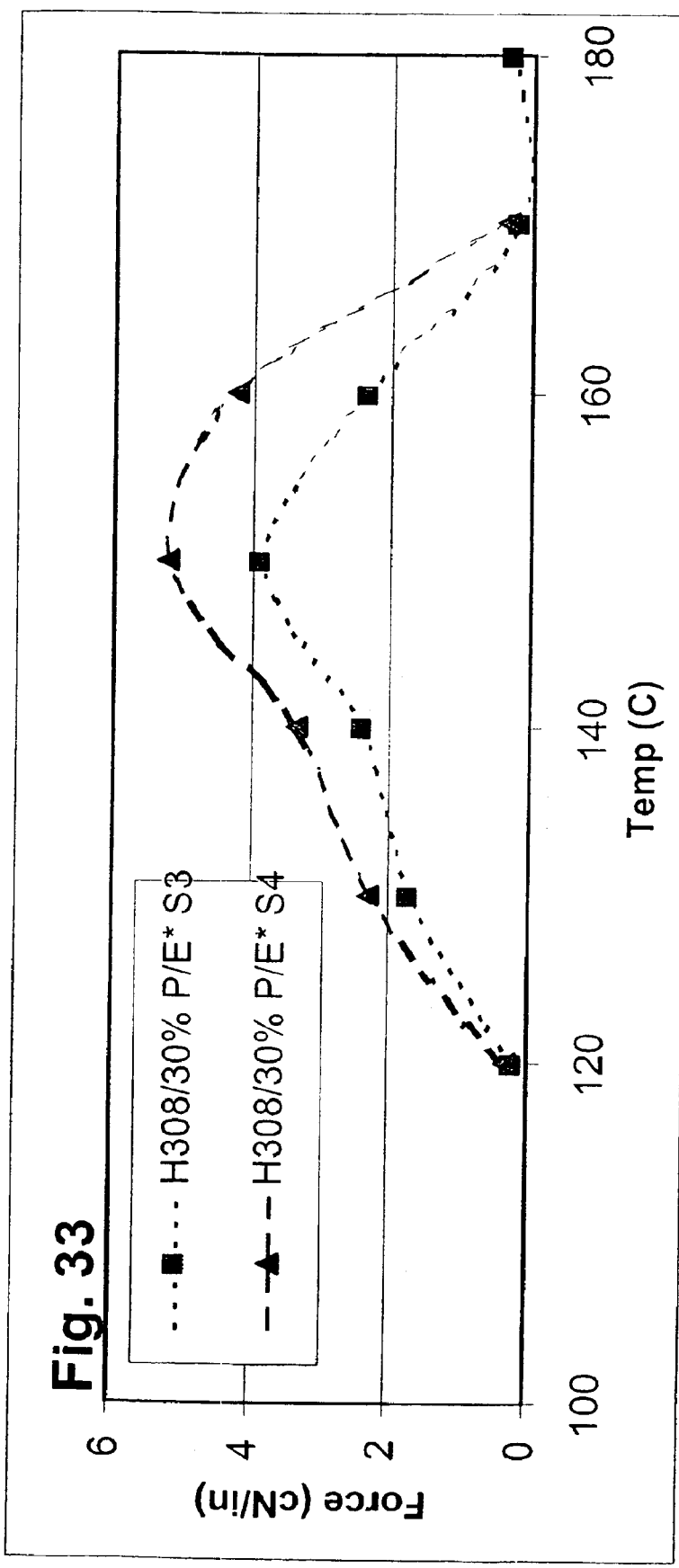

FILMS COMPRISING ISOTACTIC PROPYLENE COPOLYMERS

CROSS REFERENCE TO RELATED APPLICATION

This application is a continuation of U.S. Ser. No. 10/289,168, filed Nov. 5, 2002, and claims the benefit of U.S. Ser. No. 60/338,881 filed Nov. 6, 2001, the disclosures of which are incorporated herein by reference.

FIELD OF THE INVENTION

This invention relates to films comprising polypropylene. In one aspect, the invention relates to films comprising isotactic copolymers of propylene and at least one of ethylene and an unsaturated comonomer while in another aspect, the invention relates to films comprising polymer blends in which at least one blend component is a copolymer of propylene and at least one of ethylene and an unsaturated comonomer.

BACKGROUND OF THE INVENTION

Polypropylene in its many and varied forms is a long established staple of the polymer industry. Depending upon its form, it exhibits a number of desirable properties including toughness (as measured by any of a number of impact tests, e.g., notched Izod, dart drop, etc.), stiffness (as measured by any of a number of modulus tests e.g., Young's), clarity, chemical resistance and heat resistance. Often a particular combination of properties is desired that requires a balancing of various properties against one another (e.g., stiffness against toughness).

Crystalline polypropylene, typically a homopolymer, is used extensively in various moldings because it exhibits desirable mechanical (e.g., rigidity) and chemical resistance properties. For applications that require impact resistance (e.g., automobile parts, appliance facia, packaging, etc.), a copolymer of propylene and ethylene and/or one or more α-olefins is used, or a blend of crystalline polypropylene with one or more polymers that exhibit good impact resistance, e.g., ethylene-propylene (EP) and/or ethylene-propylene-diene (EPDM) rubber. For applications that require toughness and/or heat resistance (e.g., films), preferably the polypropylene has a relatively low melt flow rate (MFR) or expressed alternatively, a relatively high weight average molecular weight ($M_w$). For applications that require good processing characteristics (e.g., fibers), preferably the polypropylene has a relatively narrow polydisperity or molecular weight distribution (MWD), e.g., less than 3.5.

Crystalline polypropylene has an isotactic structure, and it is readily produced using a Ziegler-Natta (Z-N) or a metallocene catalyst. While metallocene catalysts are effective for producing propylene homo- and copolymers with a high isotactic index and a relatively narrow MWD, to produce high $M_w$, e.g., over 300,000, propylene homo- or copolymers economically with a metallocene catalyst is relatively difficult, especially in a solution process. Moreover, the industry maintains a continuing interest in new polypropylene polymers, particularly those for use in film applications.

SUMMARY OF THE INVENTION

In a first embodiment, the invention is a film with excellent machine direction (MD) tear properties. This film has at least one layer having an MD tear of at least 75 grams/mil, and this layer is made from a polymer comprising:

(A) at least 50 weight percent (wt %) propylene; and
(B) at least 5 wt % ethylene and/or one or more unsaturated comonomers.

Representative of component (B) unsatuarated comonomers are the $C_{4\text{-}20}$ α-olefins, $C_{4\text{-}20}$ dienes, styrenic compounds, and the like. Preferably, the film has at least one of a (i) haze value of less than about 10, (ii) 45 degree gloss of greater than about 65, and (iii) dart value of greater than about 100 g/mil, more preferably greater than about 150 g/mil, further more prefereably greater than 175 g/mil, and in some instances greater than 200 g/mil, most preferably greater than 250 g/mil, further most preferably greater than 300 g/mil.

In a second embodiment, the invention is a film containing at least one layer of a polymer comprising an isotactic propylene homopolymer characterized as having $^{13}$C NMR peaks corresponding to a regio-error at about 14.6 and about 15.7 ppm, the peaks of about equal intensity. Preferably, the propylene homopolymer is characterized as having substantially isotactic propylene sequences, i.e., the sequences have an isotactic triad (mm) measured by $^{13}$C NMR of greater than about 0.85. These propylene homopolymers typically have at least 50 percent more of this regio-error than a comparable polypropylene homopolymer prepared with a Ziegler-Natta catalyst. A "comparable" polypropylene as here used means an isotactic propylene homopolymer having the same weight average molecular weight, i.e., within plus or minus 10 wt %.

In a third embodiment, the invention is a film containing at least one layer of a copolymer comprising propylene, ethylene and, optionally, one or more unsaturated comonomers, e.g., $C_{4\text{-}20}$ α-olefins, $C_{4\text{-}20}$ dienes, vinyl aromatic compounds (e.g., styrene), etc. These copolymers are characterized as comprising at least about 60 weight percent (wt %) of units derived from propylene, about 0.1–35 wt % of units derived from ethylene, and 0 to about 35 wt % of units derived from one or more unsaturated comonomers, with the proviso that the combined weight percent of units derived from ethylene and the unsaturated comonomer does not exceed about 40. These copolymers are also characterized as having at least one of the following properties: (i) $^{13}$C NMR peaks corresponding to a regio-error at about 14.6 and about 15.7 ppm, the peaks of about equal intensity, (ii) a B-value greater than about 1.4 when the comonomer content, i.e., the units derived from ethylene and/or the unsaturated comonomer(s), of the copolymer is at least about 3 wt %, (iii) a skewness index, $S_{ix}$, greater than about −1.20, (iv) a DSC curve with a $T_{me}$ that remains essentially the same and a $T_{max}$ that decreases as the amount of comonomer, i.e., the units derived from ethylene and/or the unsaturated comonomer(s), in the copolymer is increased, and (v) an X-ray diffraction pattern that reports more gamma-form crystals than a comparable copolymer prepared with a Ziegler-Natta (Z-N) catalyst. Typically the copolymers of this embodiment are characterized by at least two of these properties. Certain of the copolymers of this embodiment are characterized by at least three of these properties, while other copolymers of this embodiment are characterized by at least four or even all five of these properties.

With respect to the X-ray property of subparagraph (v) above, a "comparable" copolymer is one having the same monomer composition within 10 wt %, and the same Mw within 10 wt %. For example, if the propylene/ethylene/1-hexene copolymer is 9 wt % ethylene and 1 wt % 1-hexene and has a Mw of 250,000, then a comparable polymer would have from 8.1–9.9 wt % ethylene, 0.9–1.1 wt % 1-hexene, and a Mw between 225,000 and 275,000, prepared with a Ziegler-Natta catalyst.

In a fourth embodiment, the invention is a film containing at least one layer of a copolymer comprising propylene and one or more unsaturated comonomers. These copolymers are characterized in having at least about 60 wt % of the units derived from propylene, and between about 0.1 and 40 wt % the units derived from the unsaturated comonomer. These copolymers are also characterized as having at least one of the following properties: (i) $^{13}$C NMR peaks corresponding to a regio-error at about 14.6 and about 15.7 ppm, the peaks of about equal intensity, (ii) a B-value greater than about 1.4 when the comonomer content, i.e., the units derived from the unsaturated comonomer(s), of the copolymer is at least about 3 wt %, (iii) a skewness index, $S_{ix}$, greater than about −1.20, (iv) a DSC curve with a $T_{me}$ that remains essentially the same and a $T_{max}$ that decreases as the amount of comonomer, i.e., the units derived from the unsaturated comonomer(s), in the copolymer is increased, and (v) an X-ray diffraction pattern that reports more gamma-form crystals than a comparable copolymer prepared with a Ziegler-Natta (Z-N) catalyst. Typically the copolymers of this embodiment are characterized by at least two of these properties. Certain of the copolymers of this embodiment are characterized by at least three of these properties, while other copolymers of this embodiment are characterized by at least four or even all five of these properties.

In a fifth embodiment, the invention is a film containing at least one layer of a blend of two or more polymers in which at least one component of the blend, i.e., a first component, comprises at least one of (i) one or more of the propylene/ethylene and propylene/unsaturated comomoner copolymers described in the third and fourth embodiments (occasionally referred to, individually and collectively, as "P/E* copolymer" or similar term), and (ii) one or more of the propylene homopolymer of the second embodiment (occasionally referred to as "P* homopolymer" or similar term). The amount of each polymer component in the blend can vary widely, although preferably the first component comprises at least about 50 weight percent of the blend. The blend may be either homo- or heterophasic. If the latter, the P* homopolymer and/or the P/E* copolymer can be either the continuous or discontinuous (i.e., dispersed) phase.

P/E* copolymers are a unique subset of P/E copolymers. For purposes of this disclosure, P/E copolymers comprise 50 weight percent or more propylene while EP (ethylene-propylene) copolymers comprise 51 weight percent or more ethylene. As here used, "comprise . . . propylene", "comprise . . . ethylene" and similar terms mean that the polymer comprises units derived from propylene, ethylene or the like as opposed to the compounds themselves.

The other polymer component(s) in the blend of this fifth embodiment can be one or more thermoplastic polymers other than the P* and/or P/E* polymer that comprises the first component of the blend. Typically and preferably, this other polymer(s) is (are) a polyolefin such as one or more of a polyethylene, ethylene/α-olefin (e.g., LLDPE, HDPE, LDPE, etc.), butylene/α-olefin, ethylene/styrene and the like. The blend may contain any weight percent, based on the total weight of the blend, of these other components.

Other embodiments of the invention include articles made from the inventive films and the processes of making these articles. Illustrative articles include food and non-food packaging films, bottles, tapes, ribbons, extrusion coatings and the like. Many of these articles comprise multiple layers of film. The processes used to make these articles include blown film, cast film, calendering, extrusion coating, biaxial orienting and compression molding.

BRIEF DESCRIPTION OF THE DRAWINGS

FIG. 33 shows the hot tack behavior of blends of P/E* copolymers with a mini-random propylene-ethylene copolymer.

DESCRIPTION OF THE PREFERRED EMBODIMENTS

Molecular Weight

Figure 1:
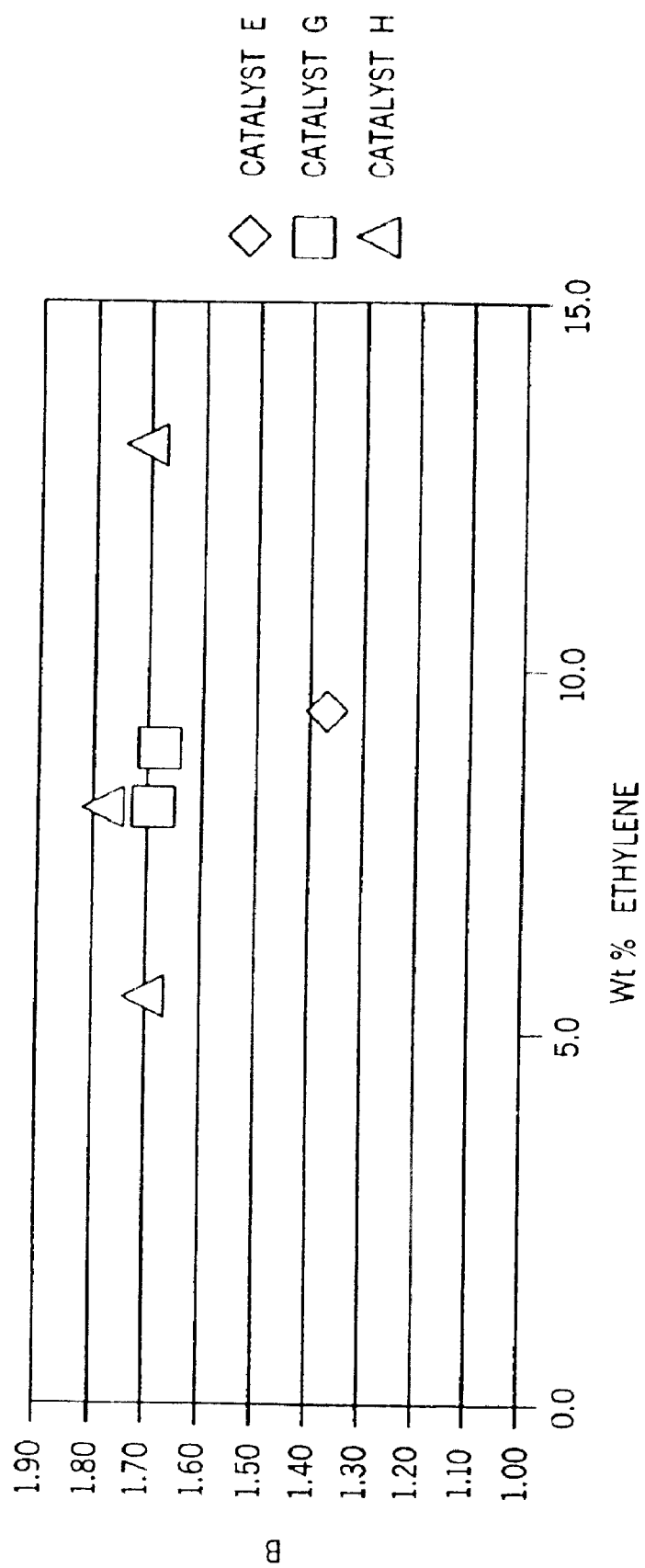
FIG. 1 illustrates the unusual comonomer distribution of a propylene/ethylene (P/E*) copolymer made with a metal-centered, heteroaryl ligand catalyst.

The weight average molecular weight (Mw) of the polymers used in this invention can vary widely, but typically it is between about 30,000 and 1,000,000 (with the understanding that the only limit on the minimum or the maximum $M_w$ is that set by practical considerations). Preferably the minimum Mw is about 50,000, more preferably about 75,000 and even more preferably about 100,000. "High molecular weight", "high weight average molecular weight", "high Mw" and similar terms mean a weight average molecular weight of at least about 250,000, preferably of at least about 300,000 and more preferably 350,000, and more preferably at least about 400,000.

Polydispersity

The polydispersity of the polymers used in the films of this invention is typically between about 2 and about 6. "Narrow polydisperity", "narrow molecular weight distribution", "narrow MWD" and similar terms mean a ratio ($M_w/M_n$) of weight average molecular weight ($M_w$) to number average molecular weight ($M_n$) of less than about 3.5, preferably less than about 3.0, more preferably less than about 2.8, more preferably less than about 2.5, and most preferably less than about 2.3. Polymers for use in extrusion coating applications typically have a narrow polydispersity.

The polydispersity of the polymer blends used in the films of his invention may have greater than that of the individual polymer components of the blend depending, in part, on the molecular weight of the individual blend components. In particular, blends produced utilizing a multiple reactor processes, such as those disclosed below, may have a broad range of polydispersities, e.g., from as low as about 2 to as high as about 100 or more. Preferably, the $M_w/M_n$ of such blends is between about 2 and about 50, more preferably between about 2 and about 20, most preferably between about 2 and about 10.

Gel Permeation Chromatography

Molecular weight distribution of the crystallizable propylene polymers is determined using gel permeation chromatography (GPC) on a Polymer Laboratories PL-GPC-220 high temperature chromatographic unit equipped with four linear mixed bed columns (Polymer Laboratories (20-micron particle size)). The oven temperature is at 160° C. with the autosampler hot zone at 160° C. and the warm zone at 145° C. The solvent is 1,2,4-trichlorobenzene containing 200 ppm 2,6-di-t-butyl-4-methylphenol. The flow rate is 1.0 milliliter/minute and the injection size is 100 microliters. About 0.2% by weight solutions of the samples are prepared for injection by dissolving the sample in nitrogen purged 1,2,4-trichlorobenzene containing 200 ppm 2,6-di-t-butyl-4-methylphenol for 2.5 hrs at 160° C. with gentle mixing.

The molecular weight determination is deduced by using ten narrow molecular weight distribution polystyrene standards (from Polymer Laboratories, EasiCal PS1 ranging from 580–7,500,000 g/mole) in conjunction with their elution volumes. The equivalent polypropylene molecular weights are determined by using appropriate Mark-Houwink coefficients for polypropylene (as described by Th. G. Scholte, N. L. J. Meijerink, H. M. Schoffeleers, and A. M. G. Brands, J. Appl. Polym. Sci., 29, 3763–3782 (1984)) and polystyrene (as described by E. P. Otocka, R. J. Roe, N. Y. Hellman, P. M. Muglia, Macromolecules, 4, 507 (1971)) in the Mark-Houwink equation:

$$\{N\}=KM^a$$

where $K_{pp}$=1.90E-04, $a_{pp}$=0.725 and $K_{ps}$=1.26E-04, $a_{ps}$=0.702.

Differential Scanning Calorimetry

Differential scanning calorimetry (DSC) is a common technique that can be used to examine the melting and crystallization of semi-crystalline polymers. General principles of DSC measurements and applications of DSC to studying semi-crystalline polymers are described in standard texts (e.g., E. A. Turi, ed., *Thermal Characterization of Polymeric Materials*, Academic Press, 1981). Certain of the copolymers used in the practice of this invention are characterized by a DSC curve with a $T_{me}$ that remains essentially the same and a $T_{max}$ that decreases as the amount of unsaturated comonomer in the copolymer is increased. $T_{me}$ means the temperature at which the melting ends. $T_{max}$ means the peak melting temperature.

Differential Scanning Calorimetry (DSC) analysis is determined using a model Q1000 DSC from TA Instruments, Inc. Calibration of the DSC is done as follows. First, a baseline is obtained by running the DSC from −90° C. to 290° C. without any sample in the aluminum DSC pan. Then 7 milligrams of a fresh indium sample is analyzed by heating the sample to 180° C., cooling the sample to 140° C. at a cooling rate of 10° C./min followed by keeping the sample isothermally at 140° C. for 1 minute, followed by heating the sample from 140° C. to 180° C. at a heating rate of 10° C./min. The heat of fusion and the onset of melting of the indium sample are determined and checked to be within 0.5° C. from 156.6° C. for the onset of melting and within 0.5 J/g from 28.71 J/g for the heat of fusion. Then deionized water is analyzed by cooling a small drop of fresh sample in the DSC pan from 25° C. to −30° C. at a cooling rate of 10° C./min. The sample is kept isothermally at −30° C. for 2 minutes and heated to 30° C. at a heating rate of 10° C./min. The onset of melting is determined and checked to be within 0.5° C. from 0° C.

The polypropylene samples are pressed into a thin film at a temperature of 190° C. About 5 to 8 mg of sample is weighed out and placed in the DSC pan. The lid is crimped on the pan to ensure a closed atmosphere. The sample pan is placed in the DSC cell and the heated at a high rate of about 100° C./min to a temperature of about 30° C. above the melt temperature. The sample is kept at this temperature for about 3 minutes. Then the sample is cooled at a rate of 10° C./min to −40° C., and kept isothermally at that temperature for 3 minutes. Consequently the sample is heated at a rate of 10° C./min until complete melting. The resulting enthalpy curves are analyzed for peak melt temperature, onset and peak crystallization temperatures, heat of fusion and heat of crystallization, $T_{me}$, and any other DSC analyses of interest.

B-Value

"High B-value" and similar terms mean the ethylene units of a copolymer of propylene and ethylene, or a copolymer of propylene, ethylene and at least one unsaturated comonomer, is distributed across the polymer chain in a nonrandom manner. B-values range from 0 to 2 with 1 designating a perfectly random distribution of comonomer units. The higher the B-value, the more alternating the comonomer distribution in the copolymer. The lower the B-value, the more blocky or clustered the comonomer distribution in the copolymer. The high B-values of the polymers of this invention are typically at least about 1.3, preferably at least about 1.4, more preferably at least about 1.5 and most preferably at least about 1.7. The B-value is calculated as follows.

B is defined for a propylene/ethylene copolymer as:

$$B = \frac{f(EP + PE)}{2 \cdot F_E \cdot F_P}$$

where f(EP+PE)=the sum of the EP and PE diad fractions; and Fe and Fp=the mole fraction of ethylene and propylene in the copolymer, respectively. B-values can be calculated for other copolymers in an analogous manner by assignment of the respective copolymer diads. For example, calculation of the B-value for a propylene/1-octene copolymer uses the following equation:

$$B = \frac{f(OP + PO)}{2 \cdot F_O \cdot F_P}$$

For propylene polymers made with a metallocene catalyst, the B-values are typically between 1.1 and 1.3. For propylene polymers made with a constrained geometry catalyst, the B-values are typically between 0.9 and 1.0. In contrast, the B-values of the propylene polymers of this invention, typically made with an activated nonmetallocene, metal-centered, heteroaryl ligand catalyst, are above about 1.4, typcially between about 1.5 and about 1.85. In turn, this means that for any P/E* copolymer, not only is the propylene block length relatively short for a given percentage of ethylene but very little, if any, long sequences of 3 or more sequential ethylene insertions are present in the copolymer, unless the ethylene content of the polymer is very high. FIG. 1 and the data of the following tables are illustrative. The catalysts are activated nonmetallocene, metal-centered, heteroaryl ligand catalysts, and these made P/E* polymers. The Catalyst E is a metallocene catalyst, and it did not make the P/E* polymers. Interestingly, the B-values of the P/E* polymers remained high even for polymers with relatively large amounts, e.g., >30 mole %, ethylene.

TABLE A

B-Values of Selected Propylene Polymers

| No | Description | MFR (g/10 min) | Density (kg/dm 3#) | Ethylene (mol %) | Regio-errors 14–16 ppm (mole %) (average of two) | B | Tmax (° C.) | Cryst. (%) (from Hf) | Tg (° C.) |
|---|---|---|---|---|---|---|---|---|---|
| A-1 | P/E* via Catalyst I | 25.8 | 0.8864 | 10.6 | 0.00 | 1.40 | 104.7 | 37.3 | −20.9 |
| A-2 | HPP via Catalyst G | 1.9 | 0.8995 | 0.0 | 1.35 | None | 139.5 | 48.7 | −6.9 |
| A-3 | P/E* via Catalyst G | 1.7 | 0.8740 | 11.8 | 0.24 | 1.67 | 63.3 | 24.4 | −23.6 |
| A-4 | P/E* via Catalyst G | 1.5 | 0.8703 | 12.9 | 0.32 | 1.66 | 57.7 | 21.9 | −24.5 |
| A-5 | HPP via Catalyst H | 2.5 | 0.9021 | 0.0 | 1.18 | none | 143.5 | 61.4 | −6.0 |
| A-6 | P/E* via Catalyst H | 1.9 | 0.8928 | 4.3 | 0.57 | .77 | 120.6 | 48.3 | −13.8 |
| A-7 | P/E* via Catalyst H | 2.2 | 0.8850 | 8.2 | 0.47 | .71 | 96.0 | 40.5 | −19.3 |
| A-8 | P/E* via Catalyst H | 2.3 | 0.8741 | 11.8 | 0.34 | .79 | 67.9 | 27.4 | −23.7 |
| A-9 | P/E* via Catalyst H | 2 | 0.8648 | 15.8 | 0.24 | .67 | 53.7 | 10.5 | −27.6 |
| A-10 | P/E* via Catalyst H | 2.0 | 0.8581 | 18.6 | 0.18 | .70 | none | 2.6 | −29.9 |

Catalyst I is dimethyleamidoborane-bis-η$^5$-(2-methyl-4-napmylinden-1-yl)zirconium η$^4$-1,4,-dipheny-1,3-butadiene.

HPP means polypropylene homopolymer.

TABLE B

B-Values of Selected Propylene/Ethylene Copolymers

| Number | Description | Ethylene (mol %) | Regio-errors 14–16 ppm (mole %) (average of two) | B | Tmax (° C.) | Cryst. (%) (from Hf) | Tg (° C.) |
| --- | --- | --- | --- | --- | --- | --- | --- |
| B-1 | P/E* via Catalyst H | 1.6 | 0.37 | 1.78 | 138.2 | 53.9 | −8.1 |
| B-2 | P/E* via Catalyst H | 7.7 | 0.38 | 1.66 | 105.6 | 38.9 | −18.5 |
| B-3 | P/E* via Catalyst H | 7.8 | 0.41 | 1.61 | 107.7 | 39.6 | −18.2 |
| B-4 | P/E* via Catalyst H | 12.3 | 0.31 | 1.58 | 74.7 | 30.7 | −22.5 |
| B-5 | P/E* via Catalyst H | 14.8 | 0.21 | 1.67 | 90.6 | 31.2 | −22.9 |
| B-6 | P/E* via Catalyst H | 12.4 | 0.31 | 1.61 | 67.4 | 20.8 | −26.8 |
| B-7 | P/E* via Catalyst H | 14.7 | 0.30 | 1.60 | 78.1 | 19.9 | −25.9 |
| B-8 | P/E* via Catalyst H | 33.7 | 0.00 | 1.67 | none | 0.0 | −39.2 |
| B-9 | P/E* via Catalyst H | 31.3 | 0.00 | 1.67 | none | 0.0 | −39.2 |
| B-10 | P/E* via Catalyst J | 12.0 | 0.25 | 1.61 | 72.4 | 33.2 | −22.8 |
| B-11 | P/E* via Catalyst J | 8.9 | 0.37 | 1.63 | 91.4 | 40.1 | −19.8 |
| B-12 | P/E* via Catalyst J | 8.5 | 0.44 | 1.68 | 101.7 | 38.7 | −20.0 |
| B-13 | P/E* via Catalyst J | 7.6 | 0.47 | 1.68 | 107.6 | 43.2 | −18.8 |
| B-14 | P/E* via Catalyst J | 7.6 | 0.35 | 1.64 | 106.2 | 42.4 | −18.5 |
| B-15 | P/E* via Catalyst J | 8.6 | 0.33 | 1.64 | 104.4 | 41.0 | −19.5 |
| B-16 | P/E* via Catalyst J | 9.6 | 0.35 | 1.65 | 85.5 | 38.1 | −20.6 |
| B-17 | P/E* via Catalyst J | 8.6 | 0.37 | 1.63 | 104.1 | 41.8 | −19.6 |
| B-18 | P/E* via Catalyst J | 8.6 | 0.34 | 1.62 | 90.8 | 40.8 | −19.6 |
| B-19 | P/E* via Catalyst J | 8.6 | 0.40 | 1.58 | 93.3 | 41.9 | −19.2 |

Figure 2A:
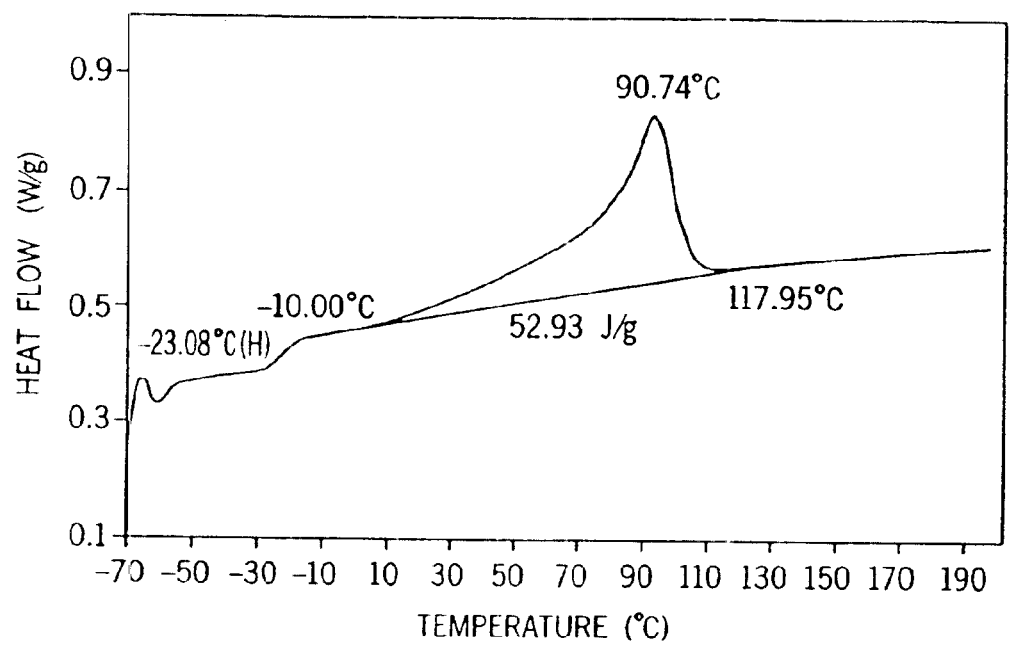
FIGS. 2A and 2B show a comparison of the DSC heating traces of the propylene/ethylene (P/E) copolymer of Comparative Example 1 and the P/E* copolymer of Example 2, respectively.
Figure 2B:
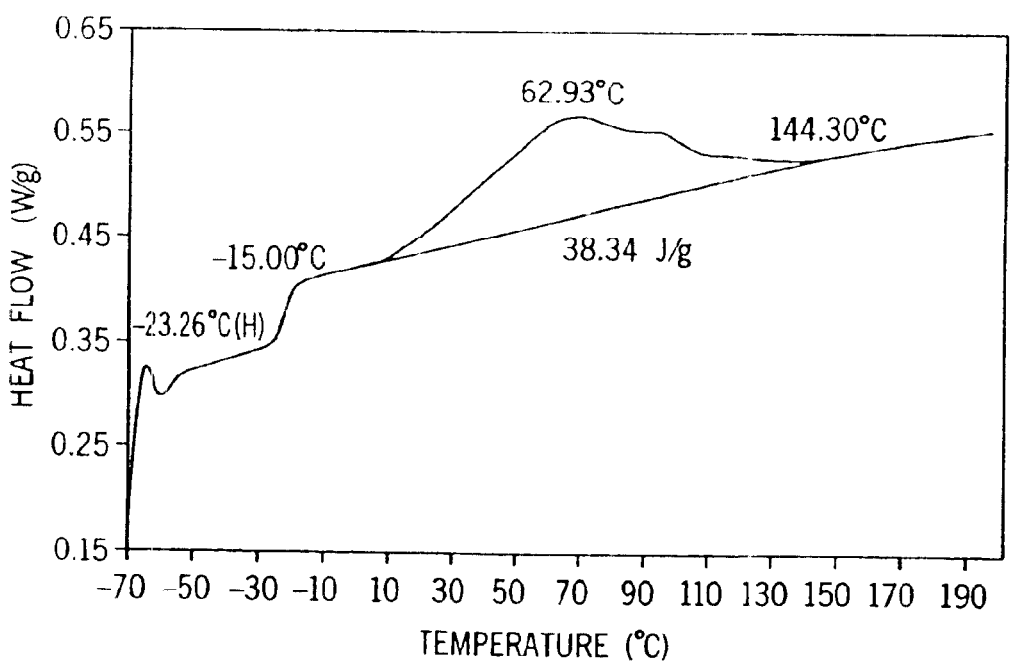

The processes described below can be used to produce propylene interpolymers of ethylene and optionally $C_4$–$C_{20}$ alpha-olefins having a relatively broad melting point in a DSC heating curve. While not wishing to be held to any particular theory of operation, it is believed that the high B values for the novel propylene/ethylene interpolymers and the process for their manufacture lead to an ethylene distribution within the polymer chains that leads to a broad melting behavior. In FIGS. 2A and 2B, for example, a relatively narrow melting peak is observed for a propylene/ethylene copolymer prepared using a metallocene as a comparative example (Comparative Example 1), while the melting peak for a similar copolymer of propylene and ethylene prepared according to the teachings herein exhibits a broad melting point. Such broad melting behavior is useful in applications requiring, for example, a relatively low heat seal initiation temperature, or a broad hot tack and/or heat seal window.

Thermal Properties

Figure 3:
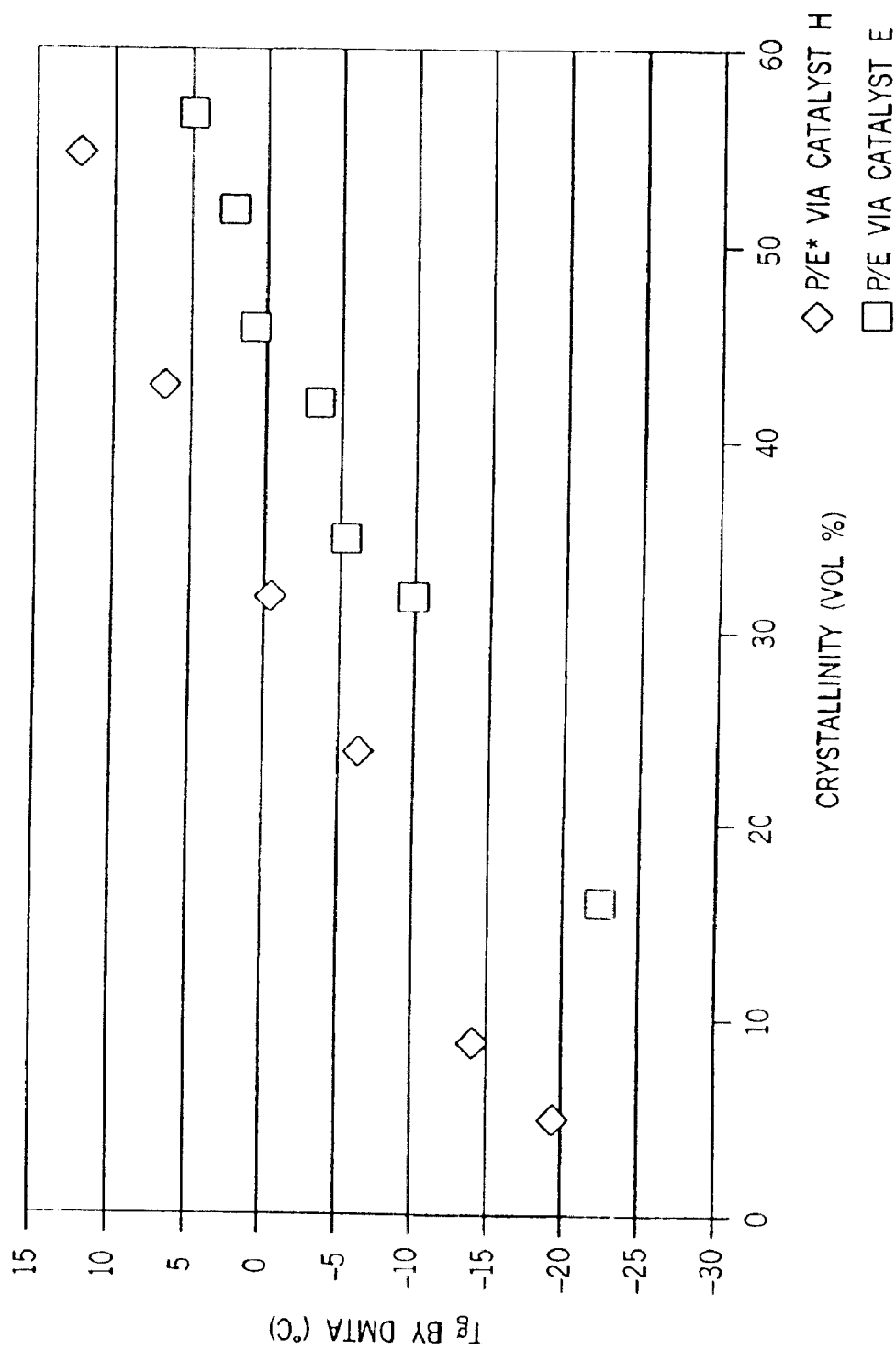
FIG. 3 shows a comparison of the Tg data of a P/E* copolymer and a conventional Ziegler-Natta (Z-N) catalyzed P/E copolymer at equivalent crystallinity.
Figure 4:
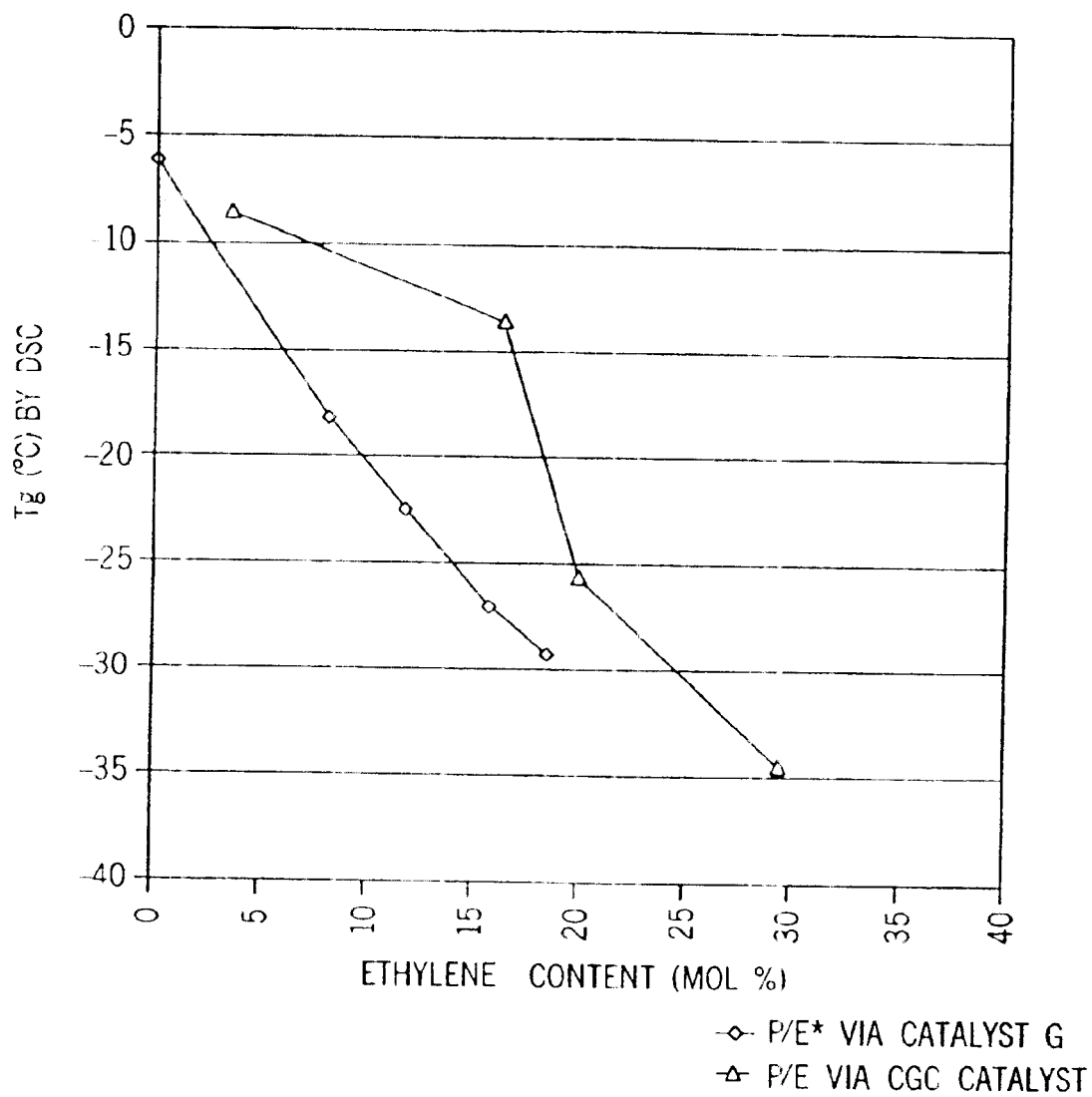
FIG. 4 shows a comparison of the Tg data of a P/E* copolymer and a conventional constrained geometry catalyst (CGC) P/E copolymer at the same ethylene content.

FIGS. 3 and 4 further illustrate the thermal properties of the P/E* polymers used in the practice of this invention. FIG. 3 illustrates that the P/E* polymers have a higher glass transition temperature (Tg) than do comparable metallocene-catalysed propylene polymers at a equivalent crystallinity. This means that the P/E* copolymers are likely to exhibit better creep resistance than conventional metallocene-catalyzed propylene copolymers. Moreover, the $T_{max}$ data of Table A shows that the P/E* copolymers have a lower melting point at the same crystallinity as a metallocene-catalyzed propylene copolymer. This, in turn, means that the P/E* polymers are likely to process better (e.g., require less heating) than conventional metallocene-catalyzed propylene polymers.

FIG. 4 illustrates that the P/E* polymers also have a lower Tg at an equivalent ethylene content than a propylene polymer made with a constrained geometry catalyst (CGC) and this, in turn, means that the P/E* polymers are likely to exhibit better low temperature toughness than the CGC propylene polymers making the P/E* polymers attractive candidates for food packaging applications.

Temperature-Rising Elution Fractionation

The determination of crystallizable sequence length distribution can be accomplished on a preparative scale by temperature-rising elution fractionation (TREF). The relative mass of individual fractions can be used as a basis for estimating a more continuous distribution. L. Wild, et al., *Journal of Polymer Science: Polymer. Physics Ed.*, 20, 441 (1982), scaled down the sample size and added a mass detector to produce a continuous representation of the distribution as a function of elution temperature. This scaled down version, analytical temperature-rising elution fractionation (ATREF), is not concerned with the actual isolation of fractions, but with more accurately determining the weight distribution of fractions.

While TREF was originally applied to copolymers of ethylene and higher α-olefins, it can also be used for the analysis of copolymers of propylene with ethylene (or higher α-olefins). The analysis of copolymers of propylene requires higher temperatures for the dissolution and crystallization of pure, isotactic polypropylene, but most of the copolymerization products of interest elute at similar temperatures as observed for copolymers of ethylene. The following table is a summary of conditions used for the analysis of copolymers of propylene. Except as noted the conditions for TREF are consistent with those of Wild, et al., ibid, and Hazlitt, *Journal of Applied Polymer Science: Appl. Polym. Symp.*, 45, 25(1990).

TABLE C

Parameters Used for TREF

| Parameter | Explanation |
| --- | --- |
| Column type and size | Stainless steel shot with 1.5 cc interstitial volume |
| Mass detector | Single beam infrared detector at 2920 cm$^{-1}$ |
| Injection temperature | 150° C. |
| Temperature control device | GC oven |
| Solvent | 1,2,4-trichlorobenzene |
| Concentration | 0.1 to 0.3% (weight/weight) |
| Cooling Rate 1 | 140° C. to 120° C. @ −6.0° C./min. |
| Cooling Rate 2 | 120° C. to 44.5° C. @ −0.1° C./min. |

TABLE C-continued

Parameters Used for TREF

| Parameter | Explanation |
| --- | --- |
| Cooling Rate 3 | 44.5° C. to 20° C. @ −0.3° C./min. |
| Heating Rate | 20° C. to 140° C. @ 1.8° C./min. |
| Data acquisition rate | 12/min. |

Figure 5:
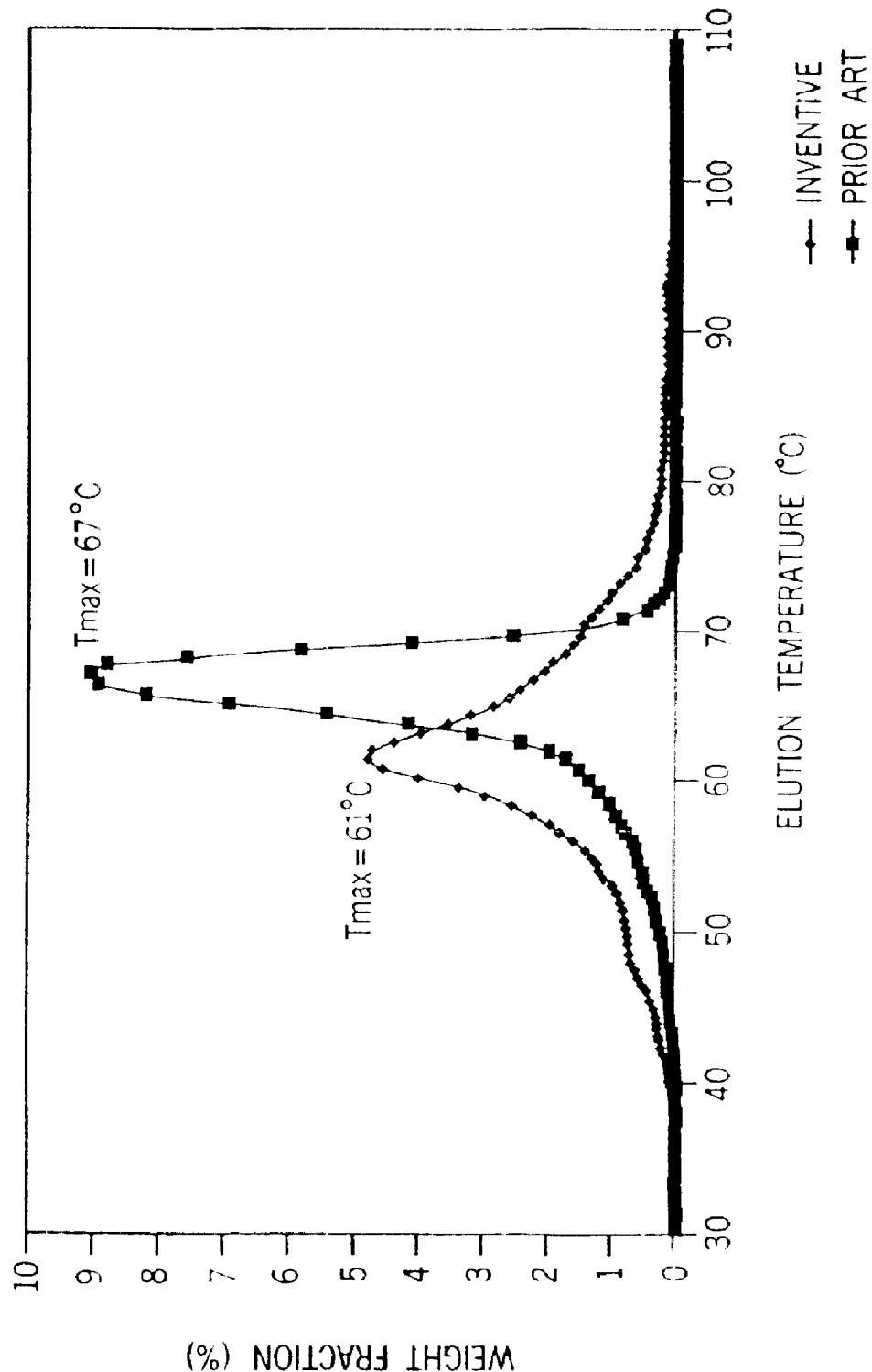
FIG. 5 shows a comparison of a TREF curve for a conventional metallocene-catalyzed P/E copolymer and a P/E* copolymer.

The data obtained from TREF are expressed as a normalized plot of weight fraction as a function of elution temperature. The separation mechanism is analogous to that of copolymers of ethylene, whereby the molar content of the crystallizable component (ethylene) is the primary factor that determines the elution temperature. In the case of copolymers of propylene, it is the molar content of isotactic propylene units that primarily determines the elution temperature. FIG. 5 is a representation of the typical type of distribution one would expect for a propylene/ethylene copolymer made with a metallocene polymer and an example of a P/E* copolymer.

The shape of the metallocene curve in FIG. 5 is typical for a homogeneous copolymer. The shape arises from the inherent, random incorporation of comonomer. A prominent characteristic of the shape of the curve is the tailing at lower elution temperature compared to the sharpness or steepness of the curve at the higher elution temperatures. A statistic that reflects this type of assymetry is skewness. Equation 1 mathematically represents the skewness index, $S_{ix}$, as a measure of this asymmetry.

$$S_{ix} = \frac{\sqrt[3]{\sum w_i * (T_i - T_{\text{Max}})^3}}{\sqrt{\sum w_i * (T_i - T_{\text{Max}})^2}}$$

Equation 1

The value, $T_{Max}$, is defined as the temperature of the largest weight fraction eluting between 50 and 90° C. in the TREF curve. $T_i$ and $w_i$ are the elution temperature and weight fraction respectively of an abitrary, $i^{th}$ fraction in the TREF distribution. The distributions have been normalized (the sum of the $w_i$ equals 100%) with respect to the total area of the curve eluting above 30° C. Thus, the index reflects only the shape of the crystallized polymer and any uncrystallized polymer (polymer still in solution at or below 30° C.) has been omitted from the calculation shown in Equation 1.

Polymer Definitions and Descriptions

"Polymer" means a macromolecular compound prepared by polymerizing monomers of the same or different type. "Polymer" includes homopolymers, copolymers, terpolymers, interpolymers, and so on. The term "interpolymer" means a polymer prepared by the polymerization of at least two types of monomers or comonomers. It includes, but is not limited to, copolymers (which usually refers to polymers prepared from two different types of monomers or comonomers, although it is often used interchangeably with "interpolymer" to refer to polymers made from three or more different types of monomers or comonomers), terpolymers (which usually refers to polymers prepared from three different types of monomers or comonomers), tetrapolymers (which usually refers to polymers prepared from four different types of monomers or comonomers), and the like. The terms "monomer" or "comonomer" are used interchangeably, and they refer to any compound with a polymerizable moiety which is added to a reactor in order to produce a polymer. In those instances in which a polymer is described as comprising one or more monomers, e.g., a polymer comprising propylene and ethylene, the polymer, of course, comprises units derived from the monomers, e.g., —CH$_2$—CH$_2$—, and not the monomer itself, e.g., CH$_2$=CH$_2$.

"Metallocene-catalyzed polymer" or similar term means any polymer that is made in the presence of a metallocene catalyst. "Constrained geometry catalyst catalyzed polymer", "CGC-catalyzed polymer" or similar term means any polymer that is made in the presence of a constrained geometry catalyst. "Ziegler-Natta-catalyzed polymer", Z-N-catalyzed polymer" or similar term means any polymer that is made in the presence of a Ziegler-Natta catalyst. "Metallocene" means a metal-containing compound having at least one substituted or unsubstituted cyclopentadienyl group bound to the metal. "Constrained geometry catalyst" or "CGC" as here used has the same meaning as this term is defined and described in U.S. Pat. Nos. 5,272,236 and 5,278,272.

"Random copolymer" means a copolymer in which the monomer is randomly distributed across the polymer chain.

"Propylene homopolymer" and similar terms mean a polymer consisting solely or essentially all of units derived from propylene. "Polypropylene copolymer" and similar terms mean a polymer comprising units derived from propylene and ethylene and/or one or more unsaturated comonomers. The term "copolymer" includes terpolymers, tetrapolymers, etc.

The unsaturated comonomers used in the practice of this invention include $C_{4-20}$ α-olefins, especially $C_{4-12}$ α-olefins such as 1-butene, 1-pentene, 1-hexene, 4-methyl-1-pentene 1-heptene, 1-octene, 1-decene, 1-dodecene and the like; $C_{4-20}$ diolefins, preferably 1,3-butadiene, 1,3-pentadiene, norbornadiene, 5-ethylidene-2-norbornene (ENB) and dicyclopentadiene; $C_{8-40}$ vinyl aromatic compounds including sytrene, o-, m-, and p-methylstyrene, divinylbenzene, vinylbiphenyl, vinylnapthalene; and halogen-substituted $C_{8-40}$ vinyl aromatic compounds such as chlorostyrene and fluorostyrene. For purposes of this invention, ethylene and propylene not included in the definition of unsaturated comonomers.

The propylene copolymers used in the practice of this invention typically comprise units derived from propylene in an amount of at least about 60, preferably at least about 80 and more preferably at least about 85, wt % of the copolymer. The typical amount of units derived from ethylene in propylene/ethylene copolymers is at least about 0.1, preferably at least about 1 and more preferably at least about 5 wt %, and the maximum amount of units derived from ethylene present in these copolymers is typically not in excess of about 35, preferably not in excess of about 30 and more preferably not in excess of about 20, wt % of the copolymer. The amount of units derived from the unsaturated comonomer(s), if present, is typically at least about 0.01, preferably at least about 1 and more preferably at least about 5, wt %, and the typical maximum amount of units derived from the unsaturated comonomer(s) typically does not exceed about 35, preferably it does not exceed about 30 and more preferably it does not exceed about 20, wt % of the copolymer. The combined total of units derived from ethylene and any unsaturated comonomer typically does not exceed about 40, preferably it does not exceed about 30 and more preferably it does not exceed about 20, wt % of the copolymer.

The copolymers used in the practice of this invention comprising propylene and one or more unsaturated comonomers (other than ethylene) also typically comprise units derived from propylene in an amount of at least about 60, preferably at least about 70 and more preferably at least about 80, wt % of the copolymer. The one or more unsaturated comonomers of the copolymer comprise at least about 0.1, preferably at least about 1 and more preferably at least about 3, weight percent, and the typical maximum amount of unsaturated comonomer does not exceed about 40, and preferably it does not exceed about 30, wt % of the copolymer.

$^{13}$C NMR

The P/E* polymers used in the practice of this invention are further characterized as having substantially isotactic propylene sequences. "Substantially isotactic propylene sequences" and similar terms mean that the sequences have an isotactic triad (mm) measured by $^{13}$C NMR of greater than about 0.85, preferably greater than about 0.90, more preferably greater than about 0.92 and most preferably greater than about 0.93. Isotactic triads are well known in the art and are described in, for example, U.S. Pat. No. 5,504,172 and WO 00/01745 which refer to the isotactic sequence in terms of a triad unit in the copolymer molecular chain determined by $^{13}$C NMR spectra. The NMR spectra are determined as follows.

$^{13}$C NMR spectroscopy is one of a number of techniques known in the art of measuring comonomer incorporation into a polymer. An example of this technique is described for the determination of comonomer content for ethylene/a-olefin copolymers in Randall (Journal of Macromolecular Science, Reviews in Macromolecular Chemistry and Physics, C29 (2 & 3), 201–317 (1989)). The basic procedure for determining the comonomer content of an olefin interpolymer involves obtaining the $^{13}$C NMR spectrum under conditions where the intensity of the peaks corresponding to the different carbons in the sample is directly proportional to the total number of contributing nuclei in the sample. Methods for ensuring this proportionality are known in the art and involve allowance for sufficient time for relaxation after a pulse, the use of gated-decoupling techniques, relaxation agents, and the like. The relative intensity of a peak or group of peaks is obtained in practice from its computer-generated integral. After obtaining the spectrum and integrating the peaks, those peaks associated with the comonomer are assigned. This assignment can be made by reference to known spectra or literature, or by synthesis and analysis of model compounds, or by the use of isotopically labeled comonomer. The mole % comonomer can be determined by the ratio of the integrals corresponding to the number of moles of comonomer to the integrals corresponding to the number of moles of all of the monomers in the interpolymer, as described in Randall, for example.

The data is collected using a Varian UNITY Plus 400 MHz NMR spectrometer, corresponding to a $^{13}$C resonance frequency of 100.4 MHz. Acquisition parameters are selected to ensure quantitative $^{13}$C data acquisition in the presence of the relaxation agent. The data is acquired using gated $^1$H decoupling, 4000 transients per data file, a 7 sec pulse repetition delay, spectral width of 24,200 Hz and a file size of 32K data points, with the probe head heated to 130° C. The sample is prepared by adding approximately 3 mL of a 50/50 mixture of tetrachloroethane-d2/orthodichlorobenzene that is 0.025M in chromium acetylacetonate (relaxation agent) to 0.4 g sample in a 10 mm NMR tube. The headspace of the tube is purged of oxygen by displacement with pure nitrogen. The sample is dissolved and homogenized by heating the tube and its contents to 150° C. with periodic refluxing initiated by heat gun. Following data collection, the chemical shifts are internally referenced to the mmmm pentad at 21.90 ppm.

For propylene/ethylene copolymers, the following procedure is used to calculate the percent ethylene in the polymer. Integral regions are determined as follows:

TABLE D

Integral Regions for Determining % Ethylene

| Region designation | Ppm |
|---|---|
| A | 44–49 |
| B | 36–39 |
| C | 32.8–34 |
| P | 31.0–30.8 |
| Q | Peak at 30.4 |
| R | Peak at 30 |
| F | 28.0–29.7 |
| G | 26–28.3 |
| H | 24–26 |
| I | 19–23 |

Region D is calculated as D=P−(G−Q)/2. Region E=R+Q+(G−Q)/2.

TABLE E

Calculation of Region D

PPP = (F + A − 0.5D)/2
PPE = D
EPE = C
EEE = (E − 0.5G)/2
PEE = G
PEP = H
Moles P = sum P centered triads
Moles E = sum E centered triads
Moles P = (B + 2A)/2
Moles E = (E + G + 0.5B + H)/2

C2 values are calculated as the average of the two methods above (triad summation and algebraic) although the two do not usually vary.

The mole fraction of propylene insertions resulting in regio-errors is calculated as one half of the sum of the two of methyls showing up at 14.6 and 15.7 ppm divided by the total methyls at 14–22 ppm attributable to propylene. The mole percent of the regio-error peaks is the mole fraction times 100.

Isotacticity at the triad level (mm) is determined from the integrals of the mm triad (22.70–21.28 ppm), the mr triad (21.28–20.67 ppm) and the rr triad (20.67–19.74). The mm isotacticity is determined by dividing the intensity of the mm triad by the sum of the mm, mr, and rr triads. For ethylene copolymers the mr region is corrected by subtracting 37.5–39 ppm integral. For copolymers with other monomers that produce peaks in the regions of the mm, mr, and rr triads, the integrals for these regions are similarly corrected by subtracting the intensity of the interfering peak using standard NMR techniques, once the peaks have been identified. This can be accomplished, for example, by analysis of a series of copolymers of various levels of monomer incorporation, by literature assignments, by isotopic labeling, or other means which are known in the art.

The $^{13}$C NMR peaks corresponding to a regio-error at about 14.6 and about 15.7 ppm are believed to be the result of stereoselective 2,1-insertion errors of propylene units into the growing polymer chain. In a typical P/E* polymer, these peaks are of about equal intensity, and they represent about 0.02 to about 7 mole percent of the propylene insertions into the homopolymer or copolymer chain. For some embodiments, they represent about 0.005 to about 20 mole % or more of the propylene insertions. In general, higher levels of regio-errors lead to a lowering of the melting point and the modulus of the polymer, while lower levels lead to a higher melting point and a higher modulus of the polymer.

The nature and level of comonomers other than propylene also control the melting point and modulus of the copolymer. In any particular application, it may be desirable to have either a high or low melting point or a high or low modulus modulus. The level of regio-errors can be controlled by several means, including the polymerization temperature, the concentration of propylene and other monomers in the process, the type of (co)monomers, and other factors. Various individual catalyst structures may inherently produce more or less regio-errors than other catalysts. For example, in Table A above, the propylene homopolymer prepared with Catalyst G has a higher level of regio-errors and a lower melting point than the propylene homopolymer prepared with Catalyst H, which has a higher melting point. If a higher melting point (or higher modulus) polymer is desired, then it is preferable to have fewer regio-errors than about 3 mole % of the propylene insertions, more preferably less than about 1.5 mole % of the propylene insertions, still more preferably less than about 1.0 mole % of the propylene insertions, and most preferably less than about 0.5 mole % of the propylene insertions. If a lower melting point (or modulus) polymer is desired, then it is preferable to have more regio-errors than about 3 mole % of the propylene insertions, more preferably more than about 5 mole % of the propylene insertions, still more preferably more than about 6 mole % of the propylene insertions, and most preferably more than about 10 mole % of the propylene insertions.

Those skilled artisan will appreciate that the mole % of regio-errors for a P/E* polymer which is a component of a blend refers to the mole % of regio-errors of the particular P/E* polymer component of the blend, and not as a mole % of the overall blend.

Figure 6:
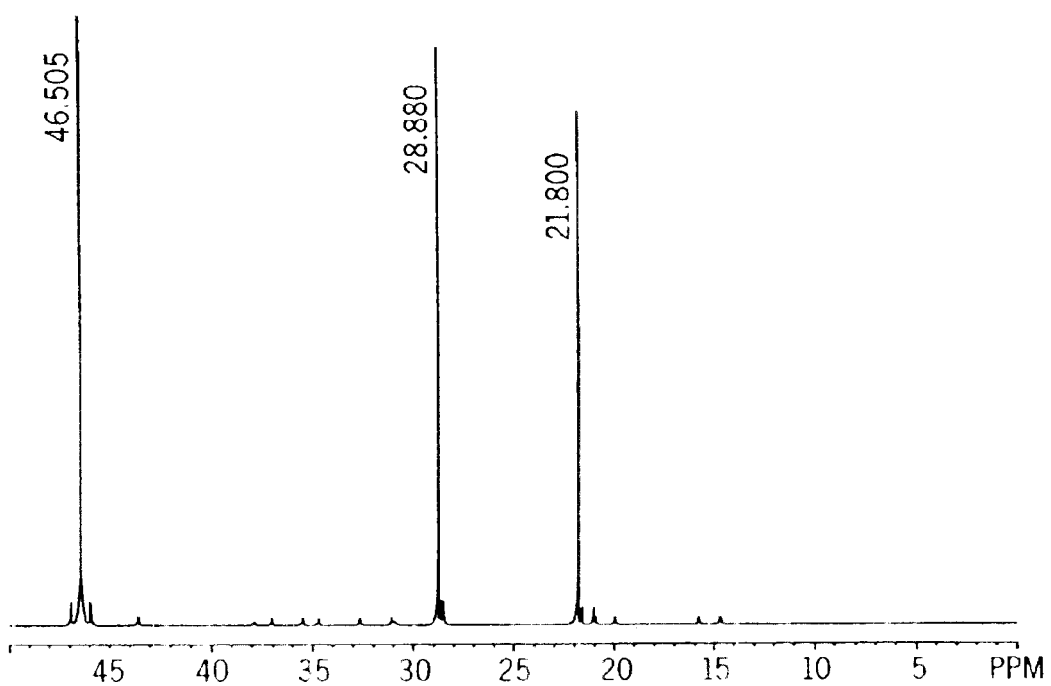
FIG. 6 shows the $^{13}$C NMR spectrum of the propylene (P*) homopolymer product of Example 7, prepared using Catalyst G. This spectrum shows the high degree of isotacticity of the product.
Figure 7:
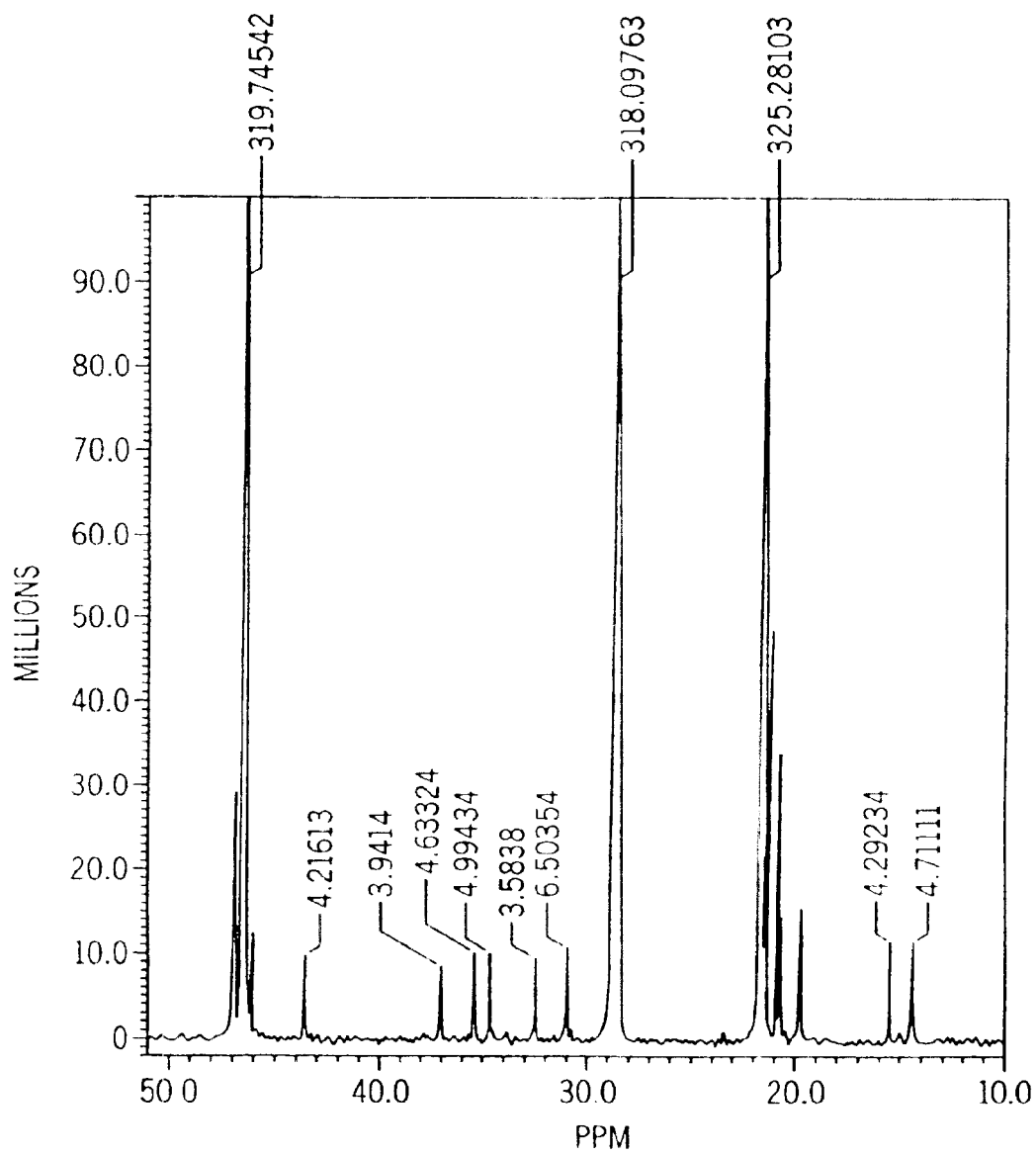
FIG. 7 shows the $^{13}$C NMR spectrum of the P* homopolymer product of Example 8 prepared using Catalyst H. This spectrum is shown at an expanded Y-axis scale relative to FIG. 6 in order to more clearly show the regio-error peaks.
Figure 8:
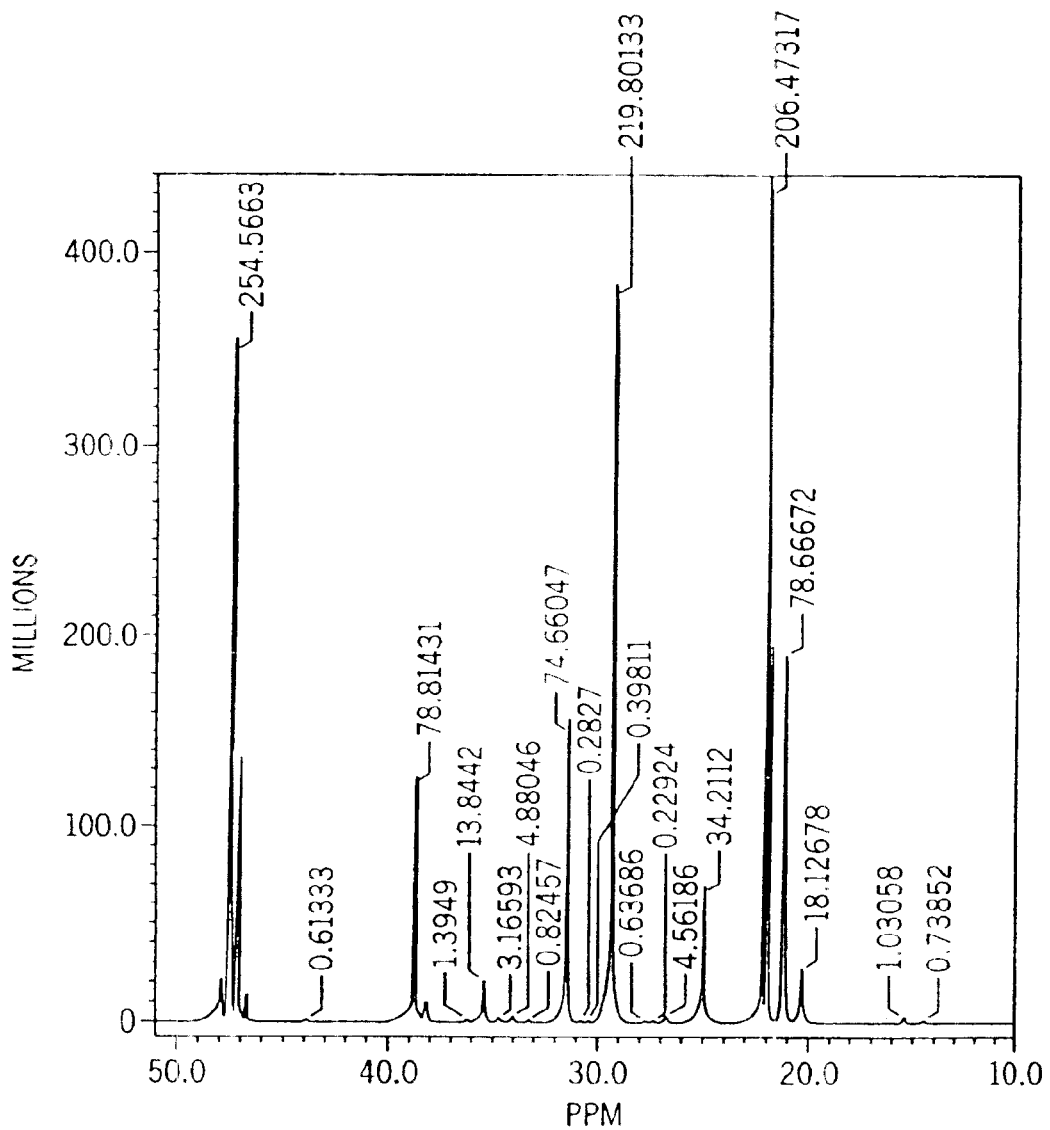
FIG. 8 shows the $^{13}$C NMR Spectrum of the P/E* copolymer product of Example 2 prepared using Catalyst G.
Figure 9:
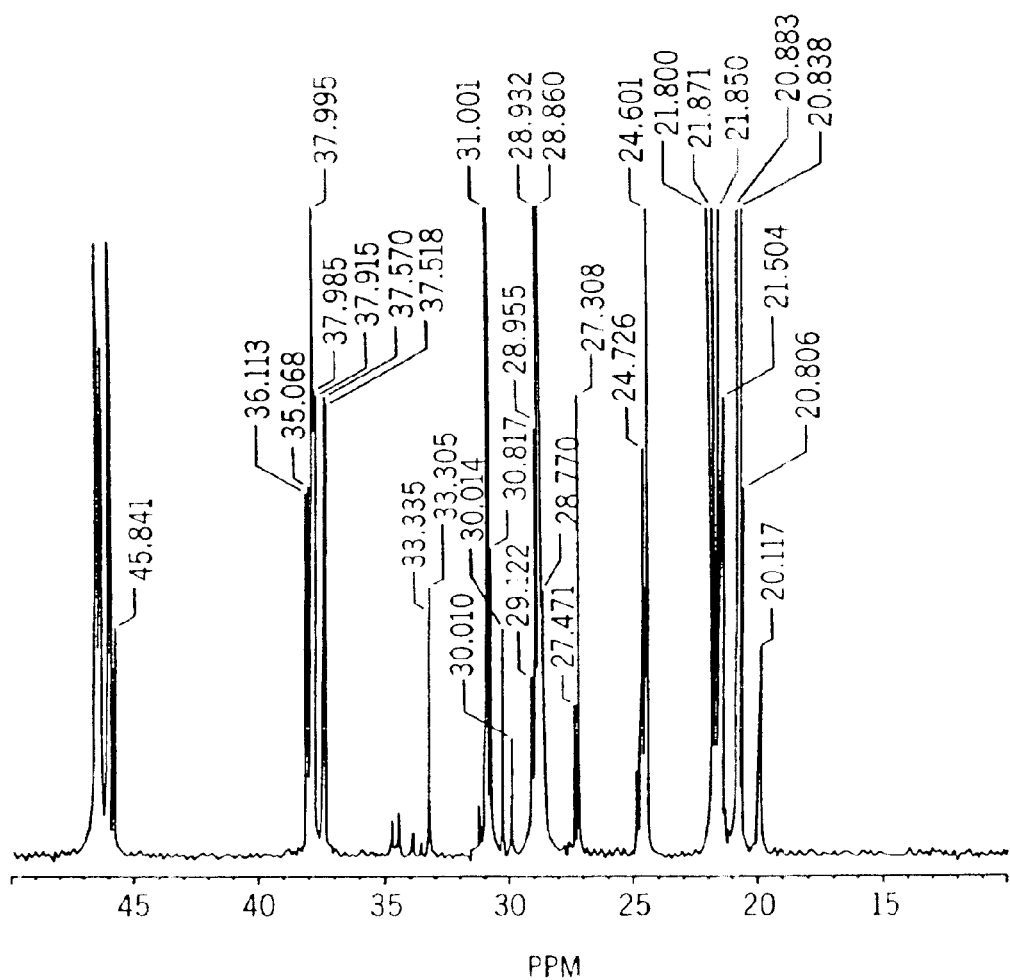
FIG. 9 shows the $^{13}$C NMR Spectrum of the P/E copolymer product of Comparative Example 1 prepared using metallocene Catalyst E demonstrating the absence of regio-error peaks in the region around 15 ppm.

The comparison of several $^{13}$C NMR sprectra further illustrates the unique regio-errors of the P/E* polymers. FIGS. 6 and 7 are the spectra of the propylene homopolymer products of Examples 7 and 8, respectively, each made with an activated nonmetallocene, metal-centered, heteroaryl ligand catalyst. The spectrum of each polymer reports a high degree of isotacticity and the unique regio-errors of these inventive polymers. FIG. 8 is the $^{13}$C NMR spectrum of the propylene-ethylene copolymer of Example 2, made with the same catalyst used to make the propylene homopolymer of Example 7, and it too reports a high degree of isotacticity and the same regio-errors of the propylene homopolymers of FIG. 9. The presence of the ethylene comonomer does not preclude the occurrence of these unique regio-errors. The $^3$C NMR spectrum of FIG. 9 is that of the propylene-ethylene copolymer product of Comparative Example 1 which was prepared using a metallocene catalyst. This spectrum does not report the regio-error (around 15 ppm) characteristic of the P/E* polymers.

Melt Flow Rate (MFR)

The propylene homo- and copolymers used in this invention typically have an MFR of at least about 0.01, preferably at least about 0.05, more preferably at least about 0.1 and most preferably at least about 0.2. The maximum MFR typically does not exceed about 1,000, preferably it does not exceed about 500, more preferably it does not exceed about 100, more preferably it does not exceed about 80 and most preferably it does not exceed about 50. The MFR for propylene homopolymers and copolymers of propylene and ethylene and/or one or more $C_4$–$C_{20}$ α olefins is measured according to ASTM D-1238, condition L (2.16 kg, 230 degrees C.).

Propylene Copolymers

The propylene copolymers used in this invention of particular interest include propylene/ethylene, propylene/1-butene, propylene/1-hexene, propylene/4-methyl-1-pentene, propylene/1-octene, propylene/ethylene/1-butene, propylene/ethylene/ENB, propylene/ethylene/1-hexene, propylene/ethylene/1-octene, propylene/styrene, and propylene/ethylene/styrene.

Catalyst Definitions and Descriptions

The P* and P/E* polymers used in the practice of this invention are made using a metal-centered, heteroaryl ligand catalyst in combination with one or more activators, e.g., an alumoxane. In certain embodiments, the metal is one or more of hafnium and zirconium.

More specifically, in certain embodiments of the catalyst, the use of a hafnium metal has been found to be preferred as compared to a zirconium metal for heteroaryl ligand catalysts. A broad range of ancillary ligand substituents may accommodate the enhanced catalytic performance. The catalysts in certain embodiments are compositions comprising the ligand and metal precursor, and, optionally, may additionally include an activator, combination of activators or activator package.

The catalysts used to make the P* and P/E* polymers additionally include catalysts comprising ancillary ligand-hafnium complexes, ancillary ligand-zirconium complexes and optionally activators, which catalyze polymerization and copolymerization reactions, particularly with monomers that are olefins, diolefins or other unsaturated compounds. Zirconium complexes, hafnium complexes, compositions or compounds using the disclosed ligands are within the scope of the catalysts useful in the practice of this invention. The metal-ligand complexes may be in a neutral or charged state. The ligand to metal ratio may also vary, the exact ratio being dependent on the nature of the ligand and metal-ligand complex. The metal-ligand complex or complexes may take different forms, for example, they may be monomeric, dimeric or of an even higher order.

"Nonmetallocene" means that the metal of the catalyst is not attached to a substituted or unsubstituted cyclopentadienyl ring. Representative nonmetallocene, metal-centered, heteroaryl ligand catalysts are described in U.S. Provisional Patent Application Nos. 60/246,781 filed Nov. 7, 2000 and 60/301,666 filed Jun. 28, 2001.

As here used, "nonmetallocene, metal-centered, heteroaryl ligand catalyst" means the catalyst derived from the ligand described in formula I. As used in this phrase, "heteroaryl" includes substituted heteroaryl.

As used herein, the phrase "characterized by the formula" is not intended to be limiting and is used in the same way that "comprising" is commonly used. The term "independently selected" is used herein to indicate that the R groups, e.g., $R^1$, $R^2$, $R^3$, $R^4$, and $R^5$ can be identical or different (e.g. $R^1$, $R^2$, $R^3$, $R^4$, and $R^5$ may all be substituted alkyls or $R^1$ and $R^2$ may be a substituted alkyl and $R^3$ may be an aryl, etc.). Use of the singular includes use of the plural and vice versa (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. For the purposes of illustration, representative certain groups are defined herein. These definitions are intended to supplement and illustrate, not preclude, the definitions known to those of skill in the art.

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

"Substituted alkyl" refers to an alkyl as just described in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, halogen, alkylhalos (e.g., $CF_3$), hydroxy, amino, phosphido, alkoxy, amino, thio, nitro, and combinations thereof. Suitable substituted alkyls include, for example, benzyl, trifluoromethyl and the like.

The term "heteroalkyl" refers to an alkyl as described above in which one or more carbon atoms to any carbon of the alkyl is replaced by a heteroatom selected from the group consisting of N, O, P, B, S, Si, Sb, Al, Sn, As, Se and Ge. This same list of heteroatoms is useful throughout this specification. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl and the like.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

"Substituted cycloalkyl" refers to cycloalkyl as just described including in which one or more hydrogen atom to any carbon of the cycloalkyl is replaced by another group such as a halogen, alkyl, substituted alkyl, aryl, substituted aryl, cycloalkyl, substituted cycloalkyl, heterocycloalkyl, substituted heterocycloalkyl, heteroaryl, substituted heteroaryl, alkoxy, aryloxy, boryl, phosphino, amino, silyl, thio, seleno and combinations thereof. Suitable substituted cycloalkyl radicals include, for example, 4-dimethylaminocyclohexyl, 4,5-dibromocyclohept-4-enyl, and the like.

The term "heterocycloalkyl" is used herein to refer to a cycloalkyl radical as described, but in which one or more or all carbon atoms of the saturated or unsaturated cyclic radical are replaced by a heteroatom such as nitrogen, phosphorous, oxygen, sulfur, silicon, germanium, selenium, or boron. Suitable heterocycloalkyls include, for example, piperazinyl, morpholinyl, tetrahydropyranyl, tetrahydrofuranyl, piperidinyl, pyrrolidinyl, oxazolinyl and the like.

"Substituted heterocycloalkyl" refers to heterocycloalkyl as just described including in which one or more hydrogen atom to any atom of the heterocycloalkyl is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heterocycloalkyl radicals include, for example, N-methylpiperazinyl, 3-dimethylaminomorpholinyl and the like.

The term "aryl" is used herein to refer to an aromatic substituent which may be a single aromatic ring or multiple aromatic rings which are fused together, linked covalently, or linked to a common group such as a methylene or ethylene moiety. The aromatic ring(s) may include phenyl, naphthyl, anthracenyl, and biphenyl, among others. In particular embodiments, aryls have between 1 and 200 carbon atoms, between 1 and 50 carbon atoms or between 1 and 20 carbon atoms.

"Substituted aryl" refers to aryl as just described in which one or more hydrogen atom bound to any carbon is replaced by one or more functional groups such as alkyl, substituted alkyl, cycloalkyl, substituted cycloalkyl, heterocycloalkyl, substituted heterocycloalkyl, halogen, alkylhalos (e.g., $CF_3$), hydroxy, amino, phosphido, alkoxy, amino, thio, nitro, and both saturated and unsaturated cyclic hydrocarbons which are fused to the aromatic ring(s), linked covalently or linked to a common group such as a methylene or ethylene moiety. The common linking group may also be a carbonyl as in benzophenone or oxygen as in diphenylether or nitrogen in diphenylamine.

The term "heteroaryl" as used herein refers to aromatic or unsaturated rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, pyrazole, pyrrole, furan, etc. or benzo-fused analogues of these rings are defined by the term "heteroaryl."

"Substituted heteroaryl" refers to heteroaryl as just described including in which one or more hydrogen atoms bound to any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl radicals include, for example, 4-N,N-dimethylaminopyridine.

The term "alkoxy" is used herein to refer to the $-OZ^1$ radical, where $Z^1$ is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" refers to the —SiZ$^1$Z$^2$Z$^3$ radical, where each of Z$^1$, Z$^2$, and Z$^3$ is independently selected from the group consisting of hydrogen, alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" refers to the —BZ$^1$Z$^2$ group, where each of Z$^1$ and Z$^2$ is independently selected from the group consisting of hydrogen, alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphino" refers to the group —PZ$^1$Z$^2$, where each of Z$^1$ and Z$^2$ is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof.

As used herein, the term "phosphine" refers to the group: PZ$^1$Z$^2$Z$^3$, where each of Z$^1$, Z$^3$ and Z$^2$ is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof.

The term "amino" is used herein to refer to the group —NZ$^1$Z$^2$, where each of Z$^1$ and Z$^2$ is independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "amine" is used herein to refer to the group: NZ$^1$Z$^2$Z$^3$, where each of Z$^1$, Z$^2$ and Z$^2$ is independently selected from the group consisting of hydrogen, alkyl, substituted alkyl, cycloalkyl, substituted cycloalkyl, heterocycloalkyl, substituted heterocycloalkyl, aryl (including pyridines), substituted aryl, heteroaryl, substituted heteroaryl, alkoxy, aryloxy, silyl and combinations thereof.

The term "thio" is used herein to refer to the group —SZ$^1$, where Z$^1$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "seleno" is used herein to refer to the group —SeZ$^1$, where Z$^1$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "saturated" refers to lack of double and triple bonds between atoms of a radical group such as ethyl, cyclohexyl, pyrrolidinyl, and the like.

The term "unsaturated" refers to the presence one or more double and/or triple bonds between atoms of a radical group such as vinyl, acetylide, oxazolinyl, cyclohexenyl, acetyl and the like.

Ligands

Suitable ligands useful in the catalysts used to make the P* and P/E* polymers used in the practice of this invention can be characterized broadly as monoanionic ligands having an amine and a heteroaryl or substituted heteroaryl group. The ligands of these catalysts are referred to, for the purposes of this invention, as nonmetallocene ligands, and may be characterized by the following general formula:

(I)

wherein R$^1$ is very generally selected from the group consisting of alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl and combinations thereof. In many embodiments, R$^1$ is a ring having from 4–8 atoms in the ring generally selected from the group consisting of substituted cycloalkyl, substituted heterocycloalkyl, substituted aryl and substituted heteroaryl, such that R$^1$ may be characterized by the general formula:

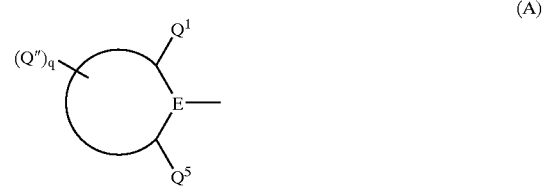

(A)

where Q$^1$ and Q$^5$ are substituents on the ring ortho to atom E, with E being selected from the group consisting of carbon and nitrogen and with at least one of Q$^1$ or Q$^5$ being bulky (defined as having at least 2 atoms). Q$^1$ and Q$^5$ are independently selected from the group consisting of alkyl, substituted alkyl, cycloalkyl, substituted cycloalkyl, aryl, substituted aryl and silyl, but provided that Q$^1$ and Q$^5$ are not both methyl. Q''$_q$ represents additional possible substituents on the ring, with q being 1, 2, 3, 4 or 5 and Q'' being selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof. T is a bridging group selected group consisting of —CR$^2$R$^3$— and —SiR$^2$R$^3$— with R$^2$ and R$^3$ being independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof. J'' is generally selected from the group consisting of heteroaryl and substituted heteroaryl, with particular embodiments for particular reactions being described herein.

In a more specific embodiment, suitable nonmetallocene ligands may be characterized by the following general formula:

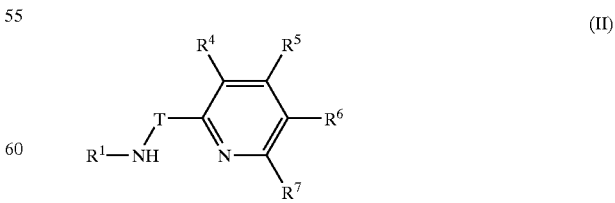

(II)

wherein R$^1$ and T are as defined above and each of R$^4$, R$^5$, R$^6$ and R$^7$ is independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, halide, nitro, and combinations thereof. Optionally, any combination of $R^1$, $R^2$, $R^3$ and $R^4$ may be joined together in a ring structure.

In certain more specific embodiments, the ligands may be characterized by the following general formula:

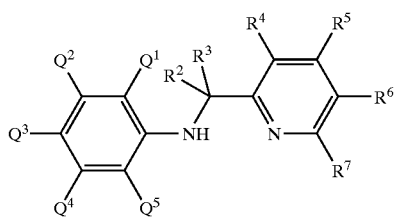

(III)

wherein $Q^1$, $Q^5$, $R^2$, $R^3$, $R^4$, $R^5$, $R^6$ and $R^7$ are as defined above. $Q^2$, $Q^3$ and $Q^4$ are independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, nitro, and combinations thereof.

In other more specific embodiments, the suitable ligands may be characterized by the following general formula:

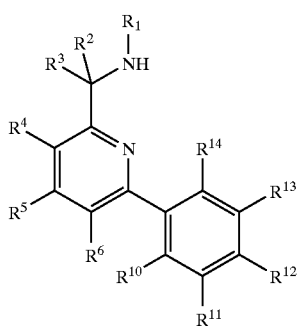

(IV)

wherein $R^1$, $R^2$, $R^3$, $R^4$, $R^5$, and $R^6$ are as defined above. In this embodiment the $R^7$ substituent has been replaced with an aryl or substituted aryl group, with $R^{10}$, $R^{11}$, $R^{12}$ and $R^{13}$ being independently selected from the group consisting of hydrogen, halo, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxy, aryloxy, silyl, boryl, phosphino, amino, thio, seleno, nitro, and combinations thereof, optionally, two or more $R^{10}$, $R^{11}$, $R^{12}$ and $R^{13}$ groups may be joined to form a fused ring system having from 3–50 non-hydrogen atoms. $R^{14}$ is selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxy, aryloxy, silyl, boryl, phosphino, amino, thio, seleno, halide, nitro, and combinations thereof.

In still more specific embodiments, the ligands may be characterized by the general formula:

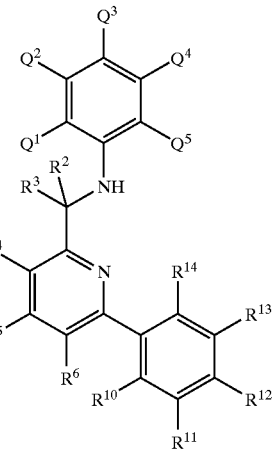

(V)

wherein $R^2$–$R^6$, $R^{10}$–$R^{14}$ and $Q^1$–$Q^5$ are all as defined above.

In certain embodiments, $R^2$ is preferably hydrogen. Also preferably, each of $R^4$ and $R^5$ is hydrogen and $R^6$ is either hydrogen or is joined to $R^7$ to form a fused ring system. Also preferred is where $R^3$ is selected from the group consisting of benzyl, phenyl, 2-biphenyl, t-butyl, 2-dimethylaminophenyl (2-($NMe_2$)—$C_6H_4$—), 2-methoxyphenyl (2-MeO—$C_6H_4$—), anthracenyl, mesityl, 2-pyridyl, 3,5-dimethylphenyl, o-tolyl, 9-phenanthrenyl. Also preferred is where $R^1$ is selected from the group consisting of mesityl, 4-isopropylphenyl (4-$Pr^i$—$C_6H_4$—), napthyl, 3,5-$(CF_3)_2$—$C_6H_3$—, 2-Me-napthyl, 2,6-$(Pr^i)_2$—$C_6H_3$—, 2-biphenyl, 2-Me-4-MeO—$C_6H_3$—; 2-$Bu^t$-$C_6H_4$—, 2,5-$(Bu^t)_2$—$C_6H_3$—, 2-$Pr^i$-6-Me-$C_6H_3$—; 2-$Bu^t$-6-Me-$C_6H_3$—, 2,6-$Et_2$-$C_6H_3$—, 2-sec-butyl-6-Et-$C_6H_3$— Also preferred is where $R^7$ is selected from the group consisting of hydrogen, phenyl, napthyl, methyl, anthracenyl, 9-phenanthrenyl, mesityl, 3,5-$(CF_3)_2$—$C_6H_3$—, 2-$CF_3$—$C_6H_4$—, 4-$CF_3$—$C_6H_4$—, 3,5-$F_2$—$C_6H_3$—, 4-F—$C_6H_4$—, 2,4-$F_2$—$C_6H_3$—, 4-($NMe_2$)—$C_6H_4$—, 3-MeO—$C_6H_4$—, 4-MeO—$C_6H_4$—, 3,5-$Me_2$-$C_6H_3$—, o-tolyl, 2,6-$F_2$—$C_6H_3$— or where $R^7$ is joined together with $R^6$ to form a fused ring system, e.g., quinoline.

Also optionally, two or more $R^4$, $R^5$, $R^6$, $R^7$ groups may be joined to form a fused ring system having from 3–50 non-hydrogen atoms in addition to the pyridine ring, e.g. generating a quinoline group. In these embodiments, $R^3$ is selected from the group consisting of aryl, substituted aryl, heteroaryl, substituted heteroaryl, primary and secondary alkyl groups, and —$PY_2$ where Y is selected from the group consisting of aryl, substituted aryl, heteroaryl, and substituted heteroaryl.

Optionally within above formulas IV and V, $R^6$ and $R^{10}$ may be joined to form a ring system having from 5–50 non-hydrogen atoms. For example, if $R^6$ and $R^{10}$ together form a methylene, the ring will have 5 atoms in the backbone of the ring, which may or may not be substituted with other atoms. Also for example, if $R^6$ and $R^{10}$ together form an ethylene, the ring will have 6 atoms in the backbone of the ring, which may or may not be substituted with other atoms. Substituents from the ring can be selected from the group consisting of halo, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxy, aryloxy, silyl, boryl, phosphino, amino, thio, seleno, nitro, and combinations thereof.

In certain embodiments, the ligands are novel compounds. One example of the novel ligand compounds, includes those compounds generally characterized by formula (III), above where $R^2$ is selected from the group consisting of hydrogen, alkyl, substituted alkyl, cycloalkyl, substituted cycloalkyl, aryl, and substituted aryl; and $R^3$ is a phosphino characterized by the formula —$PZ^1Z^2$, where each of $Z^1$ and $Z^2$ is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof. Particularly preferred embodiments of these compounds include those where $Z^1$ and $Z^2$ are each independently selected from the group consisting of alkyl, substituted alkyl, cycloalkyl, heterocycloalkyl, aryl, and substituted aryl; and more specifically phenyl; where $Q^1$, $Q^3$, and $Q^5$ are each selected from the group consisting of alkyl and substituted alkyl and each of $Q^2$ and $Q^4$ is hydrogen; and where $R^4$, $R^5$, $R^6$ and $R^7$ are each hydrogen.

The ligands may be prepared using known procedures. See, for example, Advanced Organic Chemistry, March, Wiley, New York 1992 (4$^{th}$ Ed.). Specifically, the ligands of the invention may be prepared using the two step procedure outlined in Scheme 1.

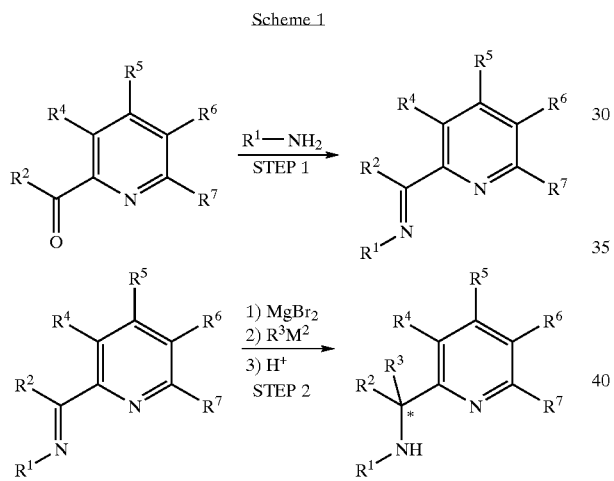

In Scheme 1, the * represents a chiral center when $R^2$ and $R^3$ are not identical; also, the R groups have the same definitions as above. Generally, $R^3M^2$ is a nucleophile such as an alkylating or arylating or hydrogenating reagent and $M^2$ is a metal such as a main group metal, or a metalloid such as boron. The alkylating, arylating or hydrogenating reagent may be a Grignard, alkyl, aryl-lithium or borohydride reagent. Scheme 1, step 2 first employs the use of complexing reagent. Preferably, as in the case of Scheme 1, magnesium bromide is used as the complexing reagent. The role of the complexing reagent is to direct the nucleophile, $R^3M^2$, selectively to the imine carbon. Where the presence of functional groups impede this synthetic approach, alternative synthetic strategies may be employed. For instance, ligands where $R^3$=phosphino can be prepared in accordance with the teachings of U.S. Pat. Nos. 6,034,240 and 6,043,363. In addition, tetra-alkylhafnium compounds or tetra-substituted alkylhafnium compounds or tetra-arylhafnium compounds or tetra-substituted arylhafnium compounds may be employed in step 2, in accordance with the teachings of U.S. Pat. No. 6,103,657. Scheme 2 further describes a synthesis process:

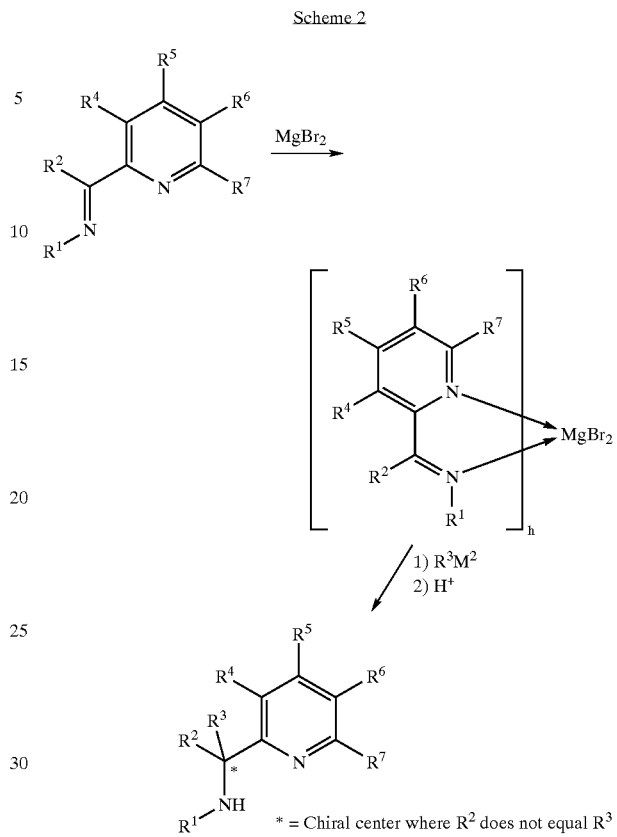

In scheme 2, h=1 or 2 and the bromine ions may or may not be bound to the magnesium. The effect of the complexation is to guide the subsequent nucleophilic attack by $R^3M^2$ to the imine carbon. As shown in Scheme 2 by the *, where $R^2$ and $R^3$ are different, this approach also leads to the formation of a chiral center on the ancillary ligands of the invention which promotes resin tacitity. Under some circumstances $R^3M^2$ may be successfully added to the imine in the absence the complexing reagent. Ancillary ligands that possess chirality may be important in certain olefin polymerization reactions, particularly those that lead to a stereospecific polymer, see "Stereospecific Olefin Polymerization with Chiral Metallocene Catalysts", Brintzinger, et al., Angew. Chem. Int. Ed. Engl., 1995, Vol. 34, pp. 1143–1170, and the references therein; Bercaw et al., J. Am. Chem. Soc., 1999, Vol. 121, 564–573; and Bercaw et al., J. Am. Chem. Soc., 1996, Vol. 118, 11988–11989.

Compositions

Once the desired ligand is formed, it may be combined with a metal atom, ion, compound or other metal precursor compound. In some applications, the ligands will be combined with a metal compound or precursor and the product of such combination is not determined, if a product forms. For example, the ligand may be added to a reaction vessel at the same time as the metal or metal precursor compound along with the reactants, activators, scavengers, etc. Additionally, the ligand can be modified prior to addition to or after the addition of the metal precursor, e.g. through a deprotonation reaction or some other modification.

For formulas I, II, III, IV and V, the metal precursor compounds may be characterized by the general formula Hf(L)$_n$ where L is independently selected from the group consisting of halide (F, Cl, Br, I), alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates, and combinations thereof. n is 1, 2, 3, 4, 5, or 6. The hafnium precursors may be monomeric, dimeric or higher orders thereof. It is well known that hafnium metal typically contains some amount of impurity of zirconium. Thus, this invention uses as pure hafnium as is commercially reasonable. Specific examples of suitable hafnium precursors include, but are not limited to $HfCl_4$, $Hf(CH_2Ph)_4$, $Hf(CH_2CMe_3)_4$, $Hf(CH_2SiMe_3)_4$, $Hf(CH_2Ph)_3Cl$, $Hf(CH_2CMe_3)_3Cl$, $Hf(CH_2SiMe_3)_3Cl$, $Hf(CH_2Ph)_2Cl_2$, $Hf(CH_2CMe_3)_2Cl_2$, $Hf(CH_2SiMe_3)_2Cl_2$, $Hf(NMe_2)_4$, $Hf(NEt_2)_4$, and $Hf(N(SiMe_3)_2)_2Cl_2$. Lewis base adducts of these examples are also suitable as hafnium precursors, for example, ethers, amines, thioethers, phosphines and the like are suitable as Lewis bases.

For formulas IV and V, the metal precursor compounds may be characterized by the general formula $M(L)_n$ where M is hafnium or zirconium and each L is independently selected from the group consisting of halide (F, Cl, Br, I), alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates, and combinations thereof. n is 4, typically. It is well known that hafnium metal typically contains some amount of impurity of zirconium. Thus, this practice uses as pure hafnium or zirconium as is commercially reasonable. Specific examples of suitable hafnium and zirconium precursors include, but are not limited to $HfCl_4$, $Hf(CH_2Ph)_4$, $Hf(CH_2CMe_3)_4$, $Hf(CH_2SiMe_3)_4$, $Hf(CH_2Ph)_3Cl$, $Hf(CH_2CMe_3)_3Cl$, $Hf(CH_2SiMe_3)_3Cl$, $Hf(CH_2Ph)_2Cl_2$, $Hf(CH_2CMe_3)_2Cl_2$, $Hf(CH_2SiMe_3)_2Cl_2$, $Hf(NMe_2)_4$, $Hf(NEt_2)_4$, and $Hf(N(SiMe_3)_2)_2Cl_2$; $ZrCl_4$, $Zr(CH_2Ph)_4$, $Zr(CH_2CMe_3)_4$, $Zr(CH_2SiMe_3)_4$, $Zr(CH_2Ph)_3Cl$, $Zr(CH_2CMe_3)_3Cl$, $Zr(CH_2SiMe_3)_3Cl$, $Zr(CH_2Ph)_2Cl_2$, $Zr(CH_2CMe_3)_2Cl_2$, $Zr(CH_2SiMe_3)_2Cl_2$, $Zr(NMe_2)_4$, $Zr(NEt_2)_4$, $Zr(NMe_2)_2Cl_2$, $Zr(NEt_2)_2Cl$, and $Zr(N(SiMe_3)_2)_2Cl_2$. Lewis base adducts of these examples are also suitable as hafnium precursors, for example, ethers, amines, thioethers, phosphines and the like are suitable as Lewis bases.

The ligand to metal precursor compound ratio is typically in the range of about 0.01:1 to about 100:1, more preferably in the range of about 0.1:1 to about 10:1.

Metal-Ligand Complexes

Generally, the ligand is mixed with a suitable metal precursor compound prior to or simultaneously with allowing the mixture to be contacted with the reactants (e.g., monomers). When the ligand is mixed with the metal precursor compound, a metal-ligand complex may be formed, which may be a catalyst or may need to be activated to be a catalyst. The metal-ligand complexes discussed herein are referred to as 2,1 complexes or 3,2 complexes, with the first number representing the number of coordinating atoms and second number representing the charge occupied on the metal. The 2,1-complexes therefore have two coordinating atoms and a single anionic charge. Other embodiments are those complexes that have a general 3,2 coordination scheme to a metal center, with 3,2 referring to a ligand that occupies three coordination sites on the metal and two of those sites being anionic and the remaining site being a neutral Lewis base type coordination.

Looking first at the 2,1-nonmetallocene metal-ligand complexes, the metal-ligand complexes may be characterized by the following general formula:

(VI)

wherein T, J″, $R^1$, L and n are as defined previously; and x is 1 or 2. The J″ heteroaryl may or may not datively bond, but is drawn as bonding. More specifically, the nonmetallocene-ligand complexes may be characterized by the formula:

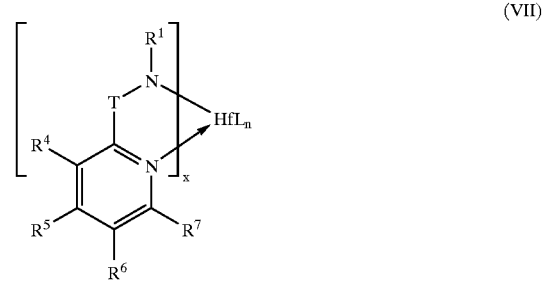

(VII)

wherein $R^1$, T, $R^4$, $R^5$, $R^6$, $R^7$, L and n are as defined previously; and x is 1 or 2. In one preferred embodiment x=1 and n=3. Additionally, Lewis base adducts of these metal-ligand complexes can also be used, for example, ethers, amines, thioethers, phosphines and the like are suitable as Lewis bases.

More specifically, the nonmetallocene metal-ligand complexes may be characterized by the general formula:

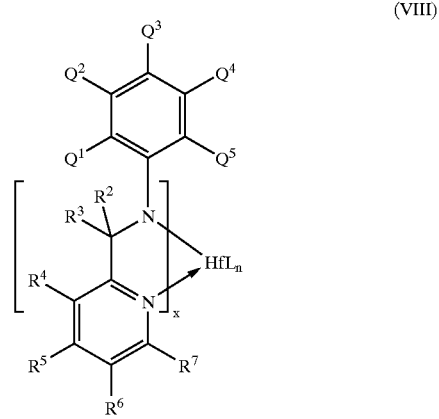

(VIII)

wherein the variables are generally defined above. Thus, e.g., $Q^2$, $Q^3$, $Q^4$, $R^2$, $R^3$, $R^4$, $R^5$, $R^6$ and $R^7$ are independently selected from the group consisting of hydrogen, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxyl, aryloxyl, silyl, boryl, phosphino, amino, thio, seleno, nitro, and combinations thereof; optionally, two or more $R^4$, $R^5$, $R^6$, $R^7$ groups may be joined to form a fused ring system having from 3–50 non-hydrogen atoms in addition to the pyridine ring, e.g. generating a quinoline group; also, optionally, any combination of $R^2$, $R^3$ and $R^4$ may be joined together in a ring structure; $Q^1$ and $Q^5$ are selected from the group consisting of alkyl, substituted alkyl, cycloalkyl, substituted cycloalkyl, aryl, substituted aryl, provided that $Q^1$ and $Q^5$ are not both methyl; and each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates and combinations thereof; n is 1,2,3,4,5, or 6; and x=1 or 2.

In other embodiments, the 2,1 metal-ligand complexes can be characterized by the general formula:

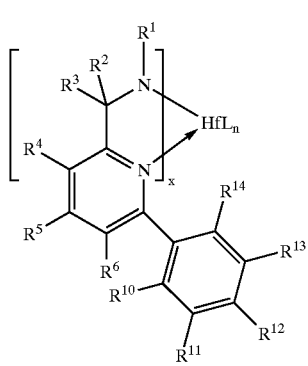
(IX)

wherein the variables are generally defined above.

In still other embodiments, the 2,1 metal-ligand complexes can be characterized by the general formula:

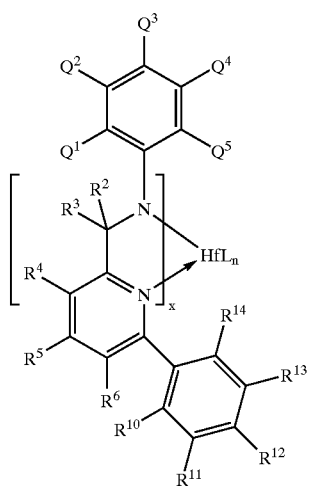
(X)

wherein the variables are generally defined above.

The more specific embodiments of the nonmetallocene metal-ligand complexes of formulas VI, VII, VIII, IX and X are explained above with regard to the specifics described for the ligands and metal precursors. Specific examples of 2,1 metal-ligand complexes include, but are not limited to:

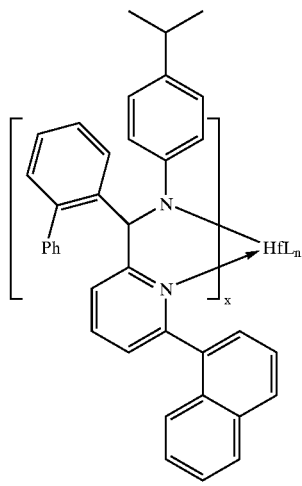

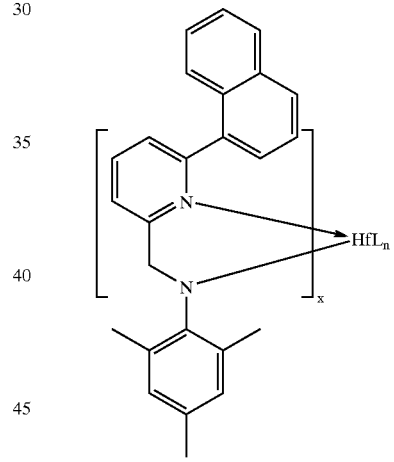

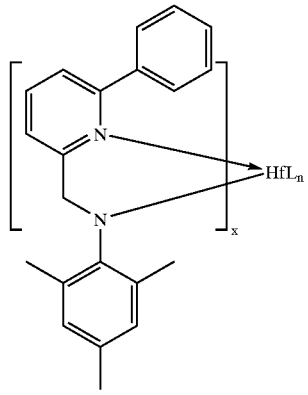

-continued
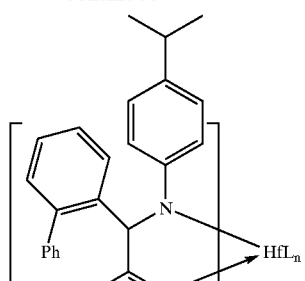
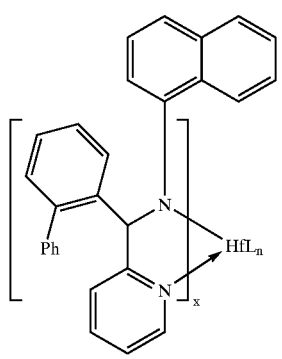
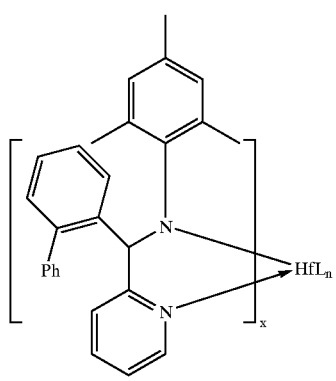
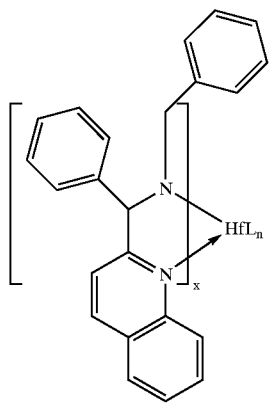
-continued
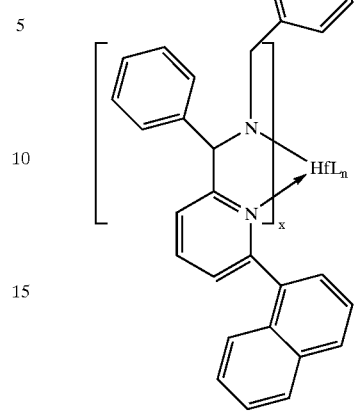
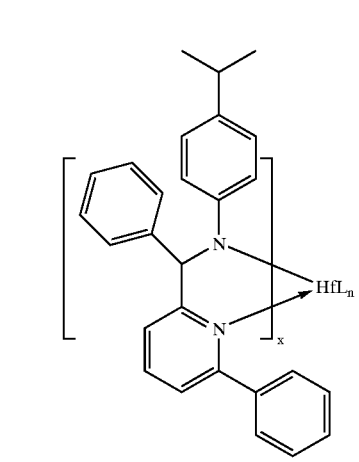
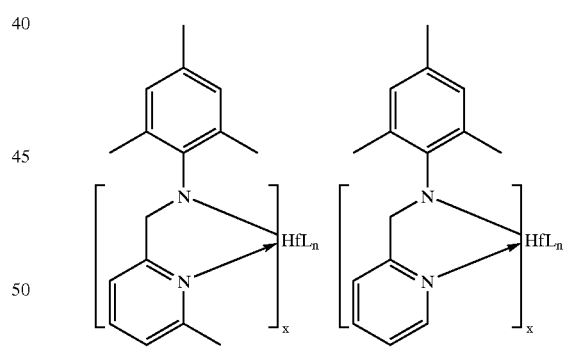
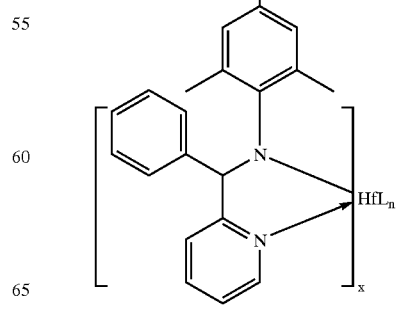

-continued

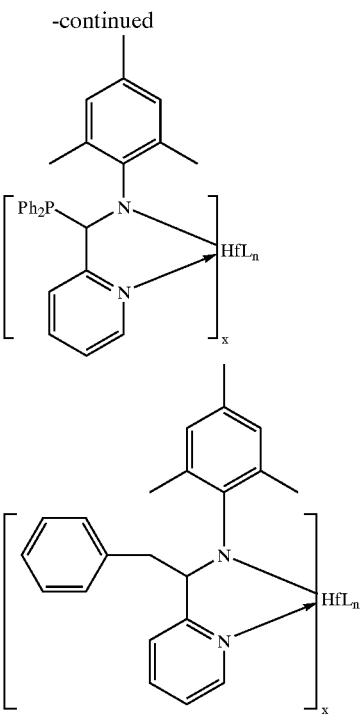

where L, n and x are defined as above (e.g., x=1 or 2) and Ph=phenyl. In preferred embodiments, x=1 and n=3. Furthermore in preferred embodiments, L is selected from the group consisting of alkyl, substituted alkyl, aryl, substituted aryl or amino.

Turning to the 3,2 metal-ligand nonmetallocene complexes, the metal-ligand complexes may be characterized by the general formula:

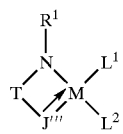
(XI)

where M is zirconium or hafnium;

$R^1$ and T are defined above;

J''' being selected from the group of substituted heteroaryls with 2 atoms bonded to the metal M, at least one of those 2 atoms being a heteroatom, and with one atom of J''' is bonded to M via a dative bond, the other through a covalent bond; and $L^1$ and $L^2$ are independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, carboxylates, thio, 1,3-dionates, oxalates, carbonates, nitrates, sulphates, and combinations thereof.

More specifically, the 3,2 metal-ligand nonmetallocene complexes may be characterized by the general formula:

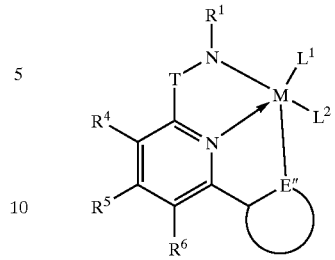
(XII)

where M is zirconium or hafnium;

T, $R^1$, $R^4$, $R^5$, $R^6$, $L^1$ and $L^2$ are defined above; and

E'' is either carbon or nitrogen and is part of an cyclic aryl, substituted aryl, heteroaryl, or substituted heteroaryl group.

Even more specifically, the 3,2 metal-ligand nonmetallocene complexes may be characterized by the general formula:

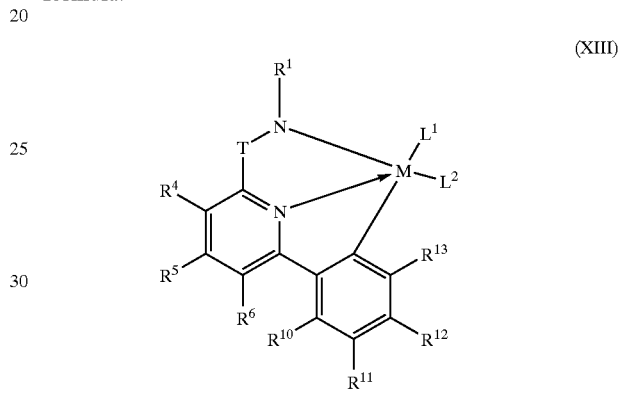
(XIII)

where M is zirconium or hafnium; and

T, $R^1$, $R^4$, $R^5$, $R^6$, $R^{10}$, $R^{11}$, $R^{12}$, $R^{13}$, $L^1$ and $L^2$ are defined above.

Still even more specifically, the 3,2 metal-ligand nonmetallocene complexes may be characterized by the general formula:

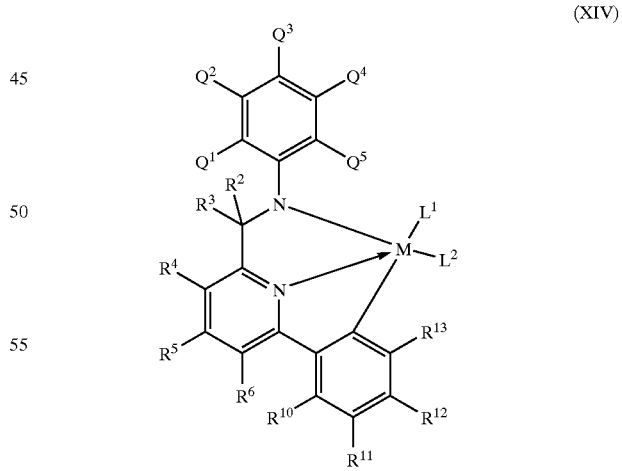
(XIV)

where M is zirconium or hafnium; and

T, $R^1$, $R^4$, $R^5$, $R^6$, $R^{10}$, $R^{11}$, $R^{12}$, $R^{13}$, $Q^1$, $Q^2$, $Q^3$, $Q^4$, $Q^5$, $L^1$ and $L^2$ are defined above.

The more specific embodiments of the metal-ligand complexes of formulas XI, XII, XIII and XIV are explained above with regard to the specifics described for the ligands and metal precursors.

In the above formulas, $R^{10}$, $R^{11}$, $R^{12}$ and $R^{13}$ are independently selected from the group consisting of hydrogen, halo, alkyl, substituted alkyl, cycloalkyl, substituted cycloalkyl, heteroalkyl, substituted heteroalkyl, heterocycloalkyl, substituted hetercycloalkyl, aryl, substituted aryl, heteroaryl, substituted heteroaryl, alkoxy, aryloxy, silyl, boryl, phosphino, amino, thio, seleno, nitro, and combinations thereof; optionally, two or more $R^{10}$, $R^{11}$, $R^{12}$ and $R^{13}$ groups may be joined to form a fused ring system having from 3–50 non-hydrogen atoms.

In addition, Lewis base adducts of the metal-ligand complexes in the above formulas are also suitable, for example, ethers, amines, thioethers, phosphines and the like are suitable as Lewis bases.

The metal-ligand complexes can be formed by techniques known to those of skill in the art. In some embodiments, $R^{14}$ is hydrogen and the metal-ligand complexes are formed by a metallation reaction (in situ or not) as shown below in scheme 3:

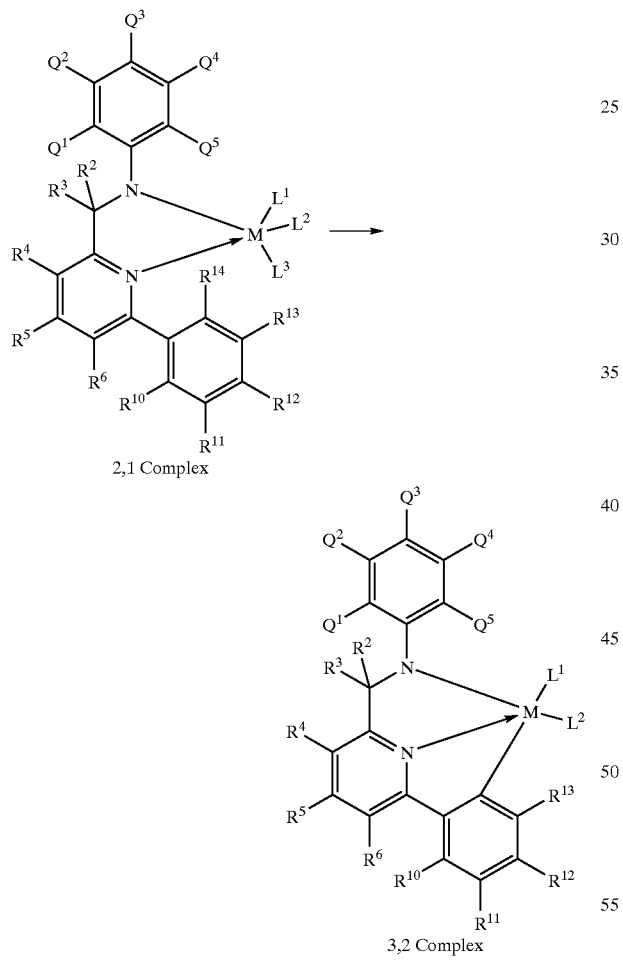

2,1 Complex 3,2 Complex

Scheme 3

In scheme 3, $R^{14}$ is hydrogen (but see above for the full definition of $R^{14}$ in other embodiments). The metallation reaction to convert the 2,1-complex on the left to the 3,2 complex on the right can occur via a number of mechanisms, likely depending on the substituents chosen for $L^1$, $L^2$ and $L^3$ and the other substituents such as $Q^1$–$Q^5$, $R^2$–$R^6$, $R^{10}$ to $R^{13}$. In one embodiment, when $L^1$, $L^2$ and $L^3$ are each $N(CH_3)_2$, the reaction can proceed by heating the 2,1 complex to a temperature above about 100° C. In this embodiment, it is believed that $L^1$ and $L^2$ remain $N(CH_3)_2$ in the 3,2 complex. In another embodiment where $L^1$, $L^2$ and $L^3$ are each $N(CH_3)_2$, the reaction can proceed by adding a group 13 reagent (as described below) to the 2,1 complex at a suitable temperature (such as room temperature). Preferably the group 13 reagent for this purpose is di-isobutyl aluminum hydride, tri-isobutyl aluminum or trimethyl aluminum. In this embodiment, $L^1$ and $L^2$ are typically converted to the ligand (e.g., alkyl or hydride) stemming from the group 13 reagent (e.g., from trimethyl aluminum, $L^1$ and $L^2$ are each $CH_3$ in the 3,2 complex). The 2,1 complex in scheme 3 is formed by the methods discussed above.

In an alternative embodiment possibly outside the scope of scheme 3, for isotactic polypropylene production, it is currently preferred that $R^{14}$ is either hydrogen or methyl.

Specific examples of 3,2 complexes include:

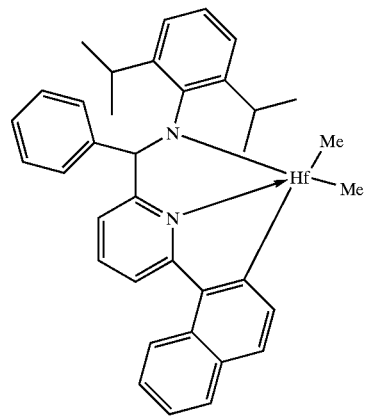

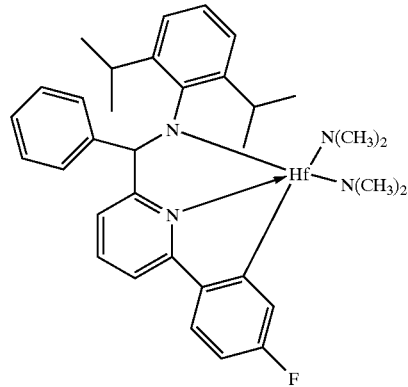

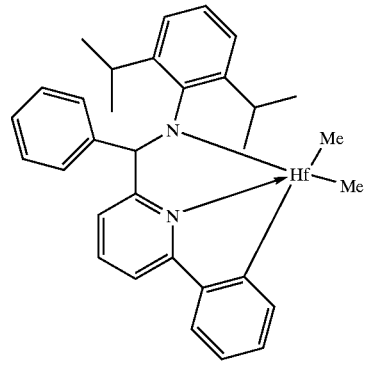

-continued

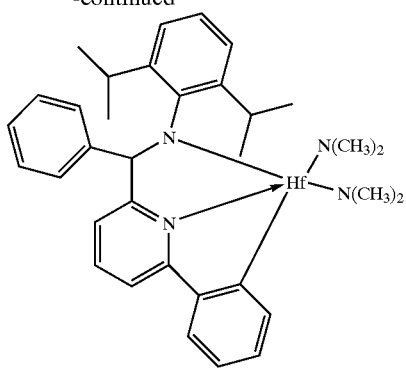

Various references disclose metal complexes that may appear to be similar; see for example, U.S. Pat. Nos. 6,103,657 and 5,637,660. However, certain embodiments herein provide unexpectedly improved polymerization performance (e.g., higher activity and/or higher polymerization temperatures and/or higher comonomer incorporation and/or crystalline polymers resulting from a high degree of stereoselectivity during polymerization) relative to the embodiments disclosed in those references. In particular, as shown in certain of the examples herein, the activity of the hafnium metal catalysts is far superior to that of the zirconium catalysts.

The ligands, complexes or catalysts may be supported on an organic or inorganic support. Suitable supports include silicas, aluminas, clays, zeolites, magnesium chloride, polyethylene glycols, polystyrenes, polyesters, polyamides, peptides and the like. Polymeric supports may be cross-linked or not. Similarly, the ligands, complexes or catalysts may be supported on similar supports known to those of skill in the art. In addition, the catalysts may be combined with other catalysts in a single reactor and/or employed in a series of reactors (parallel or serial) in order to form blends of polymer products. Supported catalysts typically produce P/E* copolymers with an MWD larger than those produce from unsupported catalysts, although these MWDs are typically less about 6, preferably less than about 5 and more preferably less than about 4.

The metal complexes are rendered catalytically active by combination with an activating cocatalyst or by use of an activating technique. Suitable activating cocatalysts include neutral Lewis acids such as alumoxane (modified and unmodified), $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: U.S. Pat. Nos. 5,153,157, 5,064,802, 5,721,185 and 5,350,723, and EP-A-277,003 and -A-468,651 (equivalent to U.S. Ser. No. 07/547,718).

The alumoxane used as an activating cocatalyst is of the formula $(R^4_x(CH_3)_yAlO)_n$, in which $R^4$ is a linear, branched or cyclic $C_1$ to $C_6$ hydrocarbyl, x is from 0 to about 1, y is from about 1 to 0, and n is an integer from about 3 to about 25, inclusive. The preferred alumoxane components, referred to as modified methylaluminoxanes, are those wherein $R^4$ is a linear, branched or cyclic $C_3$ to $C_9$ hydrocarbyl, x is from about 0.15 to about 0.50, y is from about 0.85 to about 0.5 and n is an integer between 4 and 20, inclusive; still more preferably, $R^4$ is isobutyl, tertiary butyl or n-octyl, x is from about 0.2 to about 0.4, y is from about 0.8 to about 0.6 and n is an integer between 4 and 15, inclusive. Mixtures of the above alumoxanes may also be employed.

Most preferably, the alumoxane is of the formula $(R^4_x(CH_3)_yAlO)_n$, wherein $R^4$ is isobutyl or tertiary butyl, x is about 0.25, y is about 0.75 and n is from about 6 to about 8.

Particularly preferred alumoxanes are so-called modified alumoxanes, preferably modified methylalumoxanes (MMAO), that are completely soluble in alkane solvents, for example heptane, and may include very little, if any, trialkylaluminum. A technique for preparing such modified alumoxanes is disclosed in U.S. Pat. No. 5,041,584 (which is incorporated by reference). Alumoxanes useful as an activating cocatalyst may also be made as disclosed in U.S. Pat. Nos. 4,542,199; 4,544,762; 4,960,878; 5,015,749; 5,041,583 and 5,041,585. Various alumoxanes can be obtained from commercial sources, for example, Akzo-Nobel Corporation, and include MMAO-3A, MMAO-12, and PMAO-IP.

Combinations of neutral Lewis acids, especially the combination of a trialkyl aluminum compound having from 1 to 4 carbons in each alkyl group and a halogenated tri(hydrocarbyl)boron compound having from 1 to 10 carbons in each hydrocarbyl group, especially tris(pentafluorophenyl)borane, and combinations of neutral Lewis acids, especially tris(pentafluorophenyl)borane, with nonpolymeric, compatible noncoordinating ion-forming compounds are also useful activating cocatalysts.

Suitable ion forming compounds useful as cocatalysts comprise a cation which is a Bronsted acid capable of donating a proton, and a compatible, noncoordinating anion, $A^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon.

Compounds containing anions which comprise coordination complexes containing a single metal or metalloid atom are, of course, well known and many, particularly such compounds containing a single boron atom in the anion portion, are available commercially.

In one embodiment, the activating cocatalysts may be represented by the following general formula:

$$[L^*-H]^+_d[A^{d-}]$$

wherein:
L* is a neutral Lewis base;
[L*-H]+ is a Bronsted acid;
$A^{d-}$ is a noncoordinating, compatible anion having a charge of d−, and
d is an integer from 1 to 3.

More preferably $A^{d-}$ corresponds to the formula: $[M'^{k+}Q_{n'}]^{d-}$ wherein:
k is an integer from 1 to 3;
n' is an integer from 2 to 6;
n'−k=d;
M' is an element selected from Group 13 of the Periodic Table of the Elements; and
Q independently each occurrence is selected from hydride, dialkylamido, halide, hydrocarbyl, hydrocarbyloxy, halosubstituted-hydrocarbyl, halosubstituted hydrocarbyloxy, and halo substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, i.e., the counter ion has a single negative charge and is A−. Activating cocatalysts comprising boron which are particularly useful in the preparation of the catalysts may be represented by the following general formula:

$$[L^*-H]^+[BQ_4]^-$$

wherein:
[L*-H]+ is as previously defined;
B is boron in an oxidation state of 3; and
Q is a hydrocarbyl-, hydrocarbyloxy-, fluorinated hydrocarbyl-, fluorinated hydrocarbyloxy- or fluorinated silylhydrocarbyl-group of up to 20 nonhydrogen atoms, with the proviso that in not more than one occasion is Q hydrocarbyl. Most preferably, Q is each occurrence a fluorinated aryl group, especially, a pentafluorophenyl group.

Illustrative, but not limiting, examples of boron compounds which may be used as an activating cocatalyst in the preparation of the catalysts are tri-substituted ammonium salts such as:
triethylammonium tetraphenylborate,
N,N-dimethylanilinium tetraphenylborate,
tripropylammonium tetrakis(pentafluorophenyl)borate,
N,N-dimethylanilinium n-butyltris(pentafluorophenyl)borate,
triethylammonium tetrakis(2,3,4,6-tetrafluorophenyl)borate,
N,N-diethylanilinium tetrakis(2,3,4,6-tetrafluorophenyl)borate, and
N,N-dimethyl-2,4,6-trimethylanilinium tetrakis(2,3,4,6-tetrafluorophenyl)borate;
dialkyl ammonium salts such as:
di-(i-propyl)ammonium tetrakis(pentafluorophenyl)borate, and
dicyclohexylammonium tetrakis(pentafluorophenyl)borate;
tri-substituted phosphonium salts such as:
triphenylphosphonium tetrakis(pentafluorophenyl)borate,
tri(o-tolyl)phosphonium tetrakis(pentafluorophenyl)borate, and
tri(2,6-dimethylphenyl)phosphonium tetrakis(pentafluorophenyl)borate;
di-substituted oxonium salts such as:
diphenyloxonium tetrakis(pentafluorophenyl)borate,
di(o-tolyl)oxonium tetrakis(pentafluorophenyl)borate, and
di(2,6-dimethylphenyl)oxonium tetrakis(pentafluorophenyl)borate;
di-substituted sulfonium salts such as:
diphenylsulfonium tetrakis(pentafluorophenyl)borate,
di(o-tolyl)sulfonium tetrakis(pentafluorophenyl)borate, and
di(2,6-dimethylphenyl)sulfonium tetrakis(pentafluorophenyl)borate.

Preferred [L*-H]+ cations are N,N-dimethylanilinium and tributylammonium.

Another suitable ion forming, activating cocatalyst comprises a salt of a cationic oxidizing agent and a noncoordinating, compatible anion represented by the formula:

$$(Ox^{e+})_d(A^{d-})_e$$

wherein:
$Ox^{e+}$ is a cationic oxidizing agent having a charge of e+;
e is an integer from 1 to 3; and
$A^{d-}$ and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis(pentafluorophenyl)borate.

Another suitable ion forming, activating cocatalyst comprises a compound which is a salt of a carbenium ion and a noncoordinating, compatible anion represented by the formula:

$$©^+A^-$$

wherein:
©+ is a $C_{1-20}$ carbenium ion; and
A− is as previously defined.

A preferred carbenium ion is the trityl cation, i.e., triphenylmethylium.

A further suitable ion forming, activating cocatalyst comprises a compound which is a salt of a silylium ion and a noncoordinating, compatible anion represented by the formula:

$$R_3Si(X')_q^+A^-$$

wherein:
R is $C_{1-10}$ hydrocarbyl, and X', q and A− are as previously defined.

Preferred silylium salt activating cocatalysts are trimethylsilylium tetrakis(pentafluorophenyl)borate, triethylsilylium (tetrakispentafluoro)phenylborate and ether substituted adducts thereof. Silylium salts have been previously generically disclosed in *J. Chem Soc. Chem. Comm.*, 1993, 383–384, as well as Lambert, J. B., et al., *Organometallics*, 1994, 13, 2430–2443.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

The metal complexes can also be activated by technique of bulk electrolysis which involves the electrochemical oxidation of the metal complex under electrolysis conditions in the presence of a supporting electrolyte comprising a noncoordinating, inert anion. A further discovered electrochemical technique for generation of activating cocatalysts is the electrolysis of a disilane compound in the presence of a source of a noncoordinating compatible anion. This technique is more fully disclosed and claimed in U.S. Pat. No. 5,625,087.

The foregoing activating techniques and ion forming cocatalysts are also preferably used in combination with a tri(hydrocarbyl)aluminum or tri(hydrocarbyl)borane compound having from 1 to 4 carbons in each hydrocarbyl group.

The molar ratio of catalyst/cocatalyst employed preferably ranges from 1:10,000 to 100:1, more preferably from 1:5000 to 10:1, most preferably from 1:100 to 1:1. In one embodiment the cocatalyst can be used in combination with a tri(hydrocarbyl)aluminum compound having from 1 to 10 carbons in each hydrocarbyl group. Mixtures of activating cocatalysts may also be employed. It is possible to employ these aluminum compounds for their beneficial ability to scavenge impurities such as oxygen, water, and aldehydes from the polymerization mixture. Preferred aluminum compounds include trialkyl aluminum compounds having from 1 to 6 carbons in each alkyl group, especially those wherein the alkyl groups are methyl, ethyl, propyl, isopropyl, n-butyl, isobutyl, pentyl, neopentyl or isopentyl. The molar ratio of metal complex to aluminum compound is preferably from 1:10,000 to 100:1, more preferably from 1:1000 to 10:1, most preferably from 1:500 to 1:1. A most preferred borane activating cocatalyst comprises a strong Lewis acid, especially tris(pentafluorophenyl)borane.

In some embodiments, two or more different catalysts, including the use of mixed catalysts can be employed. In addition to a nonmetallocene, metal-centered, heteroaryl ligand catalyst, when a plurality of catalysts are used, any catalyst which is capable of copolymerizing one or more olefin monomers to make an interpolymer or homopolymer may be used in embodiments of the invention in conjunction with a nonmetallocene, metal-centered, heteroaryl ligand catalyst. For certain embodiments, additional selection criteria, such as molecular weight capability and/or comonomer incorporation capability, preferably should be satisfied. Two or more nonmetallocene, metal-centered, heteroaryl ligand catalysts having different substituents can be used in the practice of certain of the embodiments disclosed herein. Suitable catalysts which may be used in conjunction with the nonmetallocene, metal-centered, heteroaryl ligand catalysts disclosed herein include, but are not limited to, Ziegler-Natta, metallocene and constrained geometry catalysts and variations on one or more of these. They include any known and presently unknown catalysts for olefin polymerization. It should be understood that the term "catalyst" as used herein refers to a metal-containing compound which is used, along with an activating cocatalyst, to form a catalyst system. The catalyst, as used herein, is usually catalytically inactive in the absence of a cocatalyst or other activating technique. However, not all suitable catalysts are catalytically inactive without a cocatalyst.

One suitable class of catalysts is the constrained geometry catalysts disclosed in U.S. Pat. Nos. 5,064,802, 5,132,380, 5,703,187 and 6,034,021; EP 0 468 651 and 0 514 828; and WO 93/19104 and 95/00526. Another suitable class of catalysts is the metallocene catalysts disclosed in U.S. Pat. Nos. 5,044,438, 5,057,475, 5,096,867 and 5,324,800. The constrained geometry catalysts may be considered as metallocene catalysts, and both are sometimes referred to in the art as single-site catalysts.

Another suitable class of catalysts is substituted indenyl containing metal complexes as disclosed in U.S. Pat. Nos. 5,965,756 and 6,015,868. Other catalysts are disclosed in U.S. Pat. Nos. 6,268,444, 6,515,155 and U.S. Ser. Nos. 60/215,456, 60/170,175 and 60/393,862. These catalysts tend to have the capability of producing higher molecular weight polymers. Yet other catalysts, cocatalysts, catalyst systems, and activating techniques which may be used include those disclosed in WO 96/23010, 99/14250, 98/41529 and 97/42241; Scollard, et al., in J. Am. Chem. Soc 1996, 118, 10008–10009; EP 0 468 537 B1; WO 97/22635; EP 0 949 278 A2, 0949279A2, and 1 063 244 A2; U.S. Pat. Nos. 5,408,017, 5,767,208 and 5,907,021; WO 88/05792, 88/05793 and 93/25590; U.S. Pat. Nos. 5,599,761 and 5,218,071; WO 90/07526; U.S. Pat. Nos. 5,972,822, 6,074,977, 6,013,819, 5,296,433, 4,874,880, 5,198,401, 5,621,127, 5,703,257, 5,728,855, 5,731,253, 5,710,224, 5,883,204, 5,504,049, 5,962,714, 5,965,677 and 5,427,991; WO 93/21238, 94/03506, 93/21242, 94/00500, 96/00244 and 98/50392; Wang, et al., Organometallics 1998, 17, 3149–3151; Younkin, et al., Science 2000, 287, 460–462; Chen and Marks, Chem. Rev. 2000, 100, 1391–1434; Alt and Koppl, Chem. Rev. 2000, 100, 1205–1221; Resconi, et al., Chem. Rev. 2000, 100, 1253–1345; Ittel, et al., Chem Rev. 2000, 100, 1169–1203; Coates, Chem. Rev., 2000, 100, 1223–1251; U.S. Pat. Nos. 5,093,415, 6,303,719 and 5,874, 505; and WO 96/13530. Also useful are those catalysts, cocatalysts and catalyst systems disclosed in U.S. Pat. Nos. 6,268,444, 6,515,155, 5,965,756 and 6,150,297.

Process Descriptions

The polymers, including the P* and P/E* polymers, used in the practice of this invention can be made by any convenient process. In one embodiment, the process reagents, i.e., (i) propylene, (ii) ethylene and/or one or more unsaturated comonomers, (iii) catalyst, and, (iv) optionally, solvent and/or a molecular weight regulator (e.g., hydrogen), are fed to a single reaction vessel of any suitable design, e.g., stirred tank, loop, fluidized-bed, etc. The process reagents are contacted within the reaction vessel under appropriate conditions (e.g., solution, slurry, gas phase, suspension, high pressure) to form the desired polymer, and then the output of the reactor is recovered for post-reaction processing. All of the output from the reactor can be recovered at one time (as in the case of a single pass or batch reactor), or it can be recovered in the form of a bleed stream which forms only a part, typically a minor part, of the reaction mass (as in the case of a continuous process reactor in which an output stream is bled from the reactor at the same rate at which reagents are added to maintain the polymerization at steady-state conditions). "Reaction mass" means the contents within a reactor, typically during or subsequent to polymerization. The reaction mass includes reactants, solvent (if any), catalyst, and products and by-products. The recovered solvent and unreacted monomers can be recycled back to the reaction vessel.

The polymerization conditions at which the reactor is operated are similar to those for the polymerization of propylene using a known, conventional Ziegler-Natta catalyst. Typically, solution polymerization of propylene is performed at a polymerization temperature between about −50 to about 200, preferably between about −10 and about 150, C, and more preferably between about 20 to about 150 C and most preferably between about 80 and 150 C, and the polymerization pressure is typically between about atmospheric to about 7, preferably between about 0.2 and about 5, Mpa. If hydrogen is present, then it is usually present at a partial pressure (as measured in the gas phase portion of the polymerization) of about 0.1 kPa to about 5 Mpa, preferably between about 1 kPa to about 3 Mpa. Gas phase, suspension and other polymerization schemes will use conditions conventional for those schemes. For gas-phase or slurry-phase polymerization processes, it is desirable to perform the polymerization at a temperature below the melting point of the polymer.

For the propylene/ethylene copolymer processes described herein, optionally containing additional unsaturated monomer, the weight ratio of propylene to ethylene in the feed to the reactors is preferably in the range of 10,000:1 to 1;10, more preferably 1,000:1 to 1:1, still more preferably 500:1 to 3:1. For the propylene/$C_{4-20}$ α-olefin copolymer processes, the weight ratio of propylene to $C_{4-20}$ α-olefin in the feed preferably is in the range of 10,000:1 to 1:20, more preferably 1,000:1 to 1:1, still more preferably 1,000:1 to 3:1.

The post-reactor processing of the recover reaction mass from the polymerization vessel typically includes the deactivation of the catalyst, removal of catalyst residue, drying of the product, and the like. The recovered polymer is then ready for storage and/or use.

The P* and P/E* polymers produced in a single reaction vessel will have the desired MFR, narrow MWD, $^{13}$C NMR peaks at 14.6 and 15.7 ppm (the peaks of approximately equal intensity), high B-value (if a P/E* copolymer), and its other defining characteristics. If, however, a broader MWD is desired, e.g., a MWD of between about 2.5 and about 3.5 or even higher, without any substantial change to the other defining characteristics of the propylene copolymer, then the copolymer is preferably made in a multiple reactor system. In multiple reactor systems, MWD as broad as 15, more preferably 10, most preferably 4–8, can be prepared.

Preferably, to obtain a broad MWD, at least two of the catalysts used in a single reactor have a high weight-average molecular weight ($M_{wH}$)/low weight average molecular weight ($M_{wL}$) ratio ($M_{wH}/M_{wL}$, as defined later) in the range from about 1.5 to about 10, and the process used is a gas phase, slurry, or solution process. More preferably, at least two of the catalysts used in a single reactor have $M_{wH}/M_{wL}$ in the range from about 1.5 to about 10, and the process used is a continuous solution process, especially a continuous solution process wherein the polymer concentration in the reactor at steady state is at least 15% by weight of the reactor contents. Still more preferably, at least two of the catalysts used in a single reactor have $M_{wH}/M_{wL}$ in the range from about 1.5 to about 10, and the process used is a continuous solution process wherein the polymer concentration in the reactor at steady state is at least 18% by weight of the reactor contents. Most preferably, at least two of the catalysts used in a single reactor have $M_{wH}/M_{wL}$ in the range from about 1.5 to about 10, and the process used is a continuous solution process wherein the polymer concentration in the reactor at steady state is at least 20% by weight of the reactor contents.

In one embodiment, the monomers comprise propylene and at least one olefin selected from the group consisting of $C_4$–$C_{10}$ α-olefins, especially 1-butene, 1-hexene, and 1-octene, and the melt flow rate (MFR) of the interpolymer is preferably in the range of about 0.1 to about 500, more preferably in the range from about 0.1 to about 100, further more preferably about 0.2 to 80, most preferably in the range of 0.3–50. In some embodiments, the nonmetallocene, catalysts described herein may be utilized in combination with at least one additional homogeneous or heterogeneous polymerization catalyst in separate reactors connected in series or in parallel to prepare polymer blends having desirable properties. An example of such a process is disclosed in WO 94/00500, equivalent to U.S. Ser. No. 07/904,770, as well as U.S. Ser. No. 08/010,958, filed Jan. 29, 1993. Included in these embodiments is the use of two different nonmetallocene, metal-centered, heteroaryl ligand catalysts.

The catalyst system may be prepared as a homogeneous catalyst by addition of the requisite components to a solvent in which polymerization will be carried out by solution polymerization procedures. The catalyst system may also be prepared and employed as a heterogeneous catalyst by adsorbing the requisite components on a catalyst support material such as silica gel, alumina or other suitable inorganic support material. When prepared in heterogeneous or supported form, it is preferred to use silica as the support material. The heterogeneous form of the catalyst system may be employed in a slurry or gas phase polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise the α-olefin comonomer or a mixture of different α-olefin comonomers may be used in whole or part as the diluent. Most preferably, the major part of the diluent comprises at least the α-olefin monomer or monomers to be polymerized.

Solution polymerization conditions utilize a solvent for the respective components of the reaction. Preferred solvents include, but are not limited to, mineral oils and the various hydrocarbons which are liquid at reaction temperatures and pressures. Illustrative examples of useful solvents include, but are not limited to, alkanes such as pentane, iso-pentane, hexane, heptane, octane and nonane, as well as mixtures of alkanes including kerosene and Isopar E™, available from Exxon Chemicals Inc.; cycloalkanes such as cyclopentane, cyclohexane, and methylcyclohexane; and aromatics such as benzene, toluene, xylenes, ethylbenzene and diethylbenzene.

The polymerization may be carried out as a batch or a continuous polymerization process. A continuous process is preferred, in which event catalysts, solvent or diluent (if employed), and comonomers (or monomer) are continuously supplied to the reaction zone and polymer product continuously removed therefrom. The polymerization conditions for manufacturing the interpolymers are generally those useful in the solution polymerization process, although the application is not limited thereto. Gas phase and slurry polymerization processes are also believed to be useful, provided the proper catalysts and polymerization conditions are employed.

The following procedure may be carried out to obtain a P/E* copolymer. In a stirred-tank reactor propylene monomer is introduced continuously together with solvent, and ethylene monomer. The reactor contains a liquid phase composed substantially of ethylene and propylene monomers together with any solvent or additional diluent. If desired, a small amount of a "H"-branch inducing diene such as norbornadiene, 1,7-octadiene or 1,9-decadiene may also be added. A nonmetallocene, metal-centered, heteroaryl ligand catalyst and suitable cocatalyst are continuously introduced in the reactor liquid phase. The reactor temperature and pressure may be controlled by adjusting the solvent/ monomer ratio, the catalyst addition rate, as well as by cooling or heating coils, jackets or both. The polymerization rate is controlled by the rate of catalyst addition. The ethylene content of the polymer product is determined by the ratio of ethylene to propylene in the reactor, which is controlled by manipulating the respective feed rates of these components to the reactor. The polymer product molecular weight is controlled, optionally, by controlling other polymerization variables such as the temperature, monomer concentration, or by a stream of hydrogen introduced to the reactor, as is known in the art. The reactor effluent is contacted with a catalyst kill agent, such as water. The polymer solution is optionally heated, and the polymer product is recovered by flashing off unreacted gaseous ethylene and propylene as well as residual solvent or diluent at reduced pressure, and, if necessary, conducting further devolatilization in equipment such as a devolatilizing extruder or other devolatilizing equipment operated at reduced pressure. For a solution polymerization process, especially a continuous solution polymerization, preferred ranges of propylene concentration at steady state are from about 0.05 weight percent of the total reactor contents to about 50 weight percent of the total reactor contents, more preferably from about 0.5 weight percent of the total reactor contents to about 30 weight percent of the total reactor contents, and most preferably from about 1 weight percent of the total reactor contents to about 25 weight percent of the total reactor contents. The preferred range of polymer concentration (otherwise known as % solids) is from about 3% of the reactor contents by weight to about 45% of the reactor contents or higher, more preferably from about 10% of the reactor contents to about 40% of the reactor contents, and most preferably from about 15% of the reactor contents to about 40% of the reactor contents.

In a continuous process, the mean residence time of the catalyst and polymer in the reactor generally is from 5 minutes to 8 hours, and preferably from 10 minutes to 6 hours, more preferably from 10 minutes to 1 hour.

In some embodiments, ethylene is added to the reaction vessel in an amount to maintain a differential pressure in excess of the combined vapor pressure of the propylene and diene monomers. The ethylene content of the polymer is determined by the ratio of ethylene differential pressure to the total reactor pressure. Generally the polymerization process is carried out with a pressure of ethylene of from 10 to 1000 psi (70 to 7000 kPa), most preferably from 40 to 800 psi (30 to 600 kPa). The polymerization is generally conducted at a temperature of from 25 to 250° C., preferably from 75 to 200° C., and most preferably from greater than 95 to 200° C.

In another embodiment, a process for producing a propylene homopolymer or interpolymer of propylene with at least one additional olefinic monomer selected from ethylene or $C_{4-20}$ $\alpha$-olefins comprises the following steps: 1) providing controlled addition of a nonmetallocene, metal-centered, heteroaryl ligand catalyst to a reactor, including a cocatalyst and optionally a scavenger component; 2) continuously feeding propylene and optionally one or more additional olefinic monomers independently selected from ethylene or $C_{4-20}$ $\alpha$-olefins into the reactor, optionally with a solvent or diluent, and optionally with a controlled amount of $H_2$; and 3) recovering the polymer product. Preferably, the process is a continuous solution process. The cocatalysts and optional scavenger components in the novel process can be independently mixed with the catalyst component before introduction into the reactor, or they may each independently be fed into the reactor using separate streams, resulting in "in reactor" activation. Scavenger components are known in the art and include, but are not limited to, alkyl aluminum compounds, including alumoxanes. Examples of scavengers include, but are not limited to, trimethyl aluminum, triethyl aluminum, triisobutyl aluminum, trioctyl aluminum, methylalumoxane (MAO), and other alumoxanes including, but not limited to, MMAO-3A, MMAO-7, PMAO-IP (all available from Akzo Nobel).

As previously noted, the process described above may optionally use more than one reactor. The use of a second reactor is especially useful in those embodiments in which an additional catalyst, especially a Ziegler-Natta or chrome catalyst, or a metallocene catalyst, especially a CGC, is employed. The second reactor typically holds the additional catalyst.

By proper selection of process conditions, including catalyst selection, polymers with tailored properties can be produced. For a solution polymerization process, especially a continuous solution polymerization, preferred ranges of ethylene concentration at steady state are from less than about 0.02 weight percent of the total reactor contents to about 5 weight percent of the total reactor contents, and the preferred range of polymer concentration is from about 10% of the reactor contents by weight to about 45% of the reactor contents or higher.

In general, catalyst efficiency (expressed in terms of gram of polymer produced per gram of transition metal) decreases with increasing temperature and decreasing ethylene concentration. In addition, the molecular weight of the polymer product generally decreases with increasing reactor temperature and decreases with decreasing propylene and ethylene concentration. The molecular weight of the polyolefin can also be controlled with the addition of chain transfer compounds, especially through the addition of $H_2$.

The gas phase processes are continuous processes which provide for the continuous supply of reactants to the reaction zone of the reactor and the removal of products from the reaction zone of the reactor, thereby providing a steady-state environment on the macro scale in the reaction zone of the reactor. Products are readily recovered by exposure to reduced pressure and optionally elevated temperatures (devolatilization) according to known techniques. Typically, the fluidized bed of the gas phase process is operated at temperatures greater than 50° C., preferably from about 60° C. to about 110° C., more preferably from about 70° C. to about 110° C.

A number of patents and patent applications describe gas phase processes, particularly, U.S. Pat. Nos. 4,588,790; 4,543,399; 5,352,749; 5,436,304; 5,405,922; 5,462,999; 5,461,123; 5,453,471; 5,032,562; 5,028,670; 5,473,028; 5,106,804; 5,556,238; 5,541,270; 5,608,019; 5,616,661; and EP applications 659,773; 692,500; 780,404; 697,420; 628, 343; 593,083; 676,421; 683,176; 699,212; 699,213; 721, 798; 728,150; 728,151; 728,771; 728,772; 735,058; and PCT Applications WO-94/29032, WO-94/25497, WO-94/25495, WO-94/28032, WO-95/13305, WO-94/26793, WO-95/07942, WO-97/25355, WO-93/11171, WO-95/13305, and WO-95/13306.

Applications

The polymers made in accordance with embodiments of the invention have many useful applications. For example, fabricated articles made from the polymers may be prepared using all of the conventional polyolefin processing techniques. Useful film articles include cast, blown, calendered and extrusion coated (including multi-layer films, greenhouse films, shrink films including clarity shrink film, lamination film, biaxially-oriented film, extrusion coating, liners, clarity liners, overwrap film and agricultural film). Monolayer and multilayer films may be made according to the film structures and fabrication methods described in U.S. Pat. No. 5,685,128.

The films made in accordance with this invention have many utilities, including over-wrapping films such as tissue over-wraps, bundled bottled water over-wraps; clarity films such as candy bags, bread bags, envelope window films; food and specialty packaging films, such as produce bags, meat wraps, cheese wraps, etc.; pouches such as milk pouch, bags-in-box such as wine and other verical form fill and seal techniques such as those taught by Dow, DuPont and Exxon. Shrinkage films are also within the purview of the invention, and these can be made using a variety of techniques, such as double bubble films, tenter frame techniques, biaxial orientation techniques (such as that taught by Pahlke). The films of the invention can also be elastic.

With respect to blown film applications, the films comprising P* and/or P/E* polymers exhibit excellent optics, e.g., low haze and high gloss, and much better toughness (e.g., tear and dart) than traditional Ziegler-Natta catalyzed polypropylene at comparable ethylene contents. These characteristics are shown in the Figures and examples. Moreover, blown films made from P* and/or P/E* polymers exhibit excellent hot tack and heat seal properties (e.g., a broader temperature window for the former and a lower sealing temperature for the latter than comparable Ziegler-Natta catalyzed polypropylene, even when the latter has a higher ethylene content).

The P* and P/E* polymers are also useful for wire and cable coating operations, wire and cable jacketing, including low, medium and high voltage cable jacketing, semi-conductive layers used in wire and cable power applications, wire and cable insulation, especially medium and high voltage cable insulation, telecommunications cable jackets, optical fiber jackets, as well as in sheet extrusion for vacuum forming operations. In addition, the P* and P/E* polymers may be used in foams, including high strength foam, soft foam, rigid foam, cross-linked foam, high strength foam for cushioning applications, and sound insulation foam, blow molded bottles, frozen food packages; thermoforming, especially cups and plates, trays and containers; injection moulding; blow-moulding; pipe, including potable water pipe and high pressure pipe; and automotive parts. The skilled artisan will appreciate other uses for the novel polymers and compositions disclosed herein.

Useful compositions are also suitably prepared comprising the P* and/or P/E* polymers according to embodiments of the invention and at least one other natural or synthetic polymer. Preferred other polymers include, but are not limited to, thermoplastics, such as styrene-butadiene block copolymers, polystyrene (including high impact polystyrene), ethylene vinyl alcohol copolymers, ethylene acrylic acid copolymers, other olefin copolymers (especially polyethylene copolymers) and homopolymers (e.g., those made using conventional heterogeneous catalysts). Examples include polymers made by the process of U.S. Pat. No. 4,076,698, other linear or substantially linear polymers as described in U.S. Pat. No. 5,272,236, and mixtures thereof. Other substantially linear polymers and conventional HDPE and/or LDPE may also be used in the thermoplastic compositions.

In one aspect of the present invention, the P* and P/E* polymers are useful for a wide range of applications where good optical properties are beneficial. Gloss is measured according to ASTM D-1746. Haze is measured according to ASTM D-1003, and Clarity is measured according to ASTM D-2457. With the P* and P/E* polymers, films having haze of less than 10% can be produced. In addition, these polymers can also produce films having clarity of greater than 91%.

The P* and P/E* polymers, either alone or in combination with one or more other polymers (e.g., a polymer other than a P* and P/E* polymer) may be blended, if desired or necessary, with various additives such as antioxidants, ultraviolet absorbing agents, antistatic agents, nucleating agents, lubricants, flame retardants, antiblocking agents, colorants, inorganic or organic fillers or the like.

The P* and P/E* polymers can be blended with other polymers to form a film layer of the invention. Suitable polymers for blending with the P* and P/E* polymers are commercially available from a variety of suppliers and include, but are not limited to, other polyolefins such as an ethylene polymer (e.g., low density polyethylene (LDPE), ULDPE, medium density polyethylene (MDPE), LLDPE, HDPE, homogeneously branched linear ethylene polymer, substantially linear ethylene polymer, graft-modified ethylene polymer ethylene-styrene interpolymers, ethylene vinyl acetate interpolymer, ethylene acrylic acid interpolymer, ethylene ethyl acetate interpolymer, ethylene methacrylic acid interpolymer, ethylene methacrylic acid ionomer, and the like), polycarbonate, polystyrene, conventional polypropylene (e.g., homopolymer polypropylene, polypropylene copolymer, random block polypropylene interpolymer and the like), thermoplastic polyurethane, polyamide, polylactic acid interpolymer, thermoplastic block polymer (e.g. styrene butadiene copolymer, styrene butadiene styrene triblock copolymer, styrene ethylene-butylene styrene triblock copolymer and the like), polyether block copolymer (e.g., PEBAX), copolyester polymer, polyester/polyether block polymers (e.g., HYTEL), ethylene carbon monoxide interpolymer (e.g., ethylene/carbon monoxide (ECO), copolymer, ethylene/acrylic acid/carbon monoxide (EAACO) terpolymer, ethylene/methacrylic acid/carbon monoxide (EMAACO) terpolymer, ethylene/vinyl acetate/carbon monoxide (EVACO) terpolymer and styrene/carbon monoxide (SCO)), polyethylene terephthalate (PET), chlorinated polyethylene, and the like and mixtures thereof In other words, the polyolefin used in the practice of this invention can be a blend of two or more polyolefins, or a blend of one or more polyolefins with one or more polymers other than a polyolefin. If the polyolefin used in the practice of this invention is a blend of one or more polyolefins with one or more polymers other than a polyolefin, then the polyolefins comprise at least about 1, preferably at least about 50 and more preferably at least about 90, wt % of the total weight of the blend.

In one embodiment, one or more P* and P/E* polymers is blended with a conventional polypropylene polymer. Suitable conventional polypropylene polymers for use in the invention, including random propylene ethylene polymers, are available from a number of manufacturers, such as, for example, Montell Polyolefins and Exxon Chemical Company. Suitable conventional polypropylene polymers from Exxon are supplied under the designations ESCORENE and ACHIEVE.

Suitable graft-modified polymers for use in this invention are well known in the art, and include the various ethylene polymers bearing a maleic anhydride and/or another carbonyl-containing, ethylenically unsaturated organic radical. Representative graft-modified polymers are described in U.S. Pat. No. 5,883,188, such as a homogeneously branched ethylene polymer graft-modified with maleic anhydride.

Suitable polylactic acid (PLA) polymers for use in the invention are well known in the literature (e.g., see D. M.

Bigg et al., "Effect of Copolymer Ratio on the Crystallinity and Properties of Polylactic Acid Copolymers", ANTEC '96, pp. 2028–2039; WO 90/01521; EP 0 515 203A and EP 0 748 846 A2. Suitable polylactic acid polymers are supplied commercially by Cargill Dow under the designation Eco-PLA.

Suitable thermoplastic polyurethane polymers for use in the invention are commercially available from The Dow Chemical Company under the designation PELLETHANE.

Suitable polyolefin carbon monoxide interpolymers can be manufactured using well known high pressure free-radical polymerization methods. However, they may also be manufactured with the use of so-called homogeneous catalyst systems such as those described and referenced above.

Suitable free-radical initiated high pressure carbonyl-containing ethylene polymers such as ethylene acrylic acid interpolymers can be manufactured by any technique known in the art including the methods taught by Thomson and Waples in U.S. Pat. Nos. 3,520,861, 4,988,781; 4,599,392 and 5,384,373.

Suitable ethylene vinyl acetate interpolymers for use in the invention are commercially available from various suppliers, including Exxon Chemical Company and Du Pont Chemical Company.

Suitable ethylene/alkyl acrylate interpolymers are commercially available from various suppliers. Suitable ethylene/acrylic acid interpolymers are commercially available from The Dow Chemical Company under the designation PRIMACOR. Suitable ethylene/methacrylic acid interpolymers are commercially available from Du Pont Chemical Company under the designation NUCREL.

Chlorinated polyethylene (CPE), especially chlorinated substantially linear ethylene polymers, can be prepared by chlorinating polyethylene in accordance with well known techniques. Preferably, chlorinated polyethylene comprises equal to or greater than 30 weight percent chlorine. Suitable chlorinated polyethylenes for use in the invention are commercially supplied by The Dow Chemical Company under the designation TYRIN.

The P* and P/E* polymers, if elastic, can also be shaped or fabricated into elastic films, coatings, sheets, strips, tapes, ribbons and the like. The elastic film, coating and sheet of the present invention may be fabricated by any method known in the art, including blown bubble processes (e.g., simple bubble as well as biaxial orientation techniques such trapped bubble, double bubble and tenter framing), cast extrusion, injection molding processes, thermoforming processes, extrusion coating processes, profile extrusion, and sheet extrusion processes. Simple blown bubble film processes are described, for example, in The Encyclopedia of Chemical Technology, Kirk-Othmer, Third Edition, John Wiley & Sons, New York, 1981, Vol. 16, pp. 416–417 and Vol. 18, pp. 191–192. The cast extrusion method is described, for example, in Modern Plastics Mid-October 1989 Encyclopedia Issue, Volume 66, Number 11, pages 256 to 257. Injection molding, thermoforming, extrusion coating, profile extrusion, and sheet extrusion processes are described, for example, in Plastics Materials and Processes, Seymour S. Schwartz and Sidney H. Goodman, Van Nostrand Reinhold Company, New York, 1982, pp. 527–563, pp. 632–647, and pp. 596–602.

Not only can the P* and P/E* polymers be blended with one or more other polymers, but they can also be blended with various additives such as nucleating, clarifying, stiffness and/or crystallization rate agents. These agents are used in a conventional matter and in conventional amounts.

The P* and P/E* polymers can also be functionalized by adding one or more functional groups, e.g. through the use of a functionalized azide, to the polymer chain in a post-reaction operation. Optionally, the P* and P/E* polymers can be subjected to post-reaction treatments, e.g. crosslinking, vis-breaking, and the like. Vis-breaking is particularly useful in reducing the viscosity of high molecular weight polymers. These post treatments are also used in their conventional manner.

The following examples are given to illustrate various embodiments of the invention. They do not intend to limit the invention as otherwise described and claimed herein. All numerical values are approximate. When a numerical range is given, it should be understood that embodiments outside the range are still within the scope of the invention unless otherwise indicated. In the following examples, various polymers were characterized by a number of methods. Performance data of these polymers were also obtained. Most of the methods or tests were performed in accordance with an ASTM standard, if applicable, or known procedures. All parts and percentages are by weight unless otherwise indicated FIGS. 12A–J illustrate the chemical structures of various catalysts described in the following examples.

Specific Embodiments

Tetrahydrofuran (THF), diethyl ether, toluene, hexane, and ISOPAR E (obtainable from Exxon Chemicals) are used following purging with pure, dry nitrogen and passage through double columns charged with activated alumina and alumina supported mixed metal oxide catalyst (Q-5 catalyst, available from Engelhard Corp). All syntheses and handling of catalyst components are performed using rigorously dried and deoxygenated solvents under inert atmospheres of nitrogen or argon, using either glove box, high vacuum, or Schlenk techniques, unless otherwise noted. MMAO-3A, PMAO, and PMAO-IP can be purchased from Akzo-Nobel Corporation.

Synthesis of $(C_5Me_4SiMe_2N^tBu)Ti(\eta^4\text{-}1,3\text{-pentadiene})$ (Catalyst A)

Catalyst A can be synthesized according to Example 17 of U.S. Pat. No. 5,556,928.

Synthesis of dimethylsilyl(2-methyl-s-indacenyl)(t-butylamido)titanium 1,3-pentadiene (Catalyst B)

Catalyst B can be synthesized according to Example 23 of U.S. Pat. No. 5,965,756.

Synthesis of (N-(1,1-dimethylethyl)-1,1-di-p-tolyl-1-((1,2,3,3a,7a-η)-3-(1,3-dihydro-2H-isoindol-2-yl)-1H-inden-1-yl)silanaminato-(2-)-N-)dimethyltitanium (Catalyst C)

(1) Preparation of dichloro(N-(1,1-dimethylethyl)-1,1-di(p-tolyl)-1-((1,2,3,3a,7a-η)-3-(1,3-dihydro-2H-isoindol-2-yl)-1H-inden-1-yl)silanaminato-(2-)-N-)-titanium

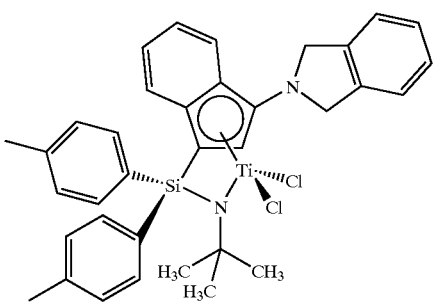

(A) Preparation of N-(tert-butyl)-N-(1,1-p-tolyl)-1-(3-(1,3-dihydro-2H-isoindol-2-yl)-1H-indenyl)silyl)amine:

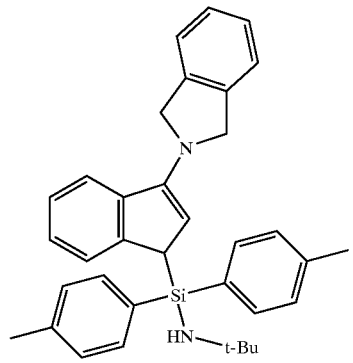

To a 1.70 g (5.35 mmol) of N-(tert-butyl)-N-(1-chloro-1,1-di(3-p-tolyl)silylamine dissolved in 20 mL of THF is added 1.279 g (5.35 mmol) of 1-(1H-3-indenyl)-1-(2,3-dihydro-1H-isoindolinyl) lithium salt dissolved in 20 mL of THF. After the addition, the reaction mixture is stirred for 9 hours and then solvent is removed under reduced pressure. The residue is extracted with 40 mL of hexane and filtered. Solvent is removed under reduced pressure giving 2.806 of product as a gray solid.

$^1$H (C$_6$D$_6$) δ: 1.10 (s, 9H), 2.01 (s, 3H), 2.08 (s, 3H), 4.12 (d, 1H, $^3J_{H-H}$=1.5 Hz), 4.39 (d, 1H, $^2J_{H-H}$=11.1 Hz), 4.57 (d, 1H, $^2J_{H-H}$=11.7 Hz), 5.55 (d, 1H, $^3J_{H-H}$=2.1 Hz), 6.9–7.22 (m, 10H), 7.56 (d, 1H, $^3J_{H-H}$=7.8 Hz), 7.62 (d, 1H, $^3J_{H-H}$=6.9 Hz), 7.67 (d, 1H, $^3J_{H-H}$=7.8 Hz), 7.83 (d, 1H, $^3J_{H-H}$=7.8 Hz).

$^{13}$C{$^1$H} (C$_6$D$_6$) δ: 21.37, 21.43, 33.78, 41.09, 50.05, 56.56, 104.28, 120.98, 122.46, 123.84, 124.71, 124.84, 126.98, 128.29, 128.52, 129.05, 132.99, 133.68, 135.08, 135.90, 136.01, 138.89, 139.05, 139.09, 141.27, 146.39, 148.48.

(B) Preparation of N-(tert-butyl)-N-(1,1-p-tolyl)-1-(3-(1,3-dihydro-2H-isoindol-2-yl)-1H-indenyl)silyl)amine, dilithium salt:

To a 50 mL hexane solution containing 2.726 g (5.61 mmol) of the N-(tert-butyl)-N-(1,1-p-tolyl)-1-(3-(1,3-dihydro-2H-isoindol-2-yl)-1H-indenyl)silyl)amine is added 7.4 mL of 1.6 M n-BuLi solution. During addition of the n-BuLi, a yellow precipitate appears. After stirring for 6 hours, the yellow precipitate is collected on a frit, washed with 2×25 mL of hexane, and dried under reduced pressure to give 2.262 g of the product as a yellow powder.

$^1$H (C$_6$D$_6$) δ: 1.17 (s, 9H), 2.30 (s, 6H), 4.51 (s, 4H), 6.21 (s, 1H), 6.47 (m, 2H), 6.97 (d, 4H, $^3J_{H-H}$=8.1 Hz), 7.15 (m, 2H), 7.23 (m, 2H), 7.50 (m, 1H), 7.81 (d, 4H, $^3J_{H-H}$=7.8 Hz), 8.07 (d, 1H, $^3J_{H-H}$=7.2 Hz). $^{13}$C{$^1$H} (C$_6$D$_6$) δ: 21.65, 38.83, 52.46, 59.82, 95.33, 112.93, 114.15, 115.78, 118.29, 122.05, 122.60, 124.16, 124.78, 126.94, 127.30, 133.06, 134.75, 137.30, 141.98, 148.17.

(C) Preparation of dichloro(N-(1,1-dimethylethyl)-1,1-di-p-tolyl-1-((1,2,3,3a,7a-η)-3-(1,3-dihydro-2H-isoindol-2-yl)-1H-inden-1-yl)silanaminato-(2-)-N-)titanium:

In the drybox 1.552 g (4.19 mmol) of TiCl$_3$(THF)$_3$ is suspended in 20 mL of THF. To this solution, 2.206 g (4.19 mmol) of N-(tert-butyl)-N-(1,1-p-tolyl)-1-(1,3-dihydro-2H-isoindol-2-yl)-1H-indenyl)silyl)amine, dilithium salt dissolved in 30 mL of THF is added within 1 minute. The solution is then stirred for 60 minutes. After this time, 0.76 g of PbCl$_2$ (2.75 mmol) is added and the solution is stirred for 60 minutes. The THF is then removed under reduced pressure. The residue is first extracted with 60 mL of methylene chloride and filtered. Solvent is removed under reduced pressure leaving a black crystalline solid. Hexane is added (30 mL) and the black suspension is stirred for 10 hour. The solids are collected on a frit, washed with 30 mL of hexane and dried under reduced pressure to give 2.23 g of the desired product as a deep purple solid.

$^1$H (THF-d$_8$) δ: 1.40 (s, 9H), 2.46 (s, 3H), 2.48 (s, 3H), 5.07 (d, 2H, $^2J_{H-H}$=12.3 Hz), 5.45 (d, 2H, $^2J_{H-H}$=12.6 Hz), 5.93 (s, 1H), 6.95 (d, 1H, $^3J_{H-H}$=9.0 Hz), 7.08 (d, 1H, $^3J_{H-H}$=7.8 Hz), 7.15–7.4 (m, 9H), 7.76 (d, 1H, $^3J_{H-H}$=7.8 Hz), 7.82 (d, 1H, $^3J_{H-H}$=7.5 Hz), 8.05 (d, 1H, $^3J_{H-H}$=8.7 Hz). $^{13}$C{$^1$H} (THF-d$_8$) δ: 21.71, 21.76, 33.38, 56.87, 61.41, 94.5, 107.95, 122.86, 125.77, 126.68, 127.84, 127.92, 128.40, 128.49, 129.36, 129.79, 131.23, 131.29, 135.79, 136.43, 136.73, 141.02, 141.22, 150.14.

(2) Preparation of (N-(1,1-dimethylethyl)-1,1-di-p-tolyl-1-((1,2,3,3a,7a-η)-3-(1,3-dihydro-2H-isoindol-2-yl)-1H-inden-1-yl)silanaminato-(2-)-N-)dimethyltitanium:

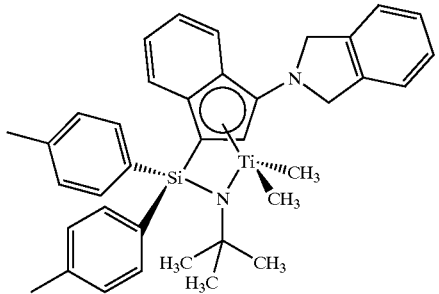

In the drybox 0.50 g of dichloro(N-(1,1-dimethylethyl)-1,1-di-p-tolyl-1-((1,2,3,3a,7a-η)-3-(1,3-dihydro-2H-isoindol-2-yl)-1H-inden-1-yl)silanaminato-(2-)-N-)titanium complex (0.79 mmol) is dissolved in 30 mL of diethyl ether. To this solution, 1.14 mL (1.6 mmol) of MeLi (1.6 M in ether) is added dropwise while stirring over a 1 minute period. After the addition of MeLi is completed, the solution is stirred for 1.5 hour. Diethyl ether is removed under reduced pressure and the residue extracted with 45 mL of hexane. Hexane is removed under reduced pressure giving a red crystalline material. This solid is dissolved in about 7 mL of toluene and 25 mL of hexane, filtered, and the solution was put into the freezer (−27° C.) for 2 days. The solvent is then decanted and the resulting crystals are washed with cold hexane and dried under reduced pressure to give 156 mg of product.

$^1$H (C$_6$D$_6$) δ: 0.25 (s, 3H), 0.99 (3H), 1.72 (s, 9H), 2.12 (s, 3H), 2.15 (s, 3H), 4.53 (d, 2H, $^2J_{H-H}$=11.7 Hz), 4.83 (d, 2H, $^2J_{H-H}$=11.7 Hz), 5.68 (s, 1H), 6.72 (dd, 1H, $^3J_{H-H}$=8.6 Hz, $^3J_{H-H}$=6.6 Hz), 6.9–7.2 (m, 11H), 7.30 (d, 1H, $^3J_{H-H}$=8.6 Hz).7.71 (d, 1H, $^3J_{H-H}$=8.5 Hz), 7.93 (d, 1H, $^3J_{H-H}$=7.8 Hz), 8.11 (d, 1H, $^3J_{H-H}$=7.8 Hz). $^{13}$C{$^1$H} (C$_6$D$_6$) δ: 21.45, 21.52, 35.30, 50.83 56.03, 56.66, 57.65, 83.80, 105.64, 122.69, 124.51, 124.56, 125.06, 125.35, 127.33, 128.98, 129.06, 129.22, 133.51, 134.02, 134.62, 136.49, 136.84, 137.69, 139.72, 139.87, 143.84.

Synthesis of (1H-cyclopenta[1]phenanthrene-2-yl) dimethyl(t-butylamido)silane titanium dimethyl (Catalyst D)

Catalyst D can be synthesized according to Example 2 of U.S. Pat. No. 6,150,297.

Synthesis of rac-[dimethylsilylbis(1-(2-methyl-4-phenyl)indenyl)]zirconium (1,4-diphenyl-1,3-butadiene) (Catalyst E)

Catalyst E can be synthesized according to Example 15 of U.S. Pat. No. 5,616,664.

Synthesis of rac-[1,2-ethanediylbis(1-indenyl)] zirconium (1,4-diphenyl-1,3-butadiene) (Catalyst F)

Catalyst F can be synthesized according to Example 11 of U.S. Pat. No. 5,616,664.

Synthesis of Catalyst G

Hafnium tetrakisdimethylamine. The reaction is prepared inside of a dry box. A 500 mL round bottom flask containing a stir bar, is charged with 200 mL of toluene and LiNMe$_2$ (21 g, 95%, 0.39 mol). HfCl$_4$ (29.9 g, 0.093 mol) is added slowly over 2 h. The temperature reaches 55° C. The mixture is stirred overnight at ambient temperature. The LiCl is filtered off. The toluene is carefully distilled away from the product. Final purification is achieved by distillation with a vacuum transfer line attached to a cold (−78° C.) receiving flask. This process is performed outside the dry box on a Schlenk line. The material is distilled over at 110–120° C. at 300–600 microns. The 19.2 g of the white solid is collected.

2-formyl-6-naphthylpyridine. Inside of a dry box, naphthylboronic acid (9.12 g, 53.0 mmol) and Na$_2$CO$_3$ (11.64 g, 110 mmol) are dissolved in 290 mL of degassed 4:1 H$_2$O/MeOH. This solution is added to a solution of 8 g (43 mmol) of 2-bromo-6-formylpyridine and 810 mg (0.7 mmol) of Pd(PPh$_3$)$_4$ in 290 mL of degassed toluene. The charged reactor is removed from the dry box, while under a blanket of N$_2$ and is connected to the house N$_2$ line. The biphasic solution is vigorously stirred and heated to 70° C. for 4 h. On cooling to RT, the organic phase is separated. The aqueous layer is washed with 3×75 mL of Et$_2$O. The combined organic extracts are washed with 3×100 mL of H$_2$O and 1×100 mL of brine and dried over Na$_2$SO$_4$. After removing the volatiles in vacuo, the resultant light yellow oil is purified via trituration with hexanes. The isolated material is recrystallized from a hot hexane solution and ultimately yielded 8.75 g, 87% yield. mp 65–66° C.

$^1$H NMR (CDCl$_3$) δ 7.2–8.3 (m, 10H), 10.25 (s, 1H) ppm. $^{13}$C NMR (CDCl$_3$) 120.3, 125.64, 125.8, 126.6, 127.26, 128.23, 129.00, 129.74, 130.00, 131.39, 134.42, 137.67, 137.97, 153.07, 160.33, 194.23 ppm.

6-naphthylpyridine-2-(2,6-diisopropylphenyl)imine: A dry, 500 mL 3-neck round bottom flask is charged with a solution of 5.57 g (23.9 mmol) of 2-formyl-6-naphthlypyridine and 4.81 g (27.1 mmol) of 2,6-diisopropylaniline in 238 mL of anhydrous THF containing 3 Å molecular sieves (6 g) and 80 mg of p-TsOH. The loading of the reactor is performed under N$_2$. The reactor is equipped with a condenser, an over head mechanical stirrer and a thermocouple well. The mixture is heated to reflux under N$_2$ for 12 h. After filtration and removal of the volatile in vacuo, the crude, brown oil is triturated with hexanes. The product is filtered off and rinsed with cold hexanes. The slightly off white solid weighes 6.42 g. No further purification is performed. mp 142–144° C.

$^1$H NMR (CDCl$_3$) δ 1.3 (d, 12H), 3.14 (m, 2H), 7.26 (m, 3H), 7.5–7.6 (m, 5H), 7.75–7.8 (m, 3H), 8.02 (m 1H), 8.48 (m, 2H) ppm. $^{13}$C NMR (CDCl$_3$) 23.96, 28.5, 119.93, 123.50, 124.93, 125.88, 125.94, 126.49, 127.04, 127.24, 128.18, 128.94, 129.7, 131.58, 134.5, 137.56, 137.63, 138.34, 148.93, 154.83, 159.66, 163.86 ppm.

(6-naphthyl-2-pyridyl)-N-(2,6-diisopropylphenyl) benzylamine: A 250 mL 3-neck flask, equipped with mechanical stirrer and a N$_2$ sparge, is charged with 6-naphthylpyridine-2-(2,6-diisopropylphenyl)imine (6.19 mg, 15.8 mmol) and 80 mL of anhydrous, degassed Et$_2$O. The solution is cooled to −78° C. while a solution of phenyllithium (13.15 mL of 1.8 M in cyclohexane, 23.7 mmol) is added dropwise over 10 min. After warming to RT over 1 h. the solution is stirred at RT for 12 hours. The reaction is then quenched with ~50 mL of aq. NH$_4$Cl. The organic layer is separated, washed with brine and H$_2$O, then dried over Na$_2$SO$_4$. Using the Biotage Chromatography system (column #FK0-1107-19073, 5% THF/95% hexanes), the product is isolated as a colorless oil. The chromatography is performed by dissolving the crude oil in 50 mL of hexanes. The purification is performed in 2×~25 mL batches, using half of the hexane stock solution for each run. 7.0 g of the oil is isolated (93% yield).

$^1$H NMR (CDCl$_3$) δ 0.90 (d, 12H), 3.0 (m, 2H), 4.86 (s, 1H), 5.16 (s, 1H), 7.00 (m, 3H), 7.1–7.6 (m, 12H), 7.8–7.88 (m, 2H), 7.91–7.99 (d, 1H) ppm. $_{13}$C NMR (CDCl$_3$) 24.58, 28.30, 70.02, 121.14, 123.62, 123.76, 123.95, 125.71, 126.32, 126.55, 126.74, 127.45, 128.04, 128.74, 129.47, 131.66, 134.49, 137.4, 138.95, 142.68, 143.02, 143.89, 159.36, 162.22 ppm.

Catalyst G-(Nme$_2$)$_3$: The reaction is performed inside of a dry box. A 100 mL round bottom flask is charged with Hf(Nme$_2$)$_4$ (2.5 g, 5.33 mmol), 30 mL of pentane and a stir bar. The amine 1 is dissolve in 40 mL of pentane then added to the stirring solution of Hf(Nme$_2$)$_4$. The mixture is stirred at ambient temperature for 16 h (overnight). The light yellow solid is filtered off and rinsed with cold pentane. The dry weight of the powder is 2.45 g. A second crop is collected from the filtrate weighing 0.63 g. The overall yield is 74%.

$^1$H NMR (C$_6$D$_6$) δ 0.39 (d, 3H, J=6.77 Hz), 1.36 (d, 3H, J=6.9 Hz), 1.65 (d, 3H, J=6.68 Hz), 1.76 (d, 3H, J=6.78 Hz), 2.34 (br s, 6H), 2.80 (br s, 6H), 2.95 (br s, 6H), 3.42 (m, 1H, J=6.8 Hz), 3.78 (m, 1H, J=6.78 Hz), 6.06 (s, 1H), 6.78 (m, 2H), 6.94 (m, 1H), 7.1–7.4 (m, 13H), 7.8 (m, 2H) ppm.

Catalyst G: The reaction is performed inside of a dry box. A 100 mL round bottom flask is charged with 70 mL of pentane and 15 mL of a 2.0 M trimethyl aluminum in hexane solution. The solution is cooled to −40° C. The hafnium trisamide compound from the previous reaction (1.07, g 1.28 mmol) is added in small portions over 5–10 minutes. Upon the addition, a white gelatinous residue forms. After 45–60 min the reaction becomes yellow with a fine, yellow, powder precipitating from the mixture. After a total reaction time of 2.5 h the mixture is filtered and 615 mg of Catalyst G is isolated as a bright, yellow powder. No further purification is performed.

$^1$H NMR (C$_6$D$_6$) δ 0.51 (d, 3H, J=6.73 Hz), 0.79 (s, 3H), 1.07 (s, 3H), 1.28 (d, 3H, J=6.73 Hz), 1.53 (m, 6H), 3.37 (m, 1H, J=6.75 Hz), 3.96 (m, 1H, J=6.73 Hz), 6.05 (s, 1H), 6.50 (d, 1H, J=7,75 Hz), 6.92 (t, 1H, J=7.93 Hz), 7.1–7.59 (m, 12H), 7.6 (d, 1H), 7.8–8.0 (m, 2H), 8.3 (m, 1H), 8.69 (d, 1H, J=7.65 Hz) ppm.

Synthesis of Catalyst H

To a solution of 9-bromophenanthrene (10.36 mg, 41 mmol) in 132 mL of anhydrous, degassed $Et_2O$ cooled to $-40°$ C. is added under $N_2$ 27 mL (43.2 mmol) of a 1.6 M solution of n-BuLi in hexanes. The solution is swirled to mix and allowed to react at $-40°$ C. for 3 hours during which colorless crystals precipitated from solution. The 9-phenanthrenyllithium is added as a slurry to a well-mixed solution of 6-naphthylpyridine-2-(2,6-diisopropylphenyl) imine (10.6 g, 27.04 mmol) in 130 mL of $Et_2O$ cooled to $-40°$ C. After warming to ambient temperature over 1 h, the solution is stirred at ambient temperature for 2 hours. The reaction is then quenched with aq. $NH_4Cl$, and subjected to an aqueous/organic work-up. The organic washes are combined and dried over $Na_2SO_4$. Upon removal of the volatiles with rotary evaporation, the product precipitates from solution. The isolated solids are rinsed with cold hexanes. The material is vacuum dried at 70° C. using the house vacuum over night. The dried material is isolated as a white solid, weighing 12.3 g for a yield of 80%. A second crop is isolated weighing 0.37 g. Mp 166–168° C.

$^1$H NMR ($C_6D_6$) δ 1.08 (dd, 12H), 3.43 (m, 2H), 5.47 (m, 1H), 6.16 (d, 1H), 7.0–7.8 (m, 14H), 8.2 (d, 1H), 8.5–8.6 (m, 4H), ppm. $^{13}$C NMR ($CDCl_3$) 24.68, 28.22, 68.87, 120.56, 122.89, 123.63, 123.73, 124.07, 124.1, 125.5, 125.59, 126.24, 126.42, 126.52, 126.76, 126.83, 126.9, 127.05, 127.14, 128.0, 128.55, 129.49, 129.55, 130.67, 130.71, 131.52, 131.55, 132.24, 134.39, 137.57, 143.31, 159.1, 162 ppm.

Catalyst H-Nme$_2$)$_3$: Inside of a dry box, six different teflon-screw capped, glass pressure tube reactors are each charged with Hf(Nme$_2$)$_4$ (1.55 g, 4.37 mmol, overall 9.3 g, 26.2 mmol), 10 mL of toluene and the ligand isolated from the previous procedure above (2.1 g, 3.68 mmol, overall 12.6 g, 22.1 mmol). The tightly sealed reactors are removed from the dry box and placed in a heater block with the temperature set at 125° C. The reactor tubes are heated overnight (~16 h). The cooled tubes are taken into the dry box and the contents of the reactor tubes are combined in a 500 mL round bottom flask. The flask is placed under vacuum to remove the dimethylamine and toluene. The light yellow/green solid which is left is rinsed with ~125 mL of cold pentane and filtered, yielding 13.6 g of a light yellow powder for a yield of 65%.

Catalyst H: The reaction is performed inside of a dry box. A 500 mL jar is charged with 250 mL of pentane and the hafnium amide isolated in the procedure outlined immediately above (13.6 g, 15.5 mmol). The mixture is cooled to $-40°$ C. To the stirring mixture is slowly added 70 mL of a 2.0 M trimethyl aluminum (140 mmol) in hexane solution. After 3 h the reaction becomes yellow with a fine, powder precipitating from the mixture. The mixture is then cooled to $-40°$ C. and filtered. The initially collected product is rinsed with 2×60 mL of cold pentane. 10.24 g Catalyst H is isolated (84% yield) with a purity of >99% by $^1$H NMR.

Synthesis of Armeenium Borate[methylbis (hydrogenatedtallowalkyl)ammonium tetrakis (pentafluoro phenyl)borate]

Armeenium borate can be prepared from ARMEEN® M2HT (available from Akzo-Nobel), HCl, and Li[B($C_6F_5$)$_4$] according to Example 2 of U.S. Pat. No. 5,919,983.

General 1 Gallon Continuous Solution Propylene/ Ethylene

I. Copolymerization Procedure

Purified toluene solvent, ethylene, hydrogen, and propylene are supplied to a 1 gallon reactor equipped with a jacket for temperature control and an internal thermocouple. The solvent feed to the reactor is measured by a mass-flow controller. A variable speed diaphragm pump controls the solvent flow rate and increases the solvent pressure to the reactor. The propylene feed is measured by a mass flow meter and the flow is controlled by a variable speed diaphragm pump. At the discharge of the pump, a side stream is taken to provide flush flows for the catalyst injection line and the reactor agitator. The remaining solvent is combined with ethylene and hydrogen and delivered to the reactor. The ethylene stream is measured with a mass flow meter and controlled with a Research Control valve. A mass flow controller is used to deliver hydrogen into the ethylene stream at the outlet of the ethylene control valve. The temperature of the solvent/monomer is controlled by use of a heat exchanger before entering the reactor. This stream enters the bottom of the reactor. The catalyst component solutions are metered using pumps and mass flow meters, and are combined with the catalyst flush solvent. This stream enters the bottom of the reactor, but in a different port than the monomer stream. The reactor is run liquid-full at 500 psig with vigorous stirring. The process flow is in from the bottom and out of the top. All exit lines from the reactor are steam traced and insulated. Polymerization is stopped with the addition of a small amount of water, and other additives and stabilizers can be added at this point. The stream flows through a static mixer and a heat exchanger in order to heat the solvent/polymer mixture. The solvent and unreacted monomers are removed at reduced pressure, and the product is recovered by extrusion using a devolatilizing extruder. The extruded strand is cooled under water and chopped into pellets. The operation of the reactor is controlled with a process control computer.

EXAMPLE 1

Propylene/Ethylene Polymerization Using Metallocene Catalyst E (Comparative)

The general procedure for the 1 gallon continuous solution polymerization outlined above was employed. A catalyst solution containing 2.6 ppm Zr from Catalyst E was prepared and added to a 4 L catalyst storage tank. This solution was combined in a continuous stream with a continuous stream of a solution containing Armeenium tetrakis(pentafluorophenyl)borate in toluene and a continuous stream of a solution of PMAO-IP in toluene to give a ratio of total Ti:B:Al of 1:1.2:30. The activated catalyst solution was fed continuously into the reactor at a rate sufficient to maintain the reactor temperature at approximately 80 degrees C. and a polymer production rate of approximately 3 pounds an hour. The polymer solution was continuously removed from the reactor exit and was contacted with a solution containing 100 ppm of water for each part of the polymer solution, and polymer stabilizers (i.e., 1000 ppm Irgaphos 168 and 1000 ppm Irganox 1010 per part of the polymer). The resulting exit stream was mixed, heated in a heat exchanger, and the mixture was introduced into a separator where the molten polymer was separated from the solvent and unreacted monomers. The resulting molten polymer was extruded and chopped into pellets after being cooled in a water bath. For this example, the propylene to ethylene ratio was 22.0. Product samples were collected over 1 hour time periods, after which time the melt flow rate was determined for each sample. FIG. 9 is a $^{13}$C NMR of Comparative Example 1, and it demonstrates the absence of regio-error peaks in the region around 15 ppm.

EXAMPLES 2–6

Examples 2–6 were conducted similar to Example 1 except as otherwise noted in Tables 2-6-1 and 2-6-2 below. Catalyst E is listed for comparative purposes. FIG. 8 is the $^{13}$C NMR sprectrum of the propylene/ethylene copolymer product of Example 2. FIGS. 2A and 2B show a comparison of the DSC heating traces of the propylene/ethylene copolymers of Comparative Example 1 and Example 2.

TABLE 2-6-1

Polymerization Conditions

| Example | Reactor TEMP DEGC | SOLV FLOW LB/HR | C2 FLOW LB/HR | C3 FLOW LB/HR | H2 FLOW SCCM | POLY LBS/HR production rate |
|---|---|---|---|---|---|---|
| 1 (comparative) | 80.5 | 36.0 | 0.50 | 11.00 | 0 | 3.13 |
| 2 | 80.5 | 33.0 | 0.20 | 6.00 | 20.8 | 3.47 |
| 3 | 80.1 | 26.0 | 0.10 | 6.00 | 14.1 | 3.09 |
| 4 | 79.9 | 26.0 | 0.20 | 6.00 | 20.1 | 3.25 |
| 5 | 80.0 | 26.0 | 0.30 | 6.00 | 26.1 | 3.16 |
| 6 | 80.3 | 26.0 | 0.40 | 6.00 | 32.1 | 3.32 |

TABLE 2-6-2

Monomer conversion and activity

| Example | Catalyst | C3/C2 ratio | propylene conversion | ethylene conversion | catalyst concentration ppm(metal) | efficiency g metal per g polymer |
|---|---|---|---|---|---|---|
| 1 (comparative) | E | 22.00 | 25.7% | 64.8% | 2.6 | 6,145,944 |
| 2 | G | 30.17 | 53.1% | 99.1% | 25.6 | 235,823 |
| 3 | H | 61.07 | 48.7% | 98.4% | 55.0 | 225,666 |
| 4 | H | 30.34 | 49.7% | 99.0% | 55.0 | 259,545 |
| 5 | H | 20.17 | 46.8% | 98.6% | 55.0 | 259,282 |
| 6 | H | 15.00 | 48.0% | 98.7% | 55.0 | 278,579 |

TABLE 2-6-3

Summary of Polymer Analysis Data

| Example | MFR (g/10 min) | Density (kg/dm3) | Cryst. (%) from density | DSC Tg (° C.) | Tc, o (° C.) | Tc, p (° C.) |
|---|---|---|---|---|---|---|
| 1 | 72 | 0.8809 | 37.9 | −26.1 | 52.3 | 47.6 |
| 2 | 1.7 | 0.8740 | 29.6 | −24.8 | 59.0 | 49.3 |
| 3 | 2.2 | 0.8850 | 42.8 | −10.0 | 76.6 | 64.5 |
| 4 | 2.3 | 0.8741 | 29.7 | −23.2 | 50.8 | 41.6 |
| 5 | 2 | 0.8648 | 18.3 | −27.1 | 30.4 | 10.9 |
| 6 | 2.0 | 0.8581 | 9.9 | −29.6 | — | — |

TABLE 2-6-4

Summary of Polymer Analysis Data cont'd

| Example | ΔHc (J/g) | Cryst. (%) (from Hc) | Tm, p (° C.) | Tm, e (° C.) | ΔHf (J/g) | Cryst. (%) (from Hf) |
|---|---|---|---|---|---|---|
| 1 | 40.8 | 24.7 | 91.9 | 114.3 | 52.1 | 31.6 |
| 2 | 27.1 | 16.4 | 64.5 | 128.9 | 38.0 | 23.0 |
| 3 | 45.0 | 27.3 | 102.2 | 145.7 | 65.3 | 39.6 |
| 4 | 30.6 | 18.5 | 67.4 | 145.6 | 42.9 | 26.0 |
| 5 | 8.7 | 5.3 | 50.0 | 119.4 | 13.0 | 7.9 |
| 6 | — | — | — | — | — | — |

TABLE 2-6-5

Summary of Polymer Analysis Data cont'd

| Example | Ethylene (wt %)* | Ethylene (mol %)* | Regio-errors 14–16 ppm (mol %)* | Mn (kg/mol) | Mw (kg/mol) | MWD |
|---|---|---|---|---|---|---|
| 1 | 9.5 | 13.6 | 0.00 | 58.5 | 117.4 | 2.0 |
| 2 | 8.2 | 11.8 | 0.24 | 132.6 | 315.7 | 2.4 |
| 3 | 5.6 | 8.2 | 0.46 | 146.0 | 318.3 | 2.2 |
| 4 | 8.2 | 11.8 | 0.34 | 138.5 | 305.7 | 2.2 |
| 5 | 11.1 | 15.8 | 0.35 | | | |
| 6 | 13.2 | 18.6 | 0.37 | 127.5 | 306.8 | 2.4 |

TABLE 2-6-6

Summary of Polmer Analysis Data cont'd

| Example | % mm* | % mr* | % rr* |
|---|---|---|---|
| 1 | 98.55 | 0 | 1.45 |
| 2 | 98.23 | 1.09 | 5.68 |
| 3 | 94.3 | 2.21 | 3.43 |
| 4 | 96.37 | 0 | 3.63 |
| 5 | 95.3 | 0.0 | 4.66 |
| 6 | 95.17 | 0 | 4.83 |

*corrected PPE + EPE

EXAMPLES 7–8
Homopolymerization of Propylene using Catalyst B and C

Figure 13A:
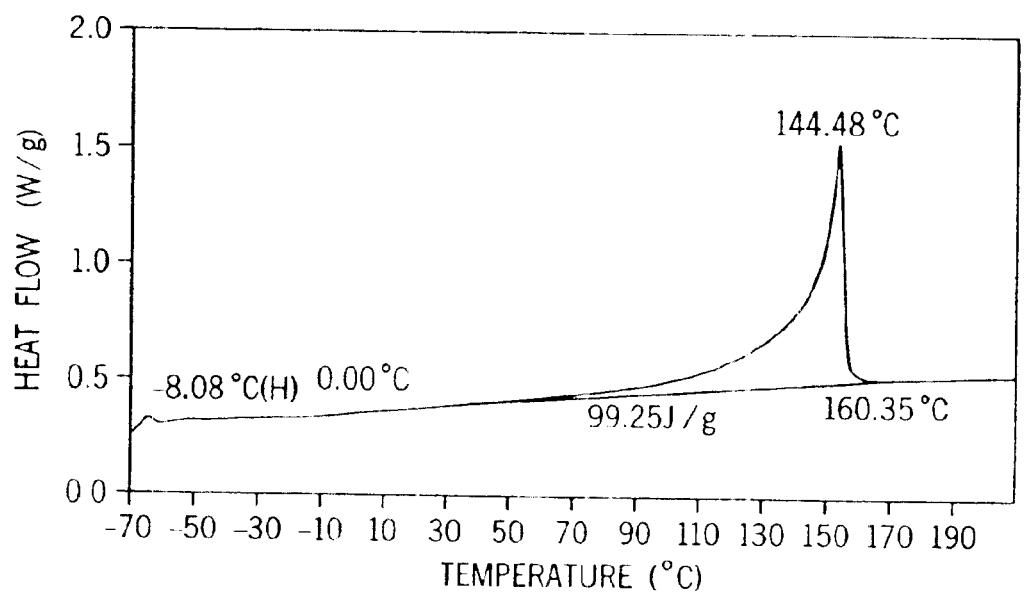
FIGS. 13A and 13B show the DSC heating and cooling traces of the P* homopolymer of Example 8, prepared using Catalyst H.
Figure 13B:
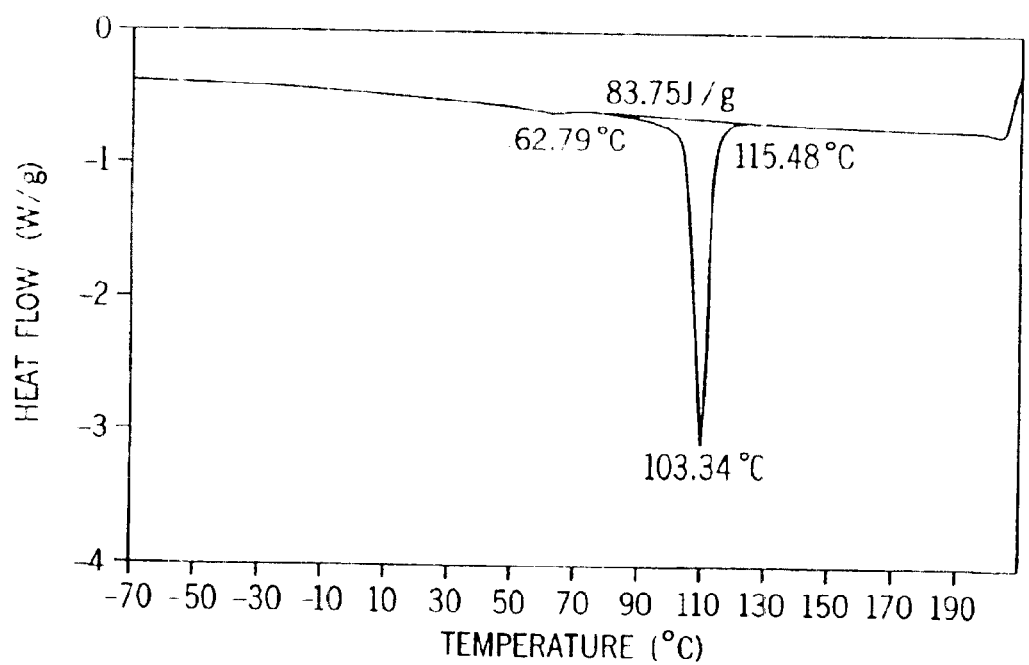

Examples 7–8 were conducted similar to Example 1 without ethylene. The procedure was similar to Example 1 with exceptions noted in Tables 7-8-1 and 7-8-2 below. FIG. 6 shows the $^{13}$C NMR spectrum of the proplene homopolymer product of Example 7 prepared using catalyst G. FIG. 7 shows the $^{13}$C NMR spectrum of the propylene homopolymer product of Example 8 prepared using catalyst H. Both spectra show a high degree of isotacticity, and the expanded Y-axis scale of FIG. 7 relative to FIG. 6 shows more clearly the regio-error peaks. FIGS. 13A and 13B show the DSC heating and cooling traces of the propylene homopolymer of Example 8.

TABLE 7-8-1

Reactor Conditions and Catalyst Activity

| Example | Reactor TEMP DEGC | SOLV FLOW LB/HR | C3 FLOW LB/HR | H2 FLOW SCCM | POLY LBS/HR WEIGHED | Catalyst | propylene conversion | catalyst concentration ppm(metal) | efficiency g metal per g polymer |
|---|---|---|---|---|---|---|---|---|---|
| 7 | 99.8 | 33.1 | 6.00 | 1.9 | 2.30 | G | 38.3% | 25.6 | 111,607 |
| 8 | 100.3 | 26.0 | 6.00 | 2.6 | 2.57 | H | 42.8% | 32.5 | 100,987 |

TABLE 7-8-2

Polymer Analysis

| Example | MFR (g/10 min) | Density (kg/dm3) | Cryst. (%) froYm density | DSC Tg (° C.) | Tc, o (° C.) | Tc, p (° C.) | Mn (kg/mol) | Mw (kg/mol) | MWD |
|---|---|---|---|---|---|---|---|---|---|
| 7 | 1.9 | 0.8995 | 59.7 | −6.0 | 104.2 | 100.4 | 114.6 | 350.8 | 2.7 |
| 8 | 2.5 | 0.9021 | 62.7 | −8.1 | 105.7 | 103.3 | 125.5 | 334.0 | 2.7 |

TABLE 7-8-3

Polymer Analaysis Continued

| Example | ΔHc (J/g) | Cryst. (%) (from Hc) | Tm, p (° C.) | Tm, e (° C.) | ΔHf (J/g) | Cryst. (%) (from Hf) | Regio-errors 14–16 ppm (mol %)* | % mm** | % mr** | % rr** |
|---|---|---|---|---|---|---|---|---|---|---|
| 7 | 76.9 | 46.6 | 139.7 | 153.5 | 93.7 | 56.8 | 2.69 | 92.12 | 5.79 | 2.08 |
| 8 | 83.6 | 50.7 | 144.5 | 158.2 | 100.6 | 61.0 | 2.36 | 93.93 | 4.45 | 1.62 |

*determined by NMR **corrected PPE + EPE

EXAMPLE 9

This example demonstrates the calculation of B values for certain of the Examples disclosed herein. The polymer from Comparative Example 1 is analyzed as follows. The data was collected using a Varian UNITY Plus 400 MHz NMR spectrometer, corresponding to a $^{13}C$ resonance frequency of 100.4 MHz. Acquisition parameters were selected to ensure quantitative $^{13}C$ data acquisition in the presence of the relaxation agent. The data was acquired using gated $^{1}H$ decoupling, 4000 transients per data file, a 7 sec pulse repetition delay, spectral width of 24,200 Hz and a file size of 32K data points, with the probe head heated to 130° C. The sample was prepared by adding approximately 3 mL of a 50/50 mixture of tetrachloroethane-d2/orthodichlorobenzene that is 0.025M in chromium acetylacetonate (relaxation agent) to 0.4 g sample in a 10 mm NMR tube. The headspace of the tube was purged of oxygen by displacement with pure nitrogen. The sample was dissolved and homogenized by heating the tube and its contents to 150° C., with periodic refluxing initiated by heat gun.

Following data collection, the chemical shifts were internally referenced to the mmmm pentad at 21.90 ppm.

For propylene/ethylene copolymers, the following procedure is used to calculate the percent ethylene in the polymer. Integral regions are determined as follows:

TABLE 9-1

Integral Regions for Calculating % Ethylene

| Region designation | Ppm | Integral area |
|---|---|---|
| A | 44–49 | 259.7 |
| B | 36–39 | 73.8 |
| C | 32.8–34 | 7.72 |
| P | 31.0–30.8 | 64.78 |
| Q | Peak at 30.4 | 4.58 |
| R | Peak at 30 | 4.4 |
| F | 28.0–29.7 | 233.1 |
| G | 26–28.3 | 15.25 |
| H | 24–26 | 27.99 |
| I | 19–23 | 303.1 |

Region D is calculated as follows: D=P−(G−Q)/2.

Region E is calculated as follows: E=R+Q+(G−Q)/2.

The triads are calculated as follows:

TABLE 9-2

Traid Calculation

PPP = (F + A − 0.5D)/2
PPE = D
EPE = C
EEE = (E − 0.5G)/2
PEE = G
PEP = H
Moles P = (B + 2A)/2
Moles E = (E + G + 0.5B + H)/2

For this example, the mole % ethylene is calculated to be 13.6 mole %.

For this example, the triad mole fractions are calculated to be as follows:

TABLE 9-3

| Triad Mole Calculation |
| --- |
| PPP = 0.6706 |
| PPE = 0.1722 |
| EPE = 0.0224 |
| EEE = 0.0097 |
| PEE = 0.0442 |
| PEP = 0.0811 |

From this, the B value is calculated to be:

$$(0.172+0.022+0.044+0.081)/2(0.136 \times 0.864) = 1.36$$

In a similar manner, the B values for the following examples are calculated to be:

TABLE 9-4

| B-Value Calculation | |
| --- | --- |
| Example | B Value |
| Comparative 1 | 1.36 |
| 2 | 1.68 |
| 3 | 1.7 |
| 4 | 1.78 |
| 6 | 1.7 |

EXAMPLE 10

Figure 14:
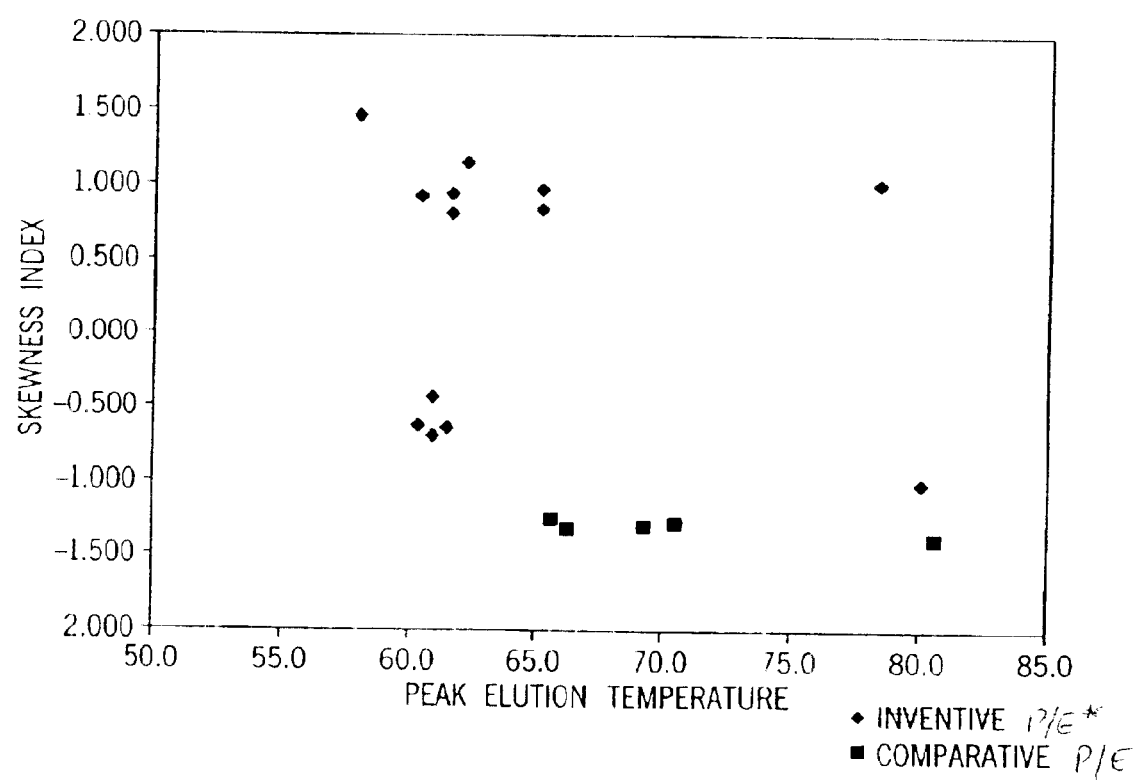
FIG. 14 shows a comparison of the skewness index for a P/E* copolymer and several P/E copolymers.

Table 10 is a summary showing the skewness index, $S_{ix}$, for inventive and prior art samples. All of the samples were prepared and measured as described in Table C in the Description of the Preferred Embodiments and entitled Parameters Used for TREF. The copolymers of the invention have a skewness index greater than about (−1.2). The results from Table 10 are represented graphically in FIG. 14.

The inventive examples show unusual and unexpected results when examined by TREF. The distributions tend to cover a large elution temperature range while at the same time giving a prominent, narrow peak. In addition, over a wide range of ethylene incorporation, the peak temperature, $T_{Max}$, is near 60° C. to 65° C. In the prior art, for similar levels of ethylene incorporation, this peak moves to higher elution temperatures with lower ethylene incorporation.

For conventional metallocene catalysts the approximate relationship of the mole fraction of propylene, $X_p$, to the TREF elution temperature for the peak maximum, $T_{Max}$, is given by the following equation:

$$\text{Log}_e(X_p) = -289/(273+T_{max}) + 0.74$$

For the inventive copolymers, the natural log of the mole fraction of propylene, LnP, is greater than that of the conventional metallocenes, as shown in the is equation:

$$LnP > -289/(273+T_{max}) + 0.75$$

TABLE 10

Summary of Skewness Index Results

| P/E* Sample No. | Catalyst Type | Ethylene Content (Mole %) | Elution Temperature of Peak maximum (° C.) | $S_{ix}$ |
| --- | --- | --- | --- | --- |
| 10-1 | Catalyst H | 8.2 | 61.4 | 0.935 |
| 10-2 | Catalyst J | 8.9 | 60.8 | −0.697 |
| 10-3 | Catalyst J | 8.5 | 61.4 | −0.642 |
| 10-4 | Catalyst J | 7.6 | 65.0 | 0.830 |
| 10-5 | Catalyst J | 7.6 | 65.0 | 0.972 |
| 10-6 | Catalyst J | 8.6 | 61.4 | 0.804 |
| 10-7 | Catalyst J | 9.6 | 60.2 | −0.620 |
| 10-8 | Catalyst J | 12.4 | 60.2 | 0.921 |
| 10-9 | Catalyst J | 8.6 | 60.8 | −0.434 |
| 10-10 | Catalyst J | 8.6 | 62.0 | 1.148 |
| 10-11 | Catalyst H | — | 57.8 | 1.452 |
| 10-12 | Catalyst J | — | 78.2 | 1.006 |
| 10-13 | Catalyst H | 4.4 | 80.0 | −1.021 |
| 10-14 | Catalyst E | 7.6 | 80.6 | −1.388 |
| 10-15 | Catalyst E | 10.0 | 70.4 | −1.278 |
| 10-16 | Catalyst E | 10.7 | 66.2 | −1.318 |
| 10-17 | Catalyst F | 11.1 | 69.2 | −1.296 |
| 10-18 | Catalyst E | 10.6 | 65.6 | −1.266 |

EXAMPLE 11

DSC analysis shows that propylene/ethylene copolymers produced by a solution polymerization process using a nonmetallocene, metal-centered, pyridal-amine ligand catalyst have melting behavior that differs in surprising ways from propylene/ethylene copolymers produced by metallocene polymerization processes that are known in the art. The different melting behavior of these copolymers compared to that of copolymers that are known in the art not only demonstrates the novelty of these materials, but also can be used to infer certain advantages of these materials for some applications. The novel aspects of the melting behavior of these copolymers and their associated utility are discussed below, after first describing the DSC analysis method.

Any volatile materials (e.g., solvent or monomer) are removed from the polymer prior to DSC analysis. A small amount of polymer, typically five to fifteen milligrams, is accurately weighed into an aluminum DSC pan with lid. Either hermetic or standard type pans are suitable. The pan containing the sample is then placed on one side of the DSC cell, with an empty pan with lid placed on the reference side of the DSC cell. The DSC cell is then closed, with a slow purge of nitrogen gas through the cell during the test. Then the sample is subjected to a programmed temperature sequence that typically has both isothermal segments and segments where the temperature is programmed to increase or decrease at a constant rate. Results that are presented here were all obtained using heat-flux type DSC instruments manufactured by TA Instruments (e.g., Model 2910 DSC). The measurement principles underlying heat-flux DSC are described on page 16 of Turi, ibid. The primary signals generated by such instruments are temperature (units: ° C.) and differential heat flow (units: watts) into or out of the sample (i.e., relative to the reference) as a function of elapsed time. Melting is endothermic and involves excess heat flow into the sample relative to the reference, whereas crystallization is exothermic and involves excess heat flow out of the sample. These instruments are calibrated using indium and other narrow-melting standards. Calibration ensures that the temperature scale is correct and for the proper correction of unavoidable heat losses.

Temperature programs for DSC analysis of semi-crystalline polymers involve several steps. Although the temperature programs used to generate the data presented here differed in some details, the critical steps were maintained constant throughout. The first step is an initial heating to a temperature sufficient to completely melt the sample; for polypropylene homopolymers and copolymers, this is 210° C. or higher. This first step also helps insure excellent thermal contact of the polymer sample with the pan. Although details of this first step differed for data presented here—for example, the rate of heating, the upper temperature, and the hold time at the upper temperature—in all cases the choices were sufficient to achieve the principal objectives of this step, of bringing all samples to a common completely melted starting point with good thermal contact. The second step involves cooling at a constant rate of 10° C./min from an upper temperature of at least 210° C. to a lower temperature of 0° C. or less. The lower temperature is chosen to be at or slightly below the glass transition temperature of the particular propylene polymer. The rate of crystallization becomes very slow at the glass transition temperature; hence, additional cooling will have little effect on the extent of crystallization. This second step serves to provide a standard crystallization condition, prior to examining subsequent melting behavior. After a brief hold at this lower temperature limit, typically one to three minutes, the third step is commenced. The third step involves heating the sample from a temperature of 0° C. or lower (i.e., the final temperature of the previous step) to 210° C. or higher at a constant rate of 10° C./min. This third step serves to provide a standard melting condition, as preceded by a standard crystallization condition. All the melting behavior results presented here were obtained from this third step, that is, from the second melting of the sample.

The output data from DSC consists of time (sec), temperature (° C.), and heat flow (watts). Subsequent steps in the analysis of melting endotherms are as follows. First, the heat flow is divided by the sample mass to give specific heat flow (units: W/g). Second, a baseline is constructed and subtracted from the specific heat flow to give baseline-subtracted heat flow. For the analyses presented here, a straight-line baseline is used. The lower temperature limit for the baseline is chosen as a point on the high temperature side of the glass transition. The upper temperature limit for the baseline is chosen as a temperature about 5–10° C. above the completion of the melting endotherm. Although a straight-line baseline is theoretically not exact, it offers greater ease and consistency of analysis, and the error introduced is relatively minor for samples with specific heats of melting of about 15–20 Joules per gram or higher. Employing a straight-line baseline in lieu of a more theoretically correct baseline does not substantively affect any of the results or conclusions presented below, although the fine details of the results would be expected to change with a different prescription of the instrumental baseline.

There are a number of quantities that can be extracted from DSC melting data. Quantities that are particularly useful in demonstrating differences or similarities among different polymers are: (1) the peak melting temperature, $T_{max}$ (° C.), which is the temperature at which the baseline-subtracted heat flow is a maximum (here the convention is that heat flow into the sample is positive); (2) the specific heat of melting, $\Delta h_m$ (J/g), which is the area under the melting endotherm obtained by integrating the baseline-subtracted heat flow $(dq/dt)$ (W/g) versus time between the baseline limits; (3) the specific heat flow $(dq/dt)_{max}$ (W/g) at the peak melting temperature; (4) the peak specific heat flow normalized by the specific heat of melting, $\{(dq/dt)_{max}/\Delta h_m\}$ ($sec^{-1}$); (5) the first moment $T_1$ of the melting endotherm, defined and calculated as described below; (6) the variance $V_1$ (° $C.^2$) of the melting endotherm relative to the first moment $T_1$, defined and calculated as described below; and (7) the square root of the variance, $V_1^{1/2}$ (° C.), which is one measure of the breadth of the melting endotherm.

Treatment of the melting endotherm as a distribution is a useful way to quantify its breadth. The quantity that is distributed as a function of temperature is the baseline-subtracted heat flow $(dq/dt)$. That this is also a distribution of temperature is made explicit using the calculus chain rule, $(dq/dt)=(dq/Dt)(Dt/dt)$ where $(Dt/dt)$ is the heating rate. The standard definition of the first moment $T_1$ of this distribution is given by the following equation, where the integrations are carried out between the baseline limits. All integrations are most reliably performed as $(dq/dt)$ versus time, as opposed to the alternative $(dq/Dt)$ versus temperature. In the following equation, $(dq/dt)$ and T are the specific heat flow and temperature at time t.

$$T_1 = \frac{\int T \cdot (dq/dt)dt}{\int (dq/dt)dt}$$

The variance $V_1$ relative to the first moment is then standardly defined as:

$$V_1 = \frac{\int (T-T_1)^2 \cdot (dq/dt)dt}{\int (dq/dt)dt}$$

Both $V_1$ and $V_1^{1/2}$ are measures of the breadth of the melting endotherm.

Results of DSC analyses of both inventive and comparative polymers are shown in Table 11-1. All the samples are propylene/ethylene copolymers, with the exception of Samples 1–4 and 17 which are homopolymers. Polymers 1–16 were made using Catalyst H in a solution process. Polymers 17–27 were made with Catalyst E in a solution process. An idea of the precision of the experimental method plus the data analysis procedure is provided by replicates (polymers 17, 20, and 22) and by the consistency of results for sets of polymers that were synthesized under nearly identical conditions (polymers 1–4, 7–9, 10–12, and 13–16).

Figure 15:
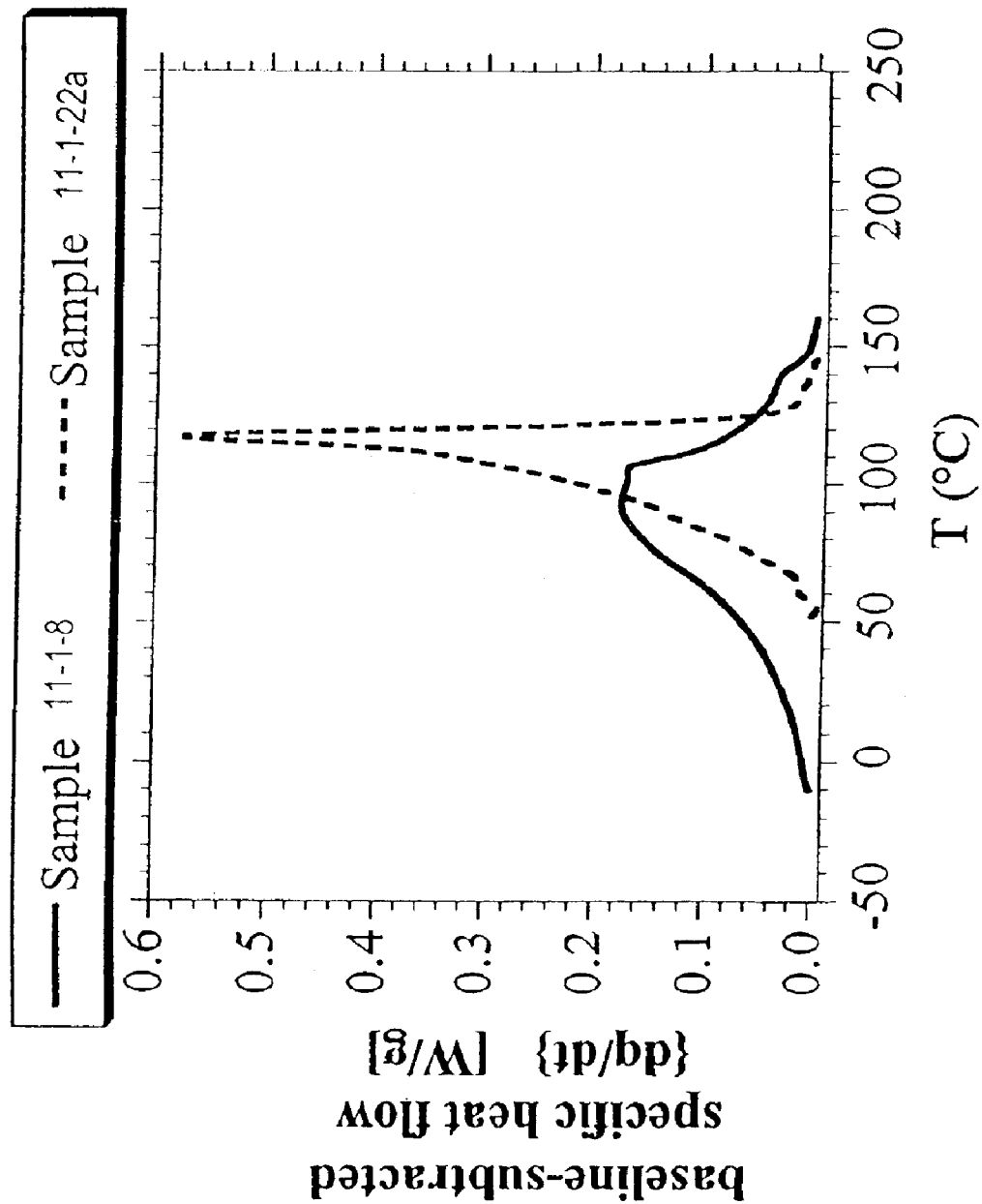
FIG. 15 compares the melting endotherms of Samples 8 and 22a of Example 11.

Differences in melting behavior are most easily seen with the aid of figures. FIG. 15 compares the melting endotherms of Samples 8 and 22a. These two propylene/ethylene copolymers have nearly equivalent heats of melting and mole percent ethylene contents, about 71 J/g and 8 mole %. However, despite these similarities, the melting behavior of the inventive copolymer (Sample 8) is surprisingly different than that of the comparative copolymer (Sample 22a). The melting endotherm of Sample 8 is shifted towards lower temperatures and significantly broadened, when comparing at equivalent heat of melting. These changes in melting behavior are unique to and characteristic of the copolymers of this invention.

Comparison at equivalent heats of melting is particularly meaningful and relevant. This is because equivalent heats of melting implies approximately equal levels of crystallinity, which in turn implies that the room temperature moduli should be similar. Therefore, at a given modulus or stiffness, the copolymers of this invention possess usefully broadened melting ranges compared to typical non-inventive copolymers.

FIGS. 16–20, which are derived from the results in Table 11-1, further highlight the differences in melting behavior for the copolymers of this invention compared to typical copolymers. For all five of these figures, quantities are plotted as functions of the heat of melting, which as described above is an especially meaningful and relevant basis for making intercomparisons and inferring utility. For these plots, data have broken into two series based on the catalyst type used to make the polymer, either metallocene or nonmetallocene type.

Figure 16:
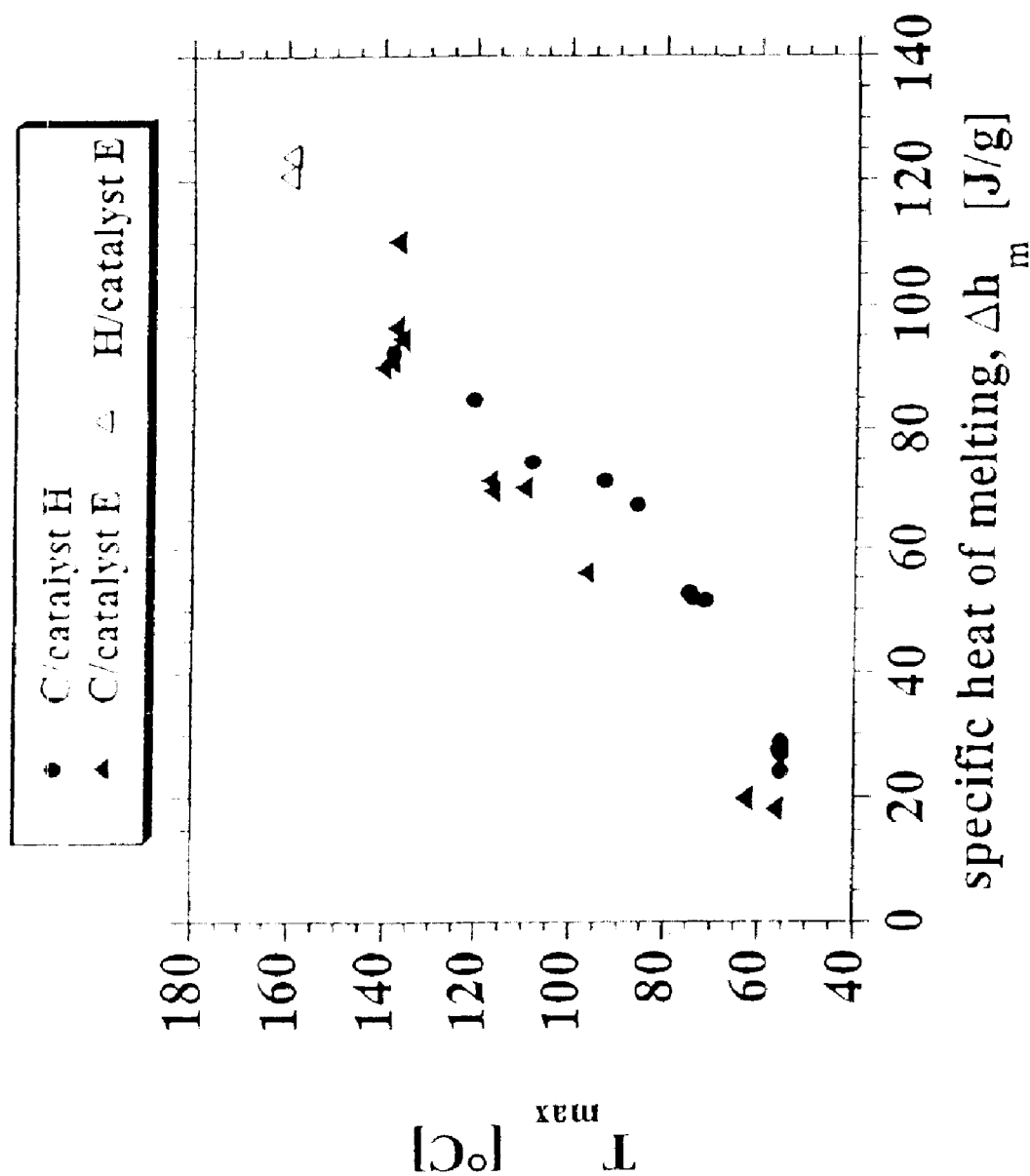
FIG. 16 demonstrates the shift in peak melting temperature towards lower temperature for the P/E* copolymer of Example 11.

FIG. 16 demonstrates how the peak melting temperature is shifted towards lower temperature for the copolymers of this invention. All the changes in melting behavior, of which this shift in peak melting temperature is but one example, imply that there are differences in the crystalline structure at the level of crystal lamellae or other type of primary crystalline elements. In turn, such differences in crystalline structure can most reasonably be attributed to differences in microstructure, for example, the different type of misinsertion errors or the higher B values that characterize the polymers of this invention. Regardless of the exact nature of the microstructural features that give rise to the changes in melting behavior, the changes are in and of themselves evidence that the copolymers of this invention are novel compositions.

Figure 17:
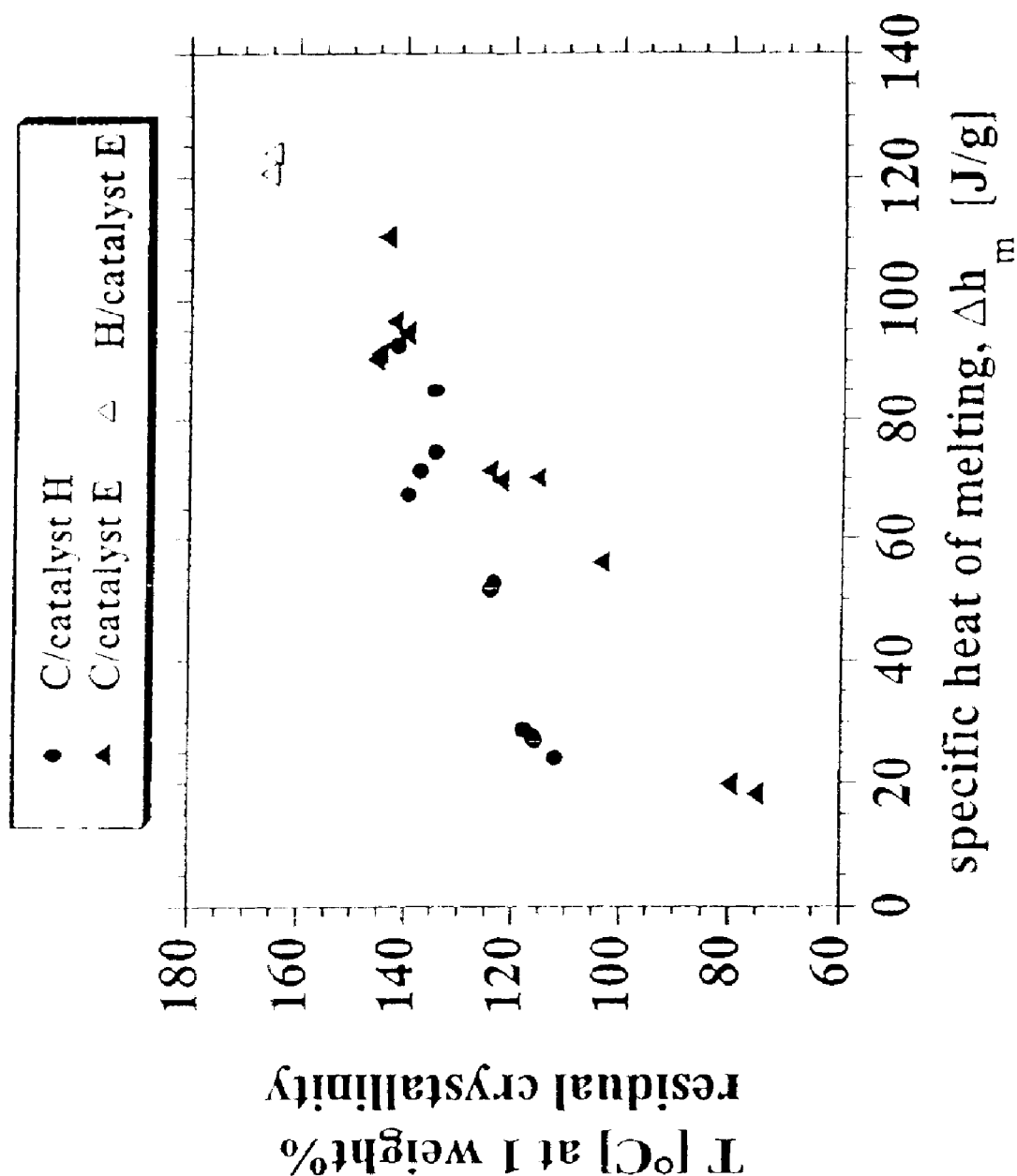
FIG. 17 is a plot of the temperature at which approximately 1 percent crystallinity remains in DSC samples of Example 11.

FIG. 17 which shows a plot of the temperature $T_{1\%\,c}$ at which there is approximately 1% residual crystallinity, demonstrates another surprising aspect of the melting behavior of the copolymers of this invention. The factor that is used to convert specific heat of melting into nominal weight % crystallinity is 165 J/g=100 weight % crystallinity. (Use of a different conversion factor could change details of the results but not substantive conclusions.) With this conversion factor, the total crystallinity of a sample (units: weight % crystallinity) is calculated as 100% times $\Delta h_m$ divided by 165 J/g. And, with this conversion factor, 1% residual crystallinity corresponds to 1.65 J/g. Therefore, $T_{1\%\,c}$ is defined as the upper limit for partial integration of the melting endotherm such that $\Delta h_m$ minus the partial integral equals 1.65 J/g, where the same lower limit and baseline are used for this partial integration as for the complete integration. Surprisingly, for nonmetallocene-catalyzed copolymers as compared to metallocene-catalyzed copolymers, this 1% residual crystallinity temperature shifts downward less rapidly with increase in ethylene level (i.e., with decrease in the heat of melting). This behavior of $T_{1\%\,c}$ is similar to that of the final temperature of melting $T_{me}$.

Figure 18:
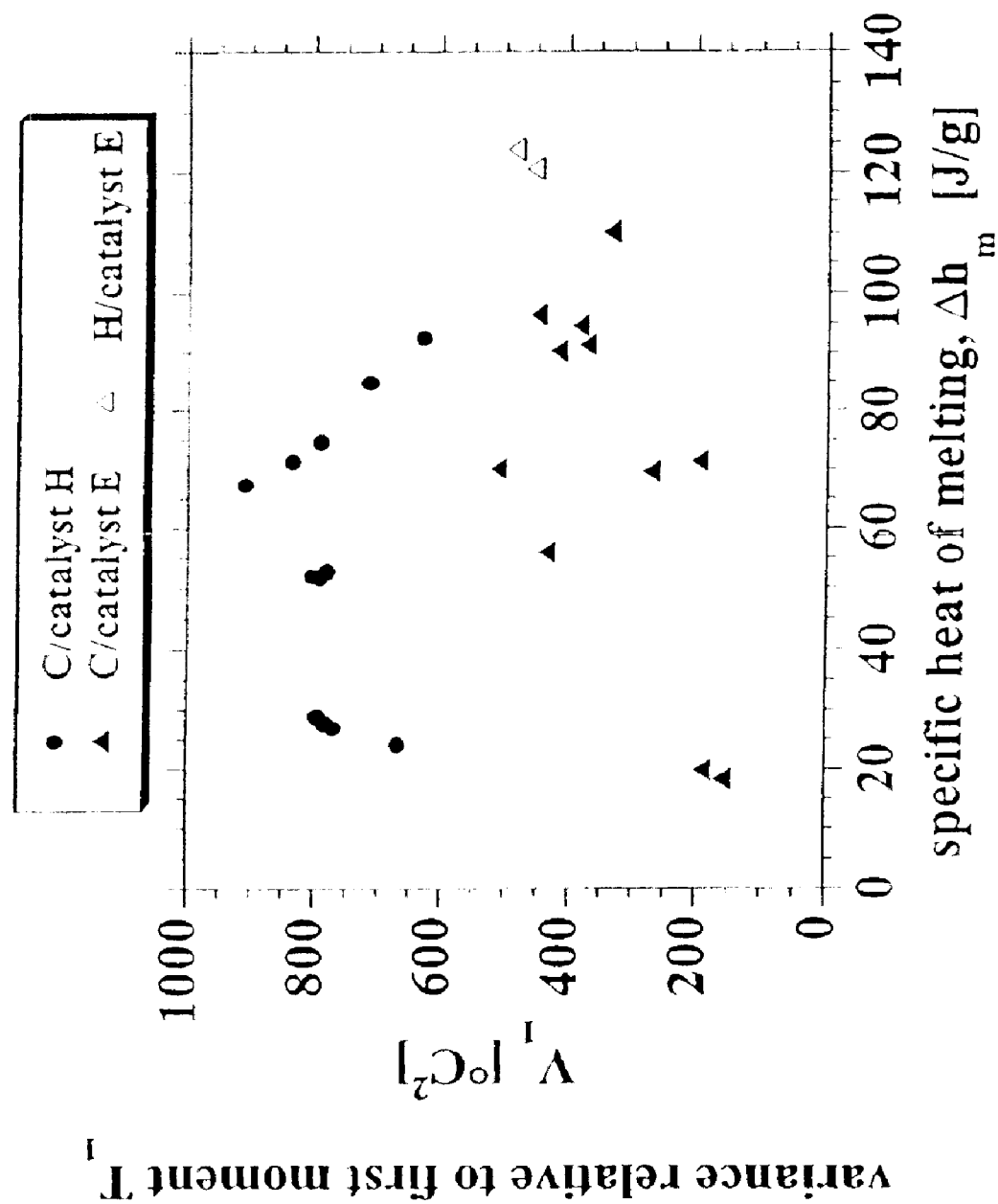
FIG. 18 shows the variance relative to the first moment of the melting endotherm as a function of the heat of melting of various samples of Example 11.

FIG. 18, which shows the variance relative to the first moment of the melting endotherm as a function of the heat of melting, demonstrates directly the greater breadth of the melting endotherm for the copolymers of this invention.

Figure 19:
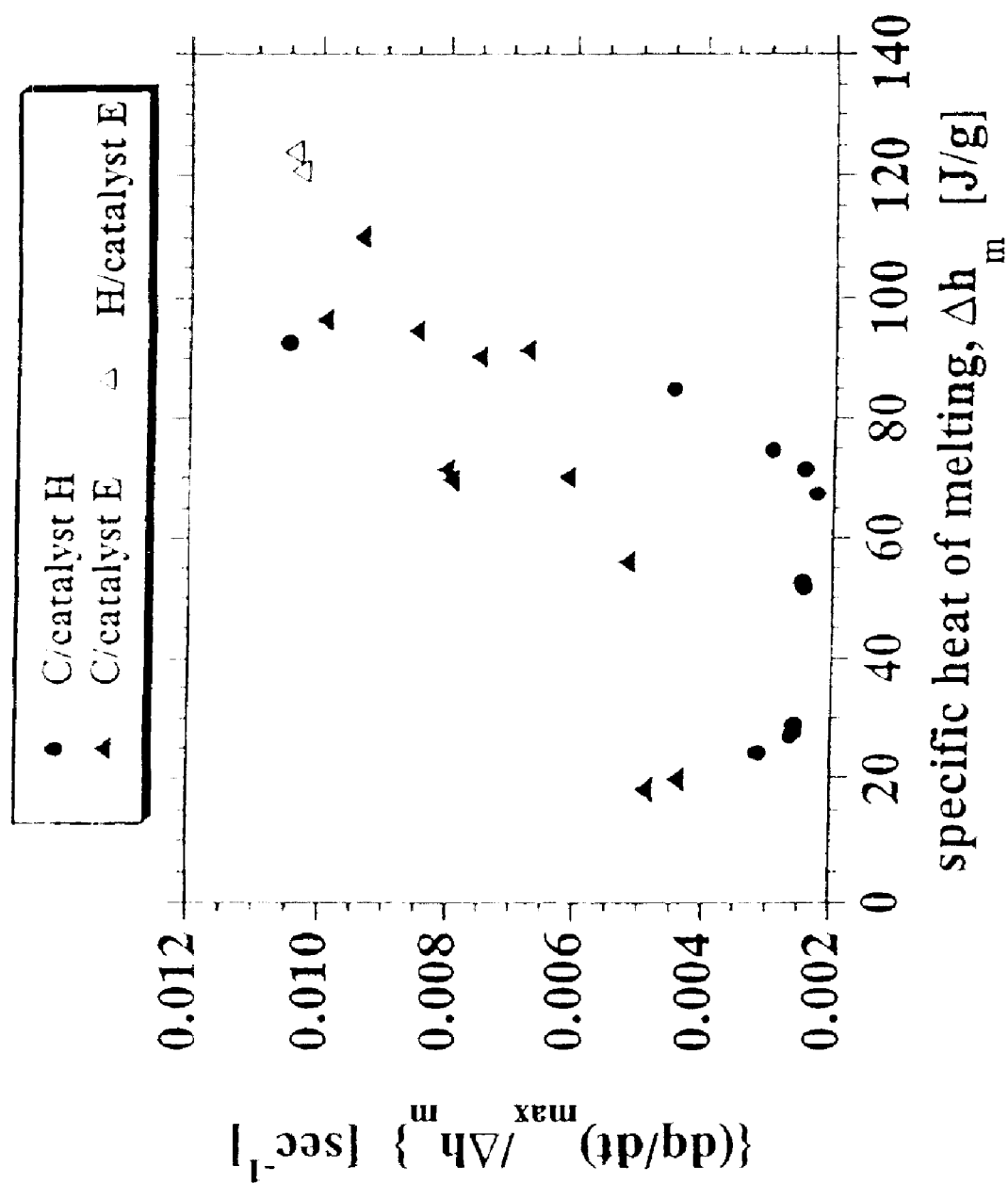
FIG. 19 shows the maximum heat flow normalized by the heat of melting as a function of the heat of melting for various samples of Example 11.

FIG. 19, which shows the maximum heat flow normalized by the heat of melting as a function of the heat of melting, further demonstrates the broadening of the melting endotherm. This is because, at equivalent heat of melting, a lower peak value implies that the distribution must be broadened to give the same area. Roughly approximating the shape of these melting curves as a triangle, for which the area is given by the formula one-half times the base times the height, then b1/b2=h2/h1. The inventive copolymers show as much as a four-fold decrease in height, implying a significant increase in breadth.

Figure 20:
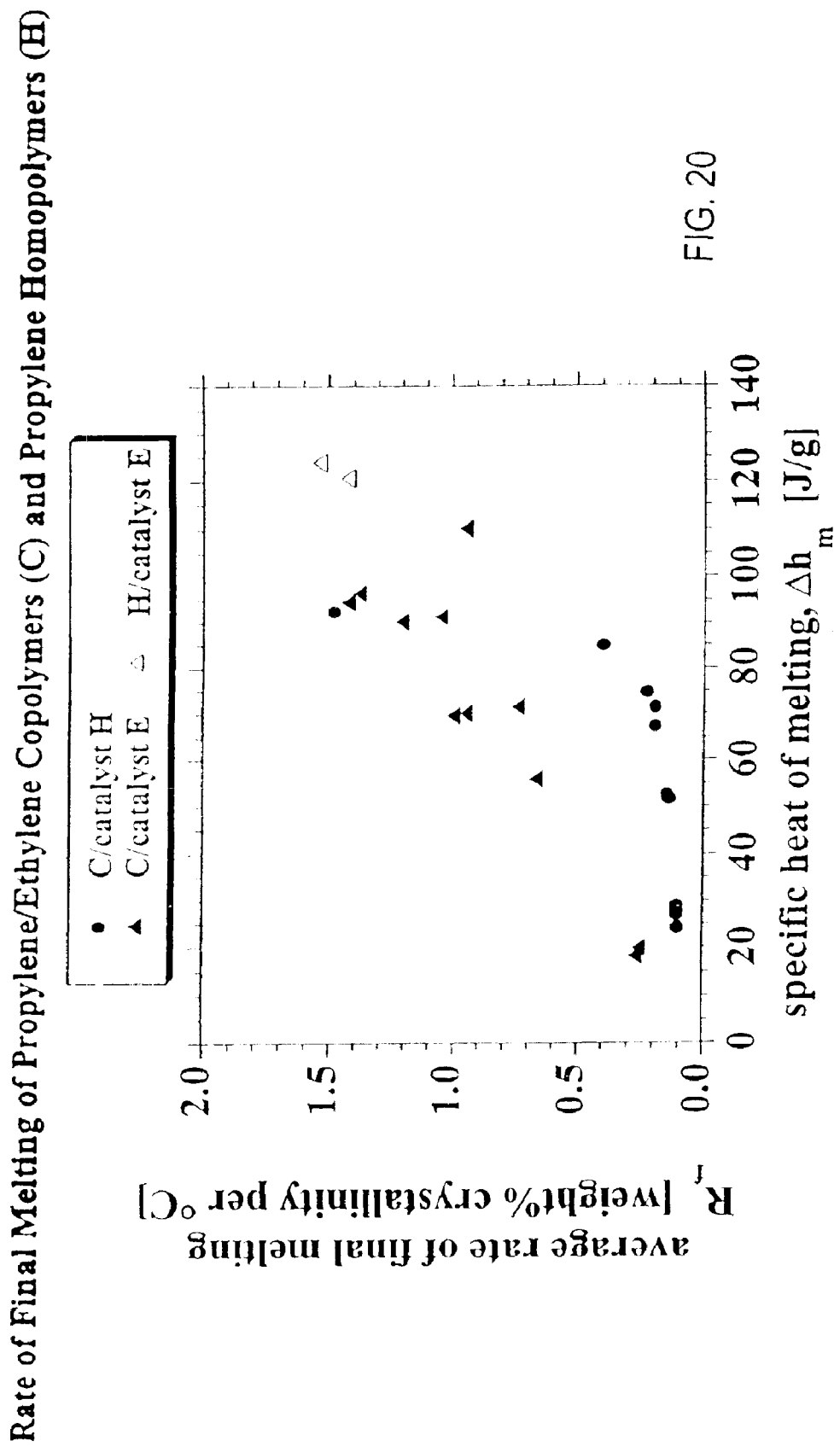
FIG. 20 illustrates that the rate at which the last portion of crystallinity disappears in P/E* polymers is significantly lower than for metallocene-catalyzed polymers.

FIG. 20 illustrates a useful aspect of the broader melting range of the inventive polymers, namely that the rate at which the last portion of crystallinity disappears (units: weight % crystallinity per ° C.) is significantly lower than for metallocene polymers.

The data in Table 11-2 demonstrate in practical terms the utility of this broadening of the melting endotherm. Entries in Table 11-2 illustrate: (1) the extent to which a greater fraction of melting occurs at lower temperatures, which is important for heat seal and bonding applications, and which is greater for the inventive copolymers; and (2) the extent to which crystallinity remains at higher temperatures and the rate at which the final portion of crystallinity disappears, which can be important for fabrication operations such as thermoforming, foaming, blow molding, and the like, both of which are greater for the inventive copolymers.

TABLE 11-1

Melting Results from DSC

| Sample* | ethylene (mole %) | $\Delta h_m$ (J/g) | $T_{max}$ (° C.) | $T_1$ (° C.) | $(dq/dt)_{max}/\Delta h_m$ (sec$^{-1}$) | $V_1$ (° C.$^2$) | $T_{1\%\,c}$ (° C.) | $R_f$ (**) |
|---|---|---|---|---|---|---|---|---|
| 11-1-1 | 0.0 | 90.4 | 139.0 | 123.5 | 0.0109 | 416 | 143.0 | 1.60 |
| 11-1-2 | 0.0 | 94.3 | 138.8 | 122.2 | 0.0105 | 505 | 143.1 | 1.54 |
| 11-1-3 | 0.0 | 94.0 | 139.4 | 122.4 | 0.0105 | 505 | 143.3 | 1.60 |
| 11-1-4 | 0.0 | 95.9 | 139.5 | 121.4 | 0.0102 | 576 | 143.4 | 1.60 |
| 11-1-5 | 1.5 | 92.4 | 138.2 | 118.4 | 0.0105 | 630 | 142.0 | 1.48 |
| 11-1-6 | 4.3 | 85.0 | 120.7 | 99.2 | 0.0045 | 716 | 135.0 | 0.40 |
| 11-1-7 | 8.2 | 67.5 | 85.9 | 83.8 | 0.0023 | 909 | 139.7 | 0.19 |
| 11-1-8 | 8.2 | 71.2 | 93.0 | 84.4 | 0.0025 | 835 | 137.5 | 0.19 |
| 11-1-9 | 8.2 | 74.6 | 108.2 | 87.0 | 0.0029 | 790 | 134.6 | 0.23 |
| 11-1-10 | 11.8 | 51.6 | 71.7 | 69.3 | 0.0024 | 790 | 124.4 | 0.14 |
| 11-1-11 | 11.8 | 52.5 | 74.8 | 69.4 | 0.0025 | 781 | 123.7 | 0.14 |
| 11-1-12 | 11.8 | 51.9 | 73.9 | 69.4 | 0.0025 | 802 | 124.3 | 0.14 |
| 11-1-13 | 15.8 | 24.0 | 55.2 | 66.7 | 0.0031 | 667 | 112.0 | 0.10 |
| 11-1-14 | 15.8 | 28.7 | 55.2 | 66.3 | 0.0026 | 795 | 118.0 | 0.10 |
| 11-1-15 | 15.8 | 27.6 | 55.6 | 66.0 | 0.0026 | 783 | 116.4 | 0.10 |
| 11-1-16 | 15.8 | 26.9 | 55.2 | 66.4 | 0.0026 | 769 | 115.7 | 0.10 |
| 11-1-17a | 0.0 | 120.7 | 160.3 | 145.3 | 0.0104 | 457 | 165.9 | 1.43 |
| 11-1-17b | 0.0 | 123.9 | 159.8 | 144.5 | 0.0105 | 486 | 165.2 | 1.54 |
| 11-1-18 | — | 90.3 | 140.6 | 125.0 | 0.0076 | 419 | 146.1 | 1.21 |
| 11-1-19 | — | 91.3 | 139.0 | 123.9 | 0.0068 | 374 | 145.5 | 1.05 |
| 11-1-20a | 4.2 | 110.2 | 137.7 | 121.8 | 0.0094 | 337 | 144.3 | 0.95 |
| 11-1-20b | 4.2 | 96.5 | 137.9 | 121.1 | 0.0100 | 451 | 142.7 | 1.38 |
| 11-1-21 | — | 94.6 | 136.7 | 120.3 | 0.0086 | 385 | 140.5 | 1.43 |
| 1-1-22a | 8.0 | 71.4 | 117.5 | 105.8 | 0.0081 | 197 | 124.8 | 0.74 |
| 11-1-22b | 8.0 | 69.7 | 117.0 | 103.4 | 0.0080 | 271 | 122.8 | 1.00 |

TABLE 11-1-continued

Melting Results from DSC

| Sample* | ethylene (mole %) | $\Delta h_m$ (J/g) | $T_{max}$ (° C.) | $T_1$ (° C.) | $(dq/dt)_{max}/\Delta h_m$ (sec$^{-1}$) | $V_1$ (° C.$^2$) | $T_{1\% c}$ (° C.) | $R_f$ (**) |
|---|---|---|---|---|---|---|---|---|
| 11-1-23 | — | 70.1 | 110.3 | 91.0 | 0.0062 | 512 | 115.9 | 0.95 |
| 11-1-24 | — | 55.9 | 97.0 | 78.7 | 0.0052 | 436 | 103.9 | 0.67 |
| 11-1-25 | — | 19.8 | 63.0 | 61.1 | 0.0044 | 188 | 80.1 | 0.25 |
| 11-1-26 | — | 18.2 | 56.6 | 58.8 | 0.0049 | 158 | 75.3 | 0.27 |

*Samples 11-1-1 to -4 made with catalyst G, samples -5 to -16 with catalyst H, and -17 to -24 with catalyst E.
** Units for $R_f$: weight % crystallinity per ° C.

TABLE 11-2

Broadening of the Melting Endotherm

| Sample | Starting Crystallinity (weight %) | fraction melted at $T_1 - 30°$ C. | fraction melted at $T_1 - 20°$ C. | fraction remaining at $T_1 + 20°$ C. | fraction remaining at $T_1 + 30°$ C. |
|---|---|---|---|---|---|
| 11-2-8 (inventive) | 43.2 | 0.153 | 0.229 | 0.249 | 0.134 |
| 11-2-22a (comparative) | 43.3 | 0.040 | 0.112 | 0.019 | 0.004 |
| 11-2-11 (inventive) | 31.8 | 0.143 | 0.235 | 0.221 | 0.131 |
| 11-2-25 (comparative) | 33.9 | 0.103 | 0.170 | 0.127 | 0.009 |

EXAMPLE 12

Figure 10:
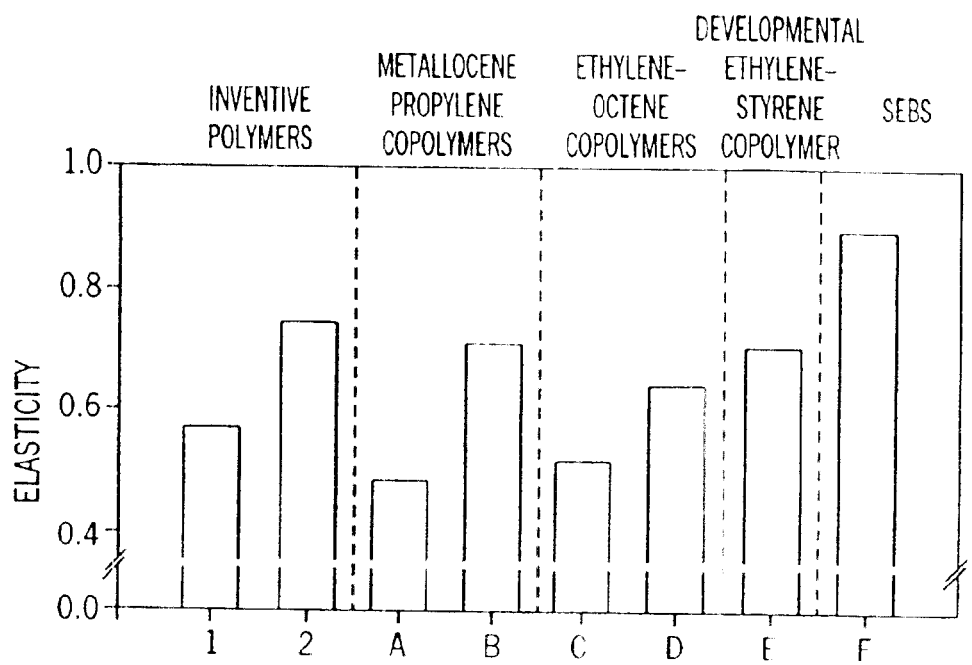
FIG. 10 is a bar graph comparing the elasticity of unstretched P/E* copolymers against various conventional unstretched thermoplastic elastomers.
Figure 11:
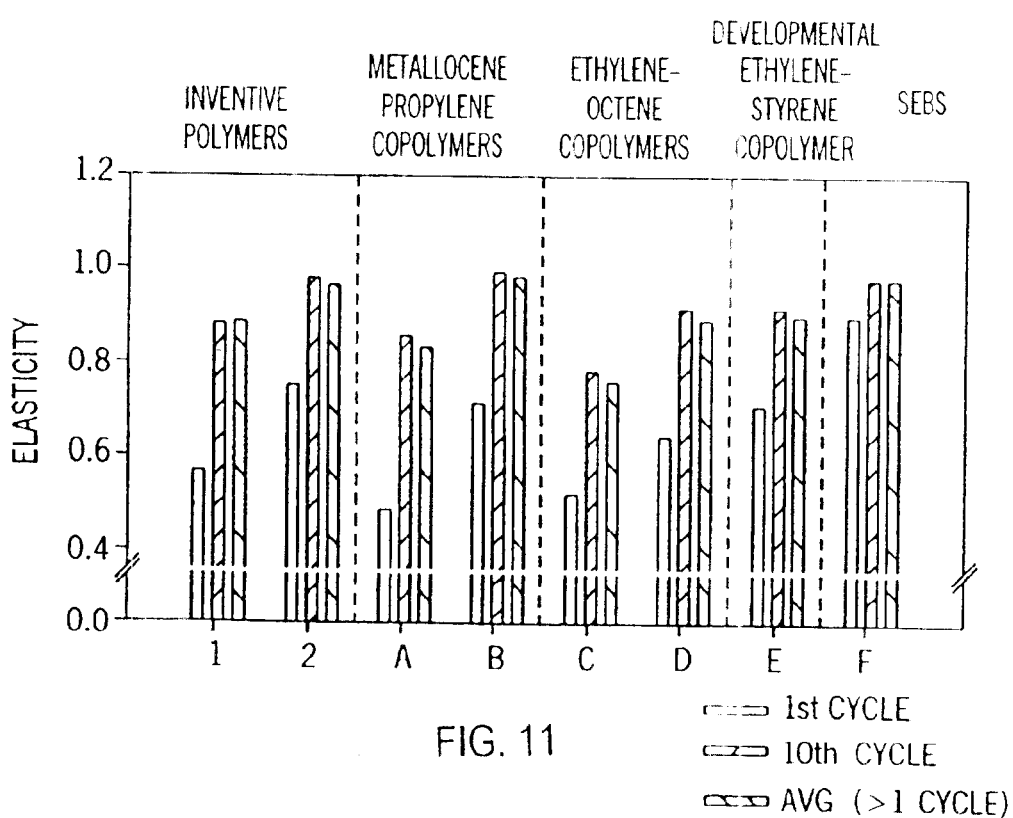
FIG. 11 is a bar graph comparing the elasticity of pre-stretched P/E* copolymers against various conventional pre-stretched thermoplastic elastomers.
Figure 12A:
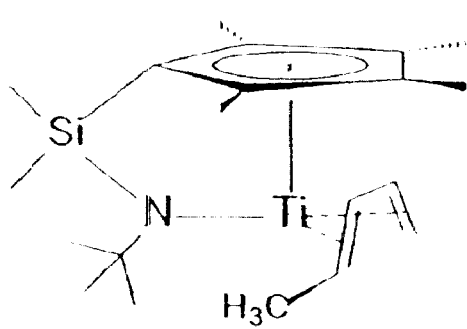
FIGS. 12A–12J show the chemical structures of various catalysts.
Figure 12B:
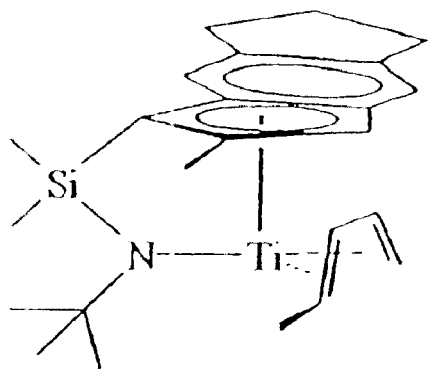
Figure 12C:
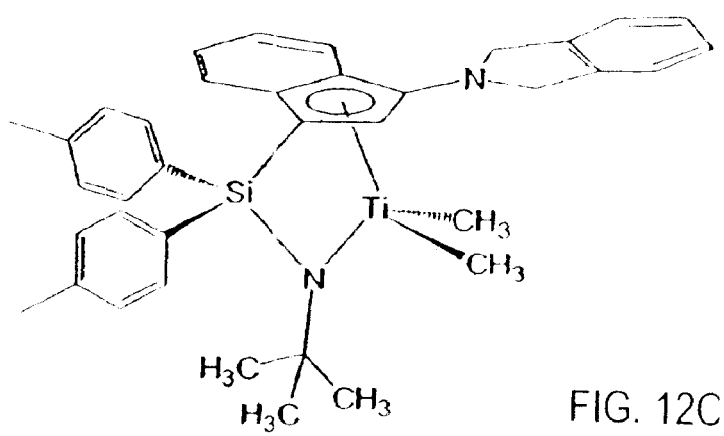
Figure 12D:
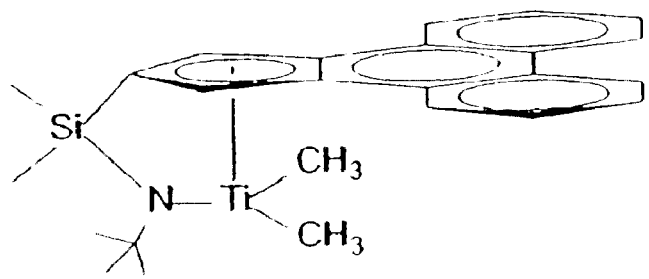
Figure 12E:
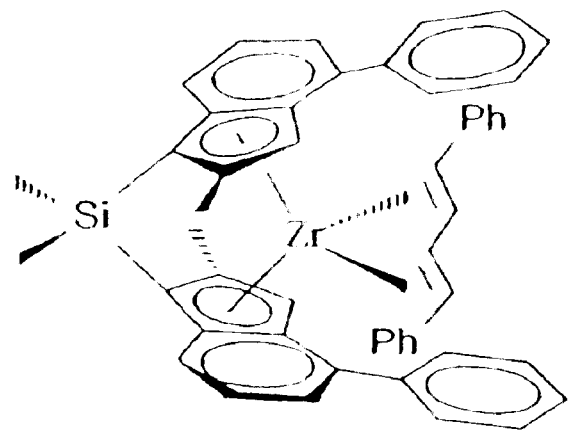
Figure 12F:
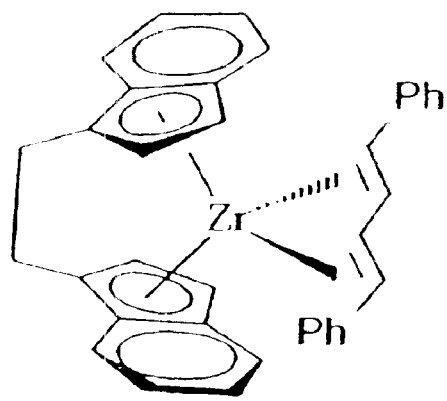
Figure 12G:
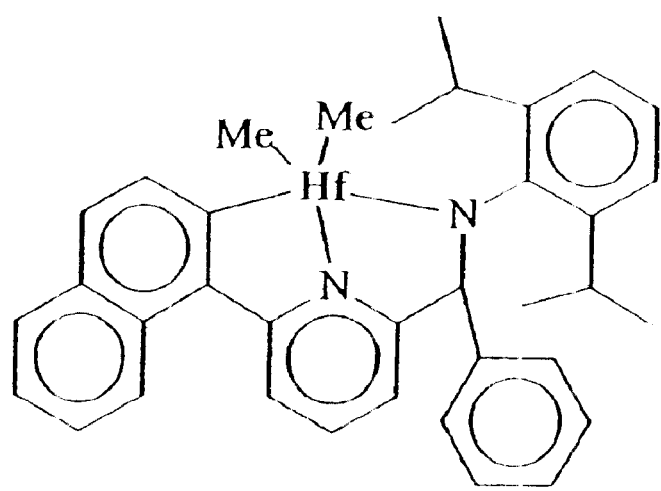
Figure 12H:
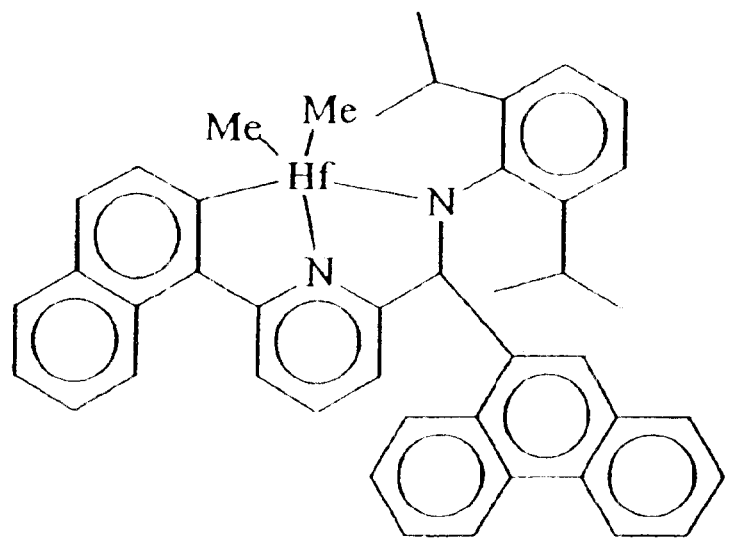
Figure 12I:
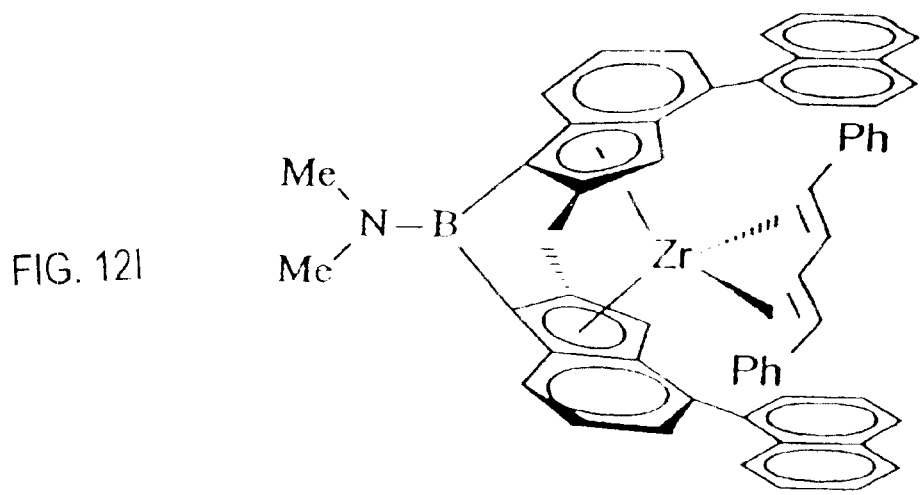
Figure 12J:
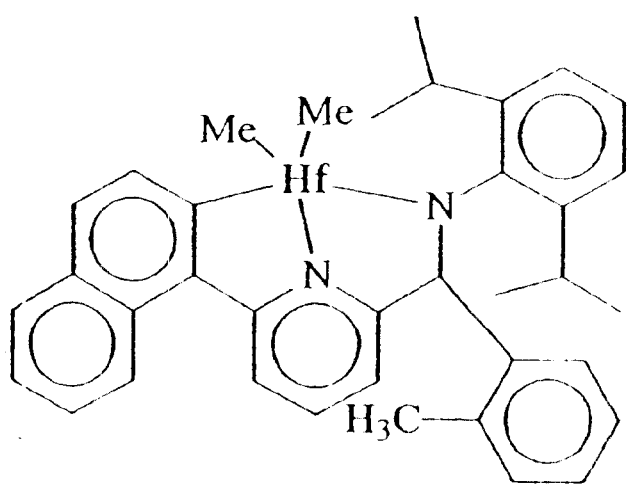

FIGS. 10 and 11 report certain elasticity data for the polymers of this invention and certain comparative polymers. Table 12-1 describes the elastomers.

The test samples were compression molded specimens. Polymer in pellet form was compression molded at 190 C into 1.5 mm thick sheets. The sheets were cooled by placing each between two platens at 25 C under light pressure. The specimens were allowed to age for at least seven days at ambient conditions before testing.

Tensile "dog bones" were punched out of the sheets using a knife shaped according to ASTM D-1708. The first melting behavior was measured by cutting out a 5 to 10 mg piece of the aged specimen. The specimen was loaded into an aluminum pan and analyzed in a differential scanning calorimeter manufactured by TA Instruments Incorporated. Heating spanned −50 to 230 C at 10 C/min.

The specimens were tested in uniaxial tension with a mechanical test device (Instron Corp.) fitted with pneumatic grips. The engineering strain rate was 400% per minute. Both strain to break and multicycle loading strain histories were used. In the case of multicycle loading, specimens were loaded and unloaded to various strains (100 to 900%) for up to 10 cycles. No pause was used between successive cycles.

Table 12-2 reports the data in FIGS. 10 and 11. The data in Table 12-2 reports elasticity versus crystallinity for the same group of elastomers. Crystallinity is an important property in elastomeric applications because it controls to a large extent the stiffness (i.e., modulus) of a material. The virgin or unstretched metallocene polypropylenes exhibit elasticity versus crystallinity similar to the homogeneous polyethylene and ethylene-stryene elastomers, while the elastomeric polymers of this invention exhibit higher elasticity at the same crystallinity. Even after pre-stretching, the elastomeric polymers of this invention continue to exhibit superior elasticity at the same crystallinity as compared to both the metallocene propylenes and the homogeneous polyethylene and ethylene-stryene elastomers. The polymers of this invention demonstrate similar elasticity after stretching as do commercial grade SEBS polymers, e.g., Krayton G-1657.

TABLE 12-1

Elastomers

| Samples | Polymer Description | Comonomer (wt. %) | Comonomer (mol %) | DSC Crystallinity (wt. %) |
|---|---|---|---|---|
| 1 | P/E* polymer | 11 | 16 | 18 |
| 2 | P/E* polymer | 13 | 19 | 10 |
| A | metallocene-catalyzed propylene-ethylene copolymer | — | — | 21 |
| B | metallocene-catalyzed propylene-ethylene copolymer | — | — | 4 |
| C | ethylene-octene copolymer | 41 | 15 | 14 |
| D | Affinity EG8100 | 35 | 12 | 6 |
| E | ethylene-styrene copolymer | 41 | 16 | 5 |
| F | Kraton G-1657 (SEBS) | — | — | — |

TABLE 12-2

Elasticity Values of the Data in FIGS. 10 and 11

| Polymer | Virgin 1st cycle | Pre-stretched 10th cycle | average (>1 cycle) |
|---|---|---|---|
| 1 | 0.57 | 0.88 | 0.88 |
| 2 | 0.75 | 0.97 | 0.97 |
| A | 0.49 | 0.85 | 0.83 |
| B | 0.71 | 0.99 | 0.99 |
| C | 0.52 | 0.78 | 0.76 |
| D | 0.64 | 0.92 | 0.89 |
| E | 0.71 | 0.92 | 0.90 |
| F | 0.90 | 0.98 | 0.99 |

EXAMPLE 13

The P* and P/E* polymers reported in Table 13-1 (Samples 13-1 through 13-4 were prepared with Catalyst J in a solution polymerization process) were fed into a Killion blown film line available from Killion Extruders INC. under model designation KN-125. During the film blowing, the Killion line was equipped with a 1.5 inch (3.81 cm) diameter screw, 3 inch (7.62 cm) die diameter, and a 70 mil (1778 micron) die gap. The extruder is 50 inch (125 cm) long with a length to diameter ratio (L/D) of 30. The temperature profile is listed as follows: 370, 370, 380, 380, 390, 425, 395, 396 F for zone 1, 2, 3, 4, screen changer, die 1 and die 2. The melt temperature is about 425 F (218.2 C) with a blow up ratio (BUR) of 2.0 and an output rate of 10 lb/h. The screw speed was 65 rpm, the back pressure 1650 psi, the screw amperage 7 amp, and the layflat about 9.5 inches.

The resulting films were 2.0 mil (50 micron) in thickness and film properties were measured according to standard ASTM methods as shown in Table 13-2.

For comparison, various commercially or experimentally available Ziegler-Natta catalyzed random polypropylene resins, also shown in Table 1 (Samples 13-1-C through 13-5-C), were also fabricated with Killion line under similar operating parameters as above. Film properties were also measured according to standard ASTM methods as shown in Table 13-2.

Film properties for all above films are shown in Table 13-3. As can be seen from these data, P/E* copolymer films in which the P/E* copolymer comprises at least 5 wt % ethylene have a machine direction (MD) tear greater than 100 g/mil. In addition, those P/E* copolymer films in which the P/E* copolymer comprises at least 5 wt % ethylene have a haze value of less than 10%, and a 45 degree gloss greater than 65%. The dart impact strength of these films is greater than 200 g.

TABLE 13-1

| Resin I | MFR | Co-monomer type | Co-monomer % |
|---|---|---|---|
| 13-1-1 | 2 |  | 0 |
| 13-1-2 | 2 | Ethylene | 3 |
| 13-1-3 | 2 | Ethylene | 5 |
| 13-1-4 | 2 | Ethylene | 8 |
| 13-1-1-C | 2 | Ethylene | 0.5 |
| 13-1-2-C | 2 | Ethylene | 3.2 |
| 13-1-3-C | 7 | Ethylene | 5.5 |
| 13-1-4-C | 2 | Ethylene | 3 |
| 13-1-5-C | 5 | 1-Butene | 12 |

TABLE 13-2

Test Methods

| Test | Methods |
|---|---|
| Dart-A | ASTM D-1709 |
| Elmendorf Tear-B | ASTM D1922 |
| Haze | ASTM D1003 |
| Tensile, | ASTM D882 |
| Gloss-45 degree | ASTM D2457 |
| MFR | ASTM 1238 |

TABLE 13-3

Film Property Comparison

| Resin/ properties | wt % comonomer | MD-tear, g | CD-tear, g | Dart, g | Haze, % | Gloss-45 | Normalized MD-tear, g/mil |
|---|---|---|---|---|---|---|---|
| 13-1 | 0 | 13 | 25 | 60 | 28 | 30 | 7 |
| 13-2 | 3 | 16 | 52 | 60 | 5.5 | 75 | 8 |
| 13-3 | 5 | 290 | 1063 | 640 | 5 | 74 | 145 |
| 13-4 | 8 | 740 | 1327 | 756 | 2 | 88 | 375 |
| 13-1-C | 0.5 | 14 | 46 | 60 | 34 | 23 | 7 |
| 13-2-C | 3 | 19 | 56 | 60 | 2.4 | 88 | 9 |
| 13-3-C | 3.2 | 14.8 | 60 | 60 | 16.3 | 44.1 | 9 |
| 13-4-C | 5.5 | 33 | 48 | 69 | 6.8 | 72.5 | 16 |
| 13-5-C | 12 | 23 | 43 | 68 | 10 | 68 | 12 |

EXAMPLE 14

A commercially available Ziegler-Natta polypropylene, nucleated NA-11 (methylene-bis-(4,6-di-tert-butylphenyl) phosphate sodium salt manufactured by Asahi Denka), was used as a base resin for a blending study. Various P/E* copolymers and commercially available polyethylene resins were melt blended with the Z-N PP at a ratio indicated in Table 14. The melt-blended materials were then fed into the Killion line described in Example 13 to produce blown films. The film properties were measured as described in Example 13.

The film properties for these blended films are shown in Table 14. The films made by blending the P/E* copolymer into Z-N PP and comprising P/E* copolymer and that have at least 5 wt % of ethylene in the overall blend have machine direction tear greater than 100 g/mil. In addition, these P/E* copolymer films comprising at least 5 wt % ethylene have a haze value less than 10%, a 45 degree gloss greater than 65%, and dart impact strength greater than 200 grams.

TABLE 14

| Result Name | Ex 14-A H110/50% (13 wt % E) | Ex 14-B H110/50% (11 wt % E) | Ex 14-C H110/70% (11 wt % E) | Comp-1 H110-02 | Comp-2 H110/30% PF1140 |
|---|---|---|---|---|---|
| Gloss 45 deg | 83.4 | 82.1 | 75.8 | 63.6 | 74.3 |
| Haze | 4.1 | 3.3 | 5.3 | 7.9 | 5.1 |
| Dart A | 486.0 | 433.5 | 600.5 | 60.0 | 60.0 |
| CD-tear, | 500.7 | 546.0 | 758.2 | 38.7 | 118.0 |
| Thickness | 2.8 | 3.0 | 2.7 | 1.9 | 1.8 |
| Normalized CD-tear, g/mil | 181.2 | 185.5 | 285.2 | 20.1 | 65.1 |
| MD-tear, g | 582.8 | 1065.0 | 696.4 | 16.0 | 17.2 |
| Thickness, mil | 2.95 | 2.84 | 2.66 | 1.95 | 1.58 |
| Normalized MD-tear, g/mil | 197.7 | 377.6 | 265.4 | 8.3 | 11.0 |

H110 is a Z-N random PP containing 0.5 wt % ethylene, an MFR of 2 and nucleated with 1000 ppm NA-11.
PF1140 is an ethylene-octene copolymer with a density of 0.896 g/cc and an MI of 1.6 manufactured by The Dow Chemical Company.

EXAMPLE 15

Figure 21:
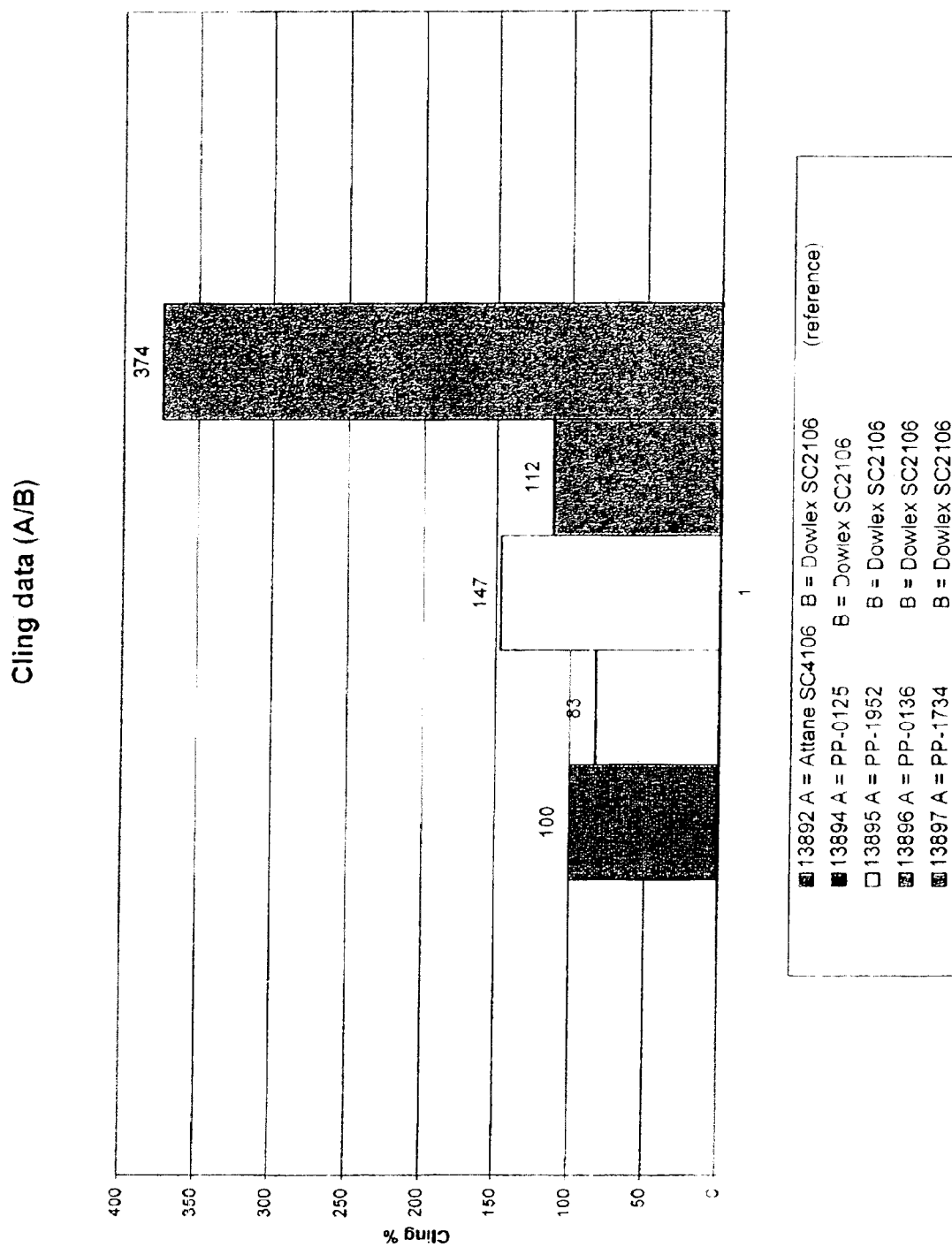
FIG. 21 illustrates the cling percent for two A/B film structures tested with the A layer of the first film in contact with the B layer of the second film, in which the A layers in both structures are made from a P/E* copolymer.
Figure 22:
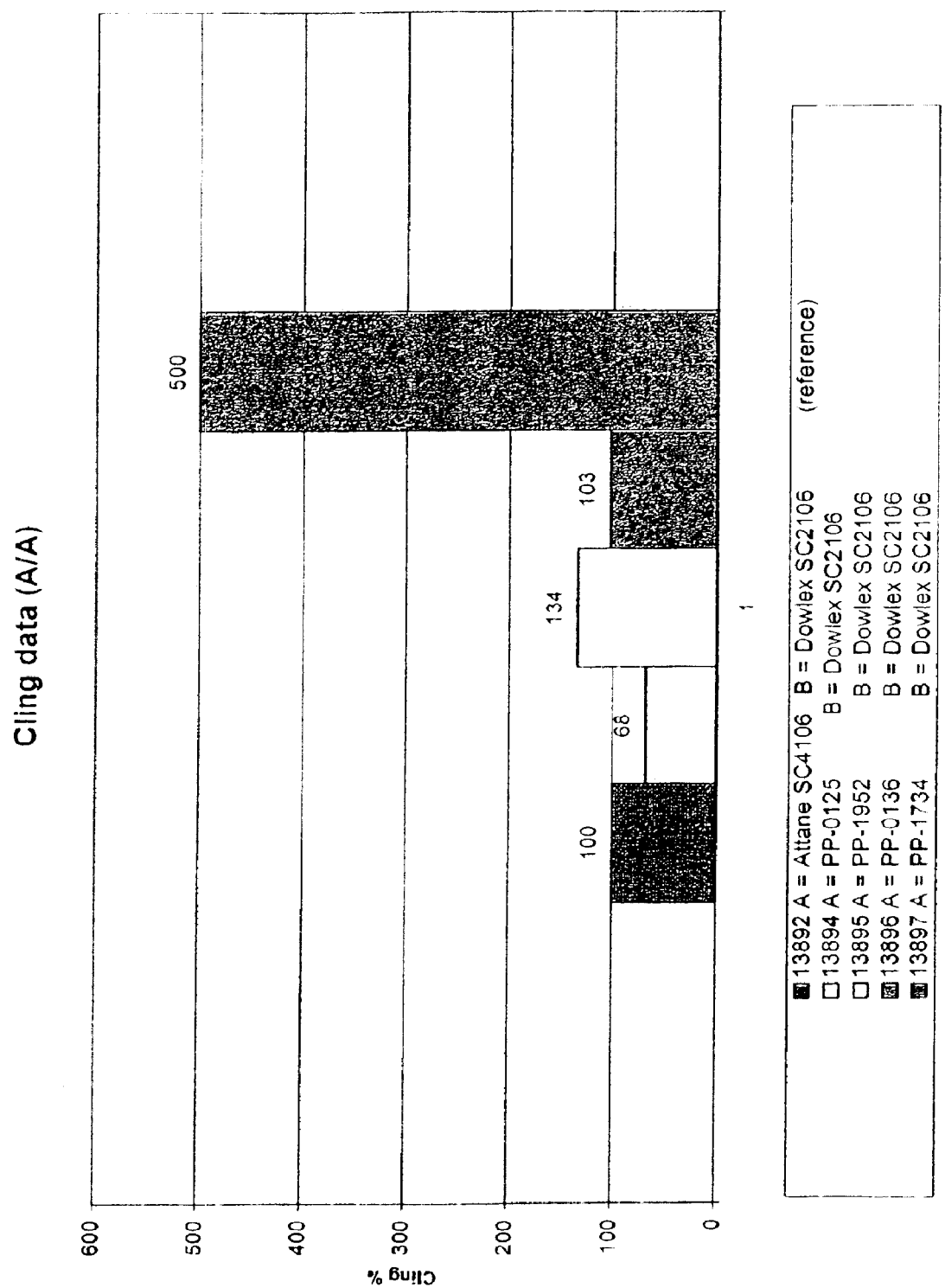
FIG. 22 illustrates the cling percent for two A/B film structures tested with the A layer of the first film in contact with the A layer of the second film. Both A layers are made from a P/E* copolymer.

The data in Tables 15-1 and 15-2 and FIGS. 21 and 22 show that the films of this invention exhibit desirable cling properties when attached to either another film of this invention or a film of polyethylene. The films had an A/B structure with the A layer comprising 15 wt % of the film. The films were 23–27 microns thick. The A layer was the cling layer. The films were tested for cling in accordance with ASTM D4649.

Table 15-1 shows the cling values when two A/B film structures were tested with the A layer of the first film in contact with the B layer of the second film. The clings values were normalized to make 100% cling values for Film Nos. 15-1-AB and 15-2-AB.

The resins identified as PP-0125, 1952, 0136 1734 are P/E* copolymers made in a solution polymerization process using Catalyst J. The Attane SC 4106 is a polyethylene resin with an MFR of 3.3 g/10 min and a density of 0.912 g/cc, and the Attane SC 4107 is a polyethylene resin with an MFR of 4 g/10 min and a density of 0.904 g/cc. DOWLEX SC 2106 is a polyethylene resin with an MFR of 3.3 g/10 min and a density of 0.917 g/cc. All three MFR's are measured at 190 C and are manufactured by The Dow Chemical Company.

TABLE 15-1

Cling Properties. B/A-B/A Test

| Film No. | Resin A | Resin B | Cling % |
|---|---|---|---|
| 15-1-AB | Attane SC4106 | Dowlex SC2106 | 100 |
| 15-2-AB | Attane SC4107 | Dowlex SC2106 | 100 |
| 15-3-AB | PP-0125 (5% E; MFR 8) | Dowlex SC2106 | 83 |
| 15-4-AB | PP-1952 (8% E; MFR 8) | Dowlex SC2106 | 147 |
| 15-5-AB | PP-0136 (3% E; MFR 25) | Dowlex SC2106 | 112 |
| 15-6-AB | PP-1734 (11% E; MFR 25) | Dowlex SC2106 | 374 |

Table 15-2 shows the cling values when two A/B film structures were tested with the A layer of the first film in contact with the A layer of the second film. The clings values were normalized to make 100% cling values for Film Nos. 15-1-AA and 15-2-AA.

TABLE 15-2

Cling Properties, B/A-A/B Test

| Film No. | Resin A | Cling % |
|---|---|---|
| 15-1-AA | Attane SC4106 | 100 |
| 15-2-AA | Attane SC4107 | 100 |
| 15-3-AA | PP-0125 (5% E; MFR 8) | 68 |
| 15-4-AA | PP-1952 (8% E; MFR 8) | 134 |
| 15-5-AA | PP-0136 (3% E; MFR 25) | 103 |
| 15-6-AA | PP-1734 (11% E; MFR 25) | 500 |

EXAMPLES 16 and 17

P/E* Containing Sealant Compositions

The following examples show the use of the P/E* polymers of the invention as sealant compositions for sealing applications. The sealant applications include, but are not limited to, films, laminates, and other articles for use in such applications as, biaxially oriented polypropylene film processes (BOPP) film sealants, cast film sealants, tie-layer for various film and laminate structures, such as bags, sacks, wraps, surface contact protecters, and snacks containers. The films can be monolayer or multilayer and may be formed by various processes, such as, blown film processes, calandered film processes, cast film processes, BOPP, tenter film processes, and sheet and profile extrusion processes.

The sealant compositions may be comprised of P/E* polymers alone, or may be comprised of P/E* polymers blended with other alpha-olefin homopolymers and/or copolymers. The preferable alpha-olefin polymers to blend with the P/E* polymers are propylene homopolymers, copolymers of propylene and other alpha-olefins, such as ethylene, 1-butene, 1-pentane, 1-hexane, 4-methyl pentane, 1-heptane, and 1-octene.

When used alone for the sealant compositions, the P/E* polymers preferably have at least 3% by weight of units derived from ethylene, more preferably at least about 5% by weight of units derived from ethylene, further more preferably from about 6 wt. % to 10 wt % units derived from ethylene, most preferably from about 7 wt. % to 9 wt % units derived from ethylene.

When blended with another propylene ethylene copolymer, the blend preferably has from about 4 wt % to 9 wt % of units derived from ethylene, more preferably, from about 5 wt % to 9 wt % of units derived from ethylene, and the P/E* polymer preferably has from about 7 wt % to 15 wt % of units derived from ethylene, more preferably from about 8 wt % to 14 wt % of units derived from ethylene, further more preferably from about 9 wt % to 13 wt % of units derived from ethylene, most preferably from about 10 wt % to 12 wt % of units derived from ethylene.

For the following examples, the hot tack of the films was measured using the "JB Instrument Hot Tack Test Method," which measures the force required to separate a heat seal before the seal has had a chance to fully cool (crystallize). This test simulates the filling of material into a pouch or bag before the seal has had a chance to completely cool.

The "JB Instrument Hot Tack Test Method" is a test method using a JB Instrument Hot Tack Tester according to the following conditions:

| | |
|---|---|
| Speciment Width: | 25.4 mm |
| Sealing Time: | 0.5 seconds |
| Sealing Pressure: | 0.27 N/mm/mm |
| Delay Time: | 0.2 seconds |
| Peel Speed: | 250 mm/seconds |
| Number of Samples per Temperature | 5 |
| Temperature Increments: | 5° C. |

The heat seal strength of sample films was measured using the "JB Instrument Heat Seal Strength Test Method," which is designed to measure the force required to separate a seal after the material has completely cooled to 23° C. The film samples were exposed to a relative humidity of 50 percent and a temperature of 23° C. for a minimum of 24 hours prior to testing.

The seal strength of the film samples was determined using an Instron Tensile Tester Model #1122 according to the following test conditions:

| | |
|---|---|
| Direction of Pull: | 90° to seal |
| Crosshead Speed: | 500 mm/minute |
| Full Scale Load: | 5 kg |
| Number of Samples/Threshold: | 1 percent of FSL |
| Break Ciiterion: | 80 percent |
| Gauge Length: | 2.0 inches (50.8 millimeters) |
| Sample Width: | 1.0 inch (25.4 millimeters) |

Heat seal initiation temperature is defined as the minimum temperature for 2 lb/in (0.4 Kg/cm) seal strength.

All of the films of Examples 16 and 17 are blown films made in accordance with the descriptions set forth in Examples 13 and 14.

The following resins were used in Examples 16 and 17:

A. P/E* S1 is a propylene ethylene copolymer containing 3 wt % of units derived from ethylene and is made with Catalyst J using a loop polymerization process as described in U.S. Pat. No. 5,977,251.

B. P/E* S2 is a propylene ethylene copolymer containing 5 wt % of units derived from ethylene and is made with Catalyst J using a loop polymerization process as described in U.S. Pat. No. 5,977,251.

C. P/E* S3 is a propylene ethylene copolymer containing 8 wt % of units derived from ethylene and is made with Catalyst J using a loop polymerization process as described in U.S. Pat. No. 5,977,251.

D. P/E* S4 is a propylene ethylene copolymer containing 11 wt % of units derived from ethylene and is made with Catalyst J using a loop polymerization process as described in U.S. Pat. No. 5,977,251:

E. P/E* S5 is a propylene ethylene copolymer containing 13 wt % of units derived from ethylene and is made with Catalyst J using a loop polymerization process as described in U.S. Pat. No. 5,977,251.

F. H308–02Z is a Z-N catalyzed random copolymer of propylene and ethylene having 0.5 wt % units derived from ethylene available from The Dow Chemical Company. Propylene-ethylene copolymers having less than 1 wt % of units derived from ethylene are sometimes hereinafter referred to as "mini-random propylene-ethylene copolymers".

G. SR256M is a Z-N catalyzed random copolymer of propylene and ethylene having 3 wt % units derived from ethylene available from Basell. These types of random copolymers are often referred to as "RCP PP".

H. PF1140 is a single-site catalyzed ethylene/1-octene copolymer having a melt index of 1.6 and a density of 0.896 g/cc and which is available from The Dow Chemical Company.

I. H 10-02Z is a Z-N catalyzed random copolymer of propylene and ethylene having 0.5 wt % units derived from ethylene and 1000 ppm NA-11 nucleator (available from Asahi-Denka) which is available from The Dow Chemical Company.

EXAMPLE 16

P/E* Sealants

Figure 23:
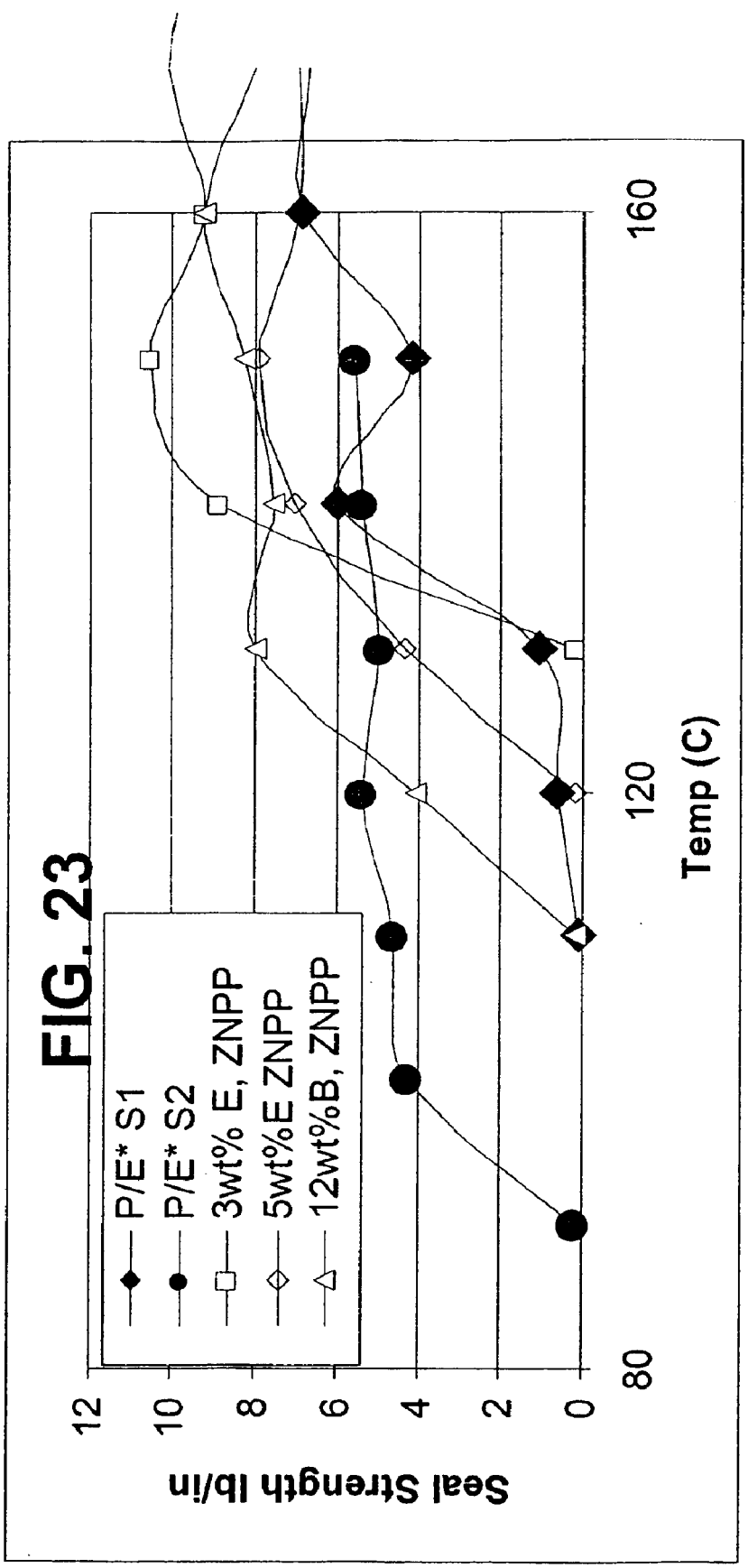
FIG. 23 shows the heat seal behavior for the P/E* polymers compared to Ziegler-Natta catalyzed polymers ("ZN catalyzed polymers").

Referring to FIG. 23, it can be seen that P/E* resins having 5 wt % of units derived from ethylene have much better heat seal behavior than typical Z-N-catalyzed propylene-ethylene copolymers (designated as 3 and 5 wt % E, ZNPP) and even exhibits better heat seal behavior than a Z-N-catalyzed propylene-1-butene copolymer (designated as 12 wt % B, ZNPP) having 12 wt % of units derived from 1-butene. Significantly, the P/E* resin exhibits a heat seal initiation temperature of 100 C.

Figure 24:
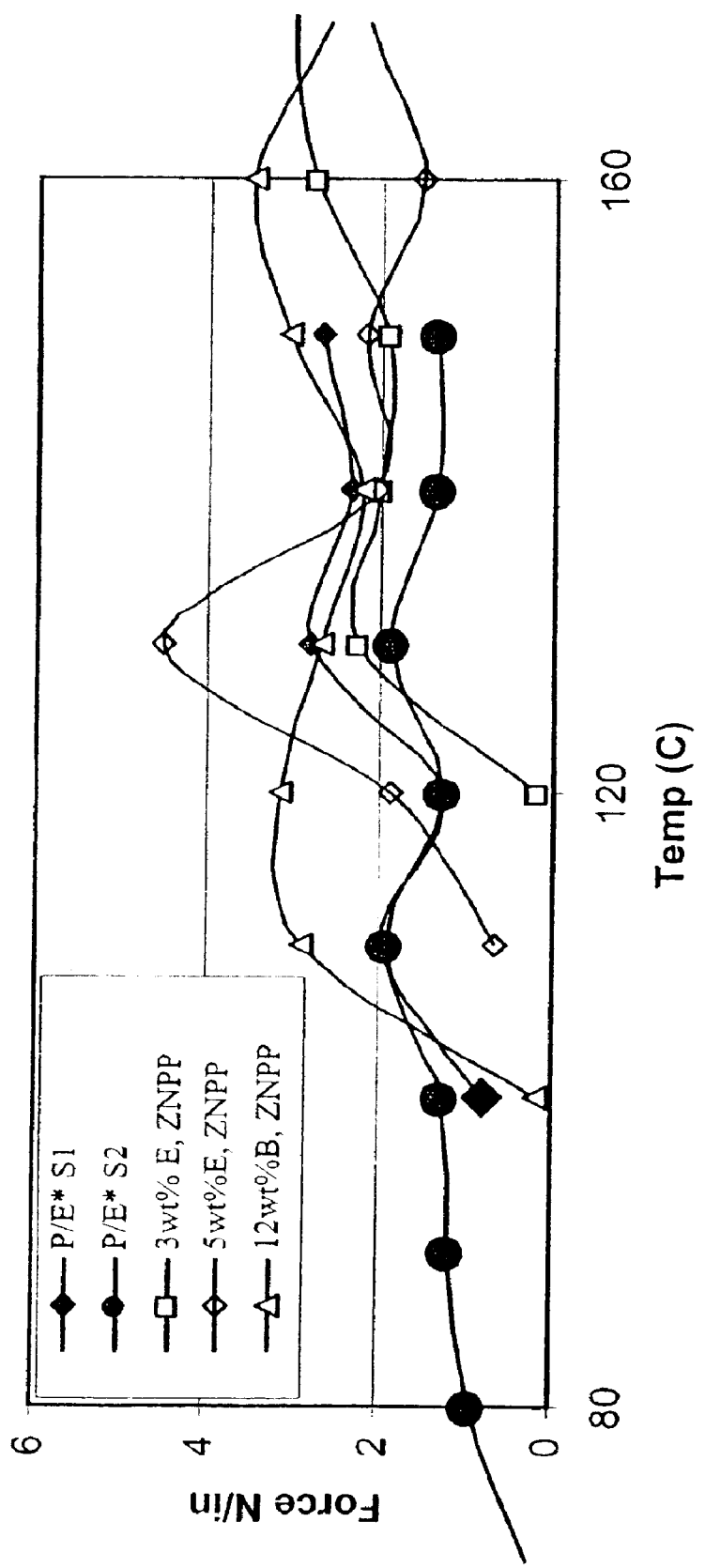
FIG. 24 shows the hot tack behavior for the P/E* polymers compared to Ziegler-Natta catalyzed polymers.

Referring to FIG. 24, it can be seen that the hot tack window for the P/E* resins is broader than typical Z-N-catalyzed propylene-alpha-olefin copolymers.

EXAMPLE 17

P/E*/Alpha Olefin Polymer Blends

Figure 25:
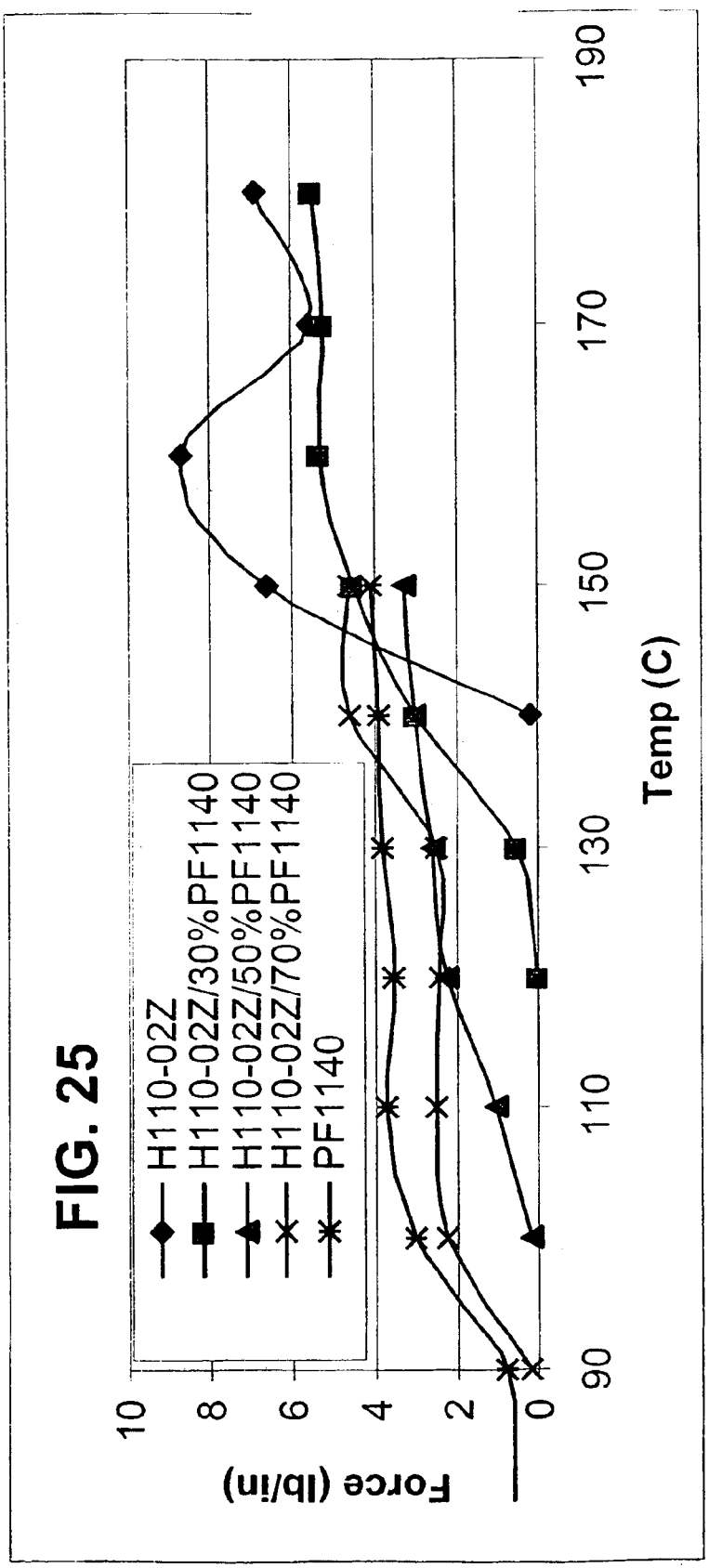
FIG. 25 shows the heat seal behavior for blends of propylene-ethylene copolymers with metallocene catalyzed ethylene/alpha-olefin copolymer.

Referring to FIG. 25, it can be seen that the heat seal behavior of a blend of Z-N-catalyzed mini-random propylene-ethylene copolymer and an ethylene/1-octene copolymer normally behaves according to the weighted average of the components of the blend. In particular, the heat seal initiation temperature of such blends is normally much reduced compared to the heat seal initiation temperature of the mini-random alone.

Figure 26:
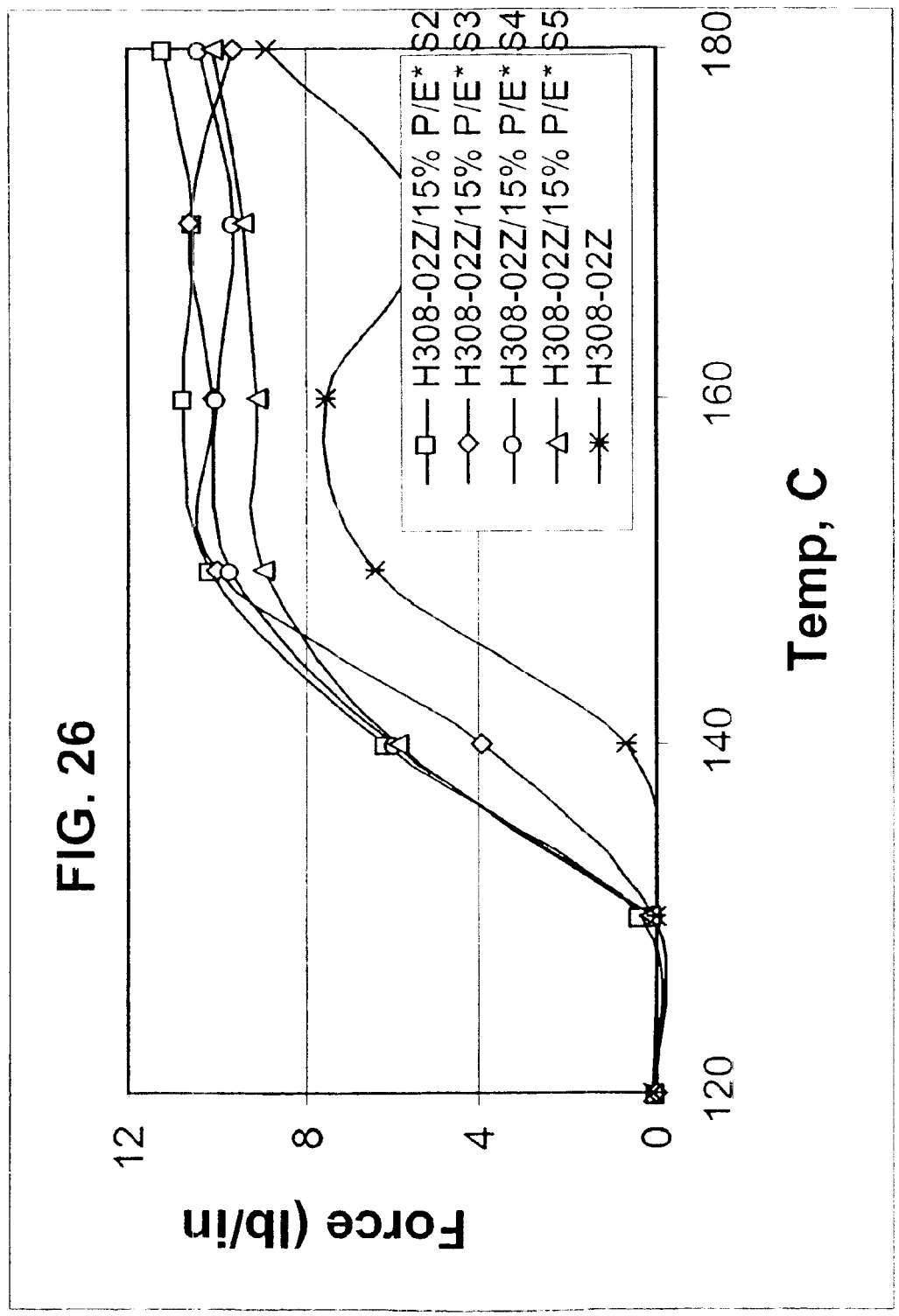
FIG. 26 shows the heat seal behavior for blends of mini-random propylene-ethylene copolymers with P/E* copolymers.
Figure 27:
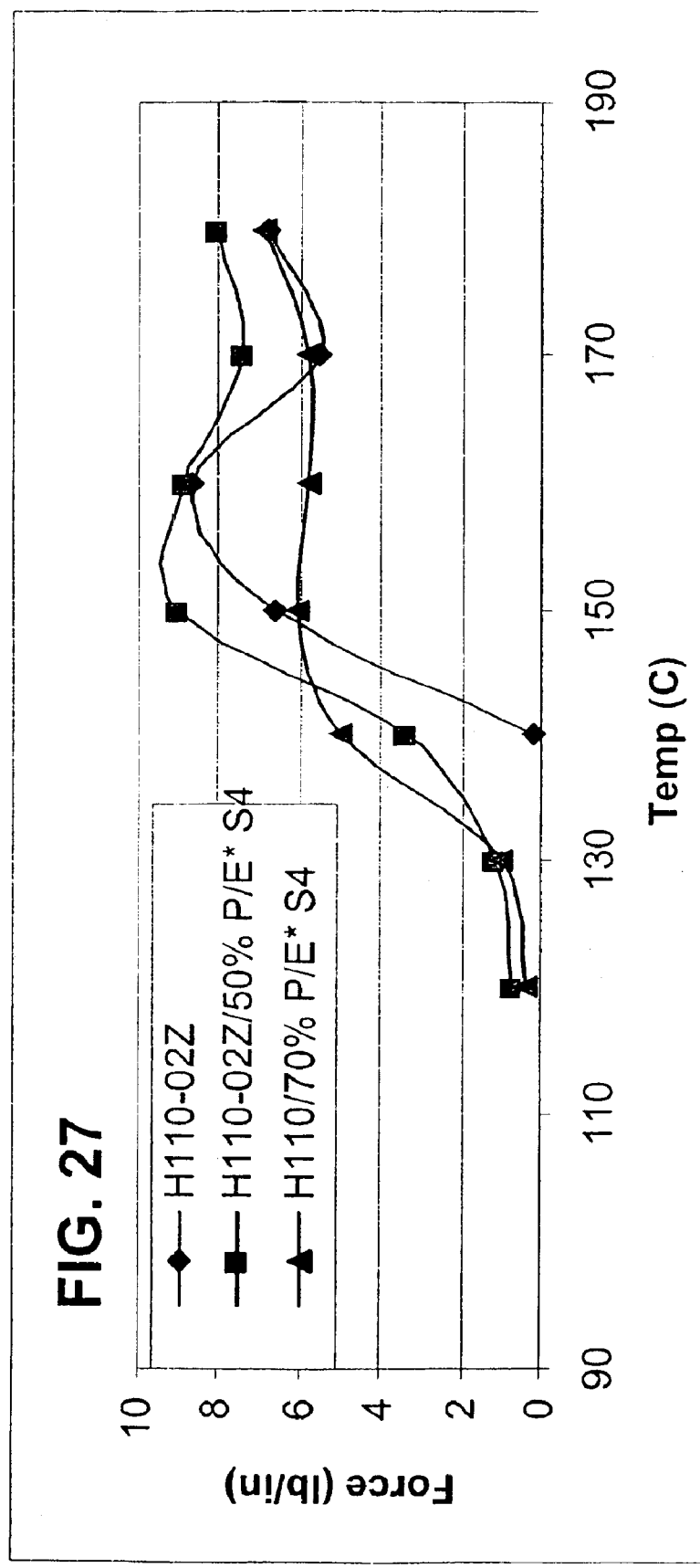
FIG. 27 shows the heat seal behavior for blends of P/E* copolymers with a mini-random propylene-ethylene copolymer.

Referring to FIGS. 26 and 27, it can be seen that the P/E* polymers do not follow the normal blending rules when blended with a mini-random propylene ethylene copolymer. It can be seen from FIGS. 26 and 27 that the heat seal behavior of blends of P/E* copolymer with propylene homopolymers and with mini-random propylene-ethylene copolymers are relatively insensitive to the ethylene content of the P/E* copolymer and/or the amount of P/E* copolymer that makes up the blend.

Figure 28:
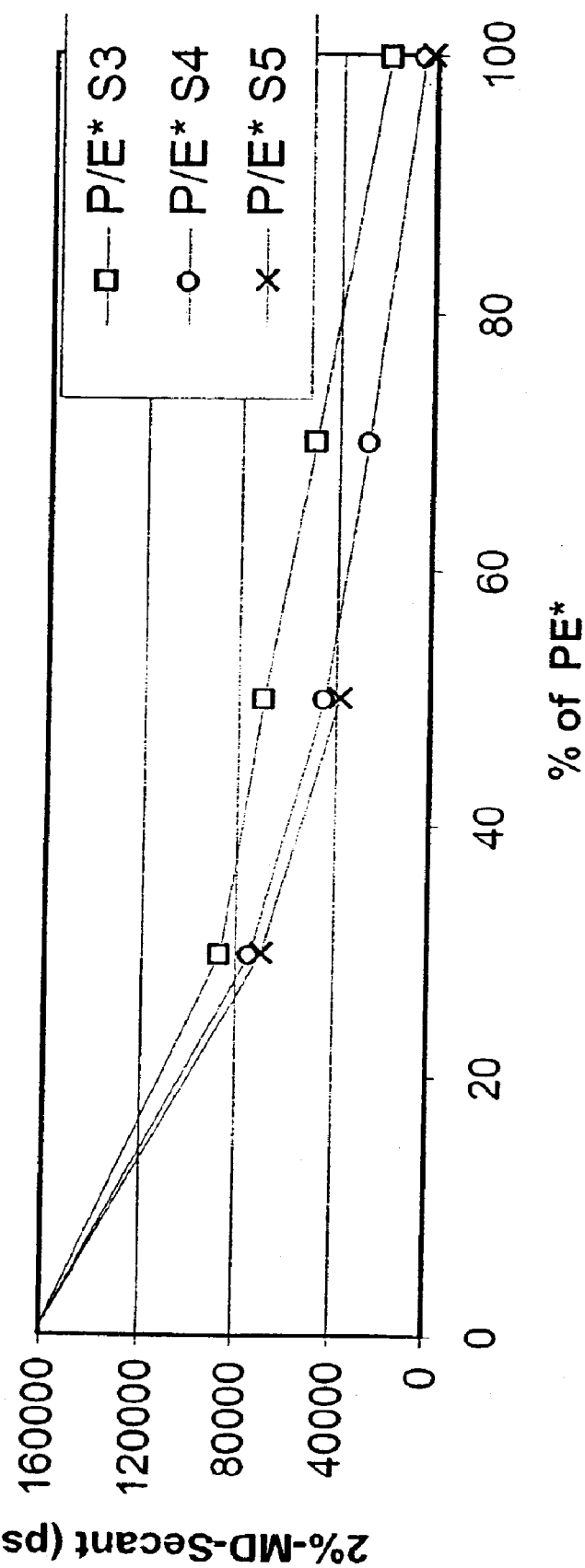
FIG. 28 shows the 2% secant modulus (as determined by ASTM D882) for blends of P/E* copolymers with a mini-random propylene-ethylene copolymers.

FIG. 28 shows that the modulus of the blend decreases as the wt % of P/E* copolymer in the blend increases. FIGS. 26–28 together show that a lower modulus sealant composition can be made with P/E* copolymers that will have a relatively high heat seal initiation temperature. The lower modulus will result in less stiff articles of manufacture. This is particularly important for retort applications and like applications where a higher heat seal initiation temperature is desired, but a stiff sealing area is undesirable.

Figure 29:
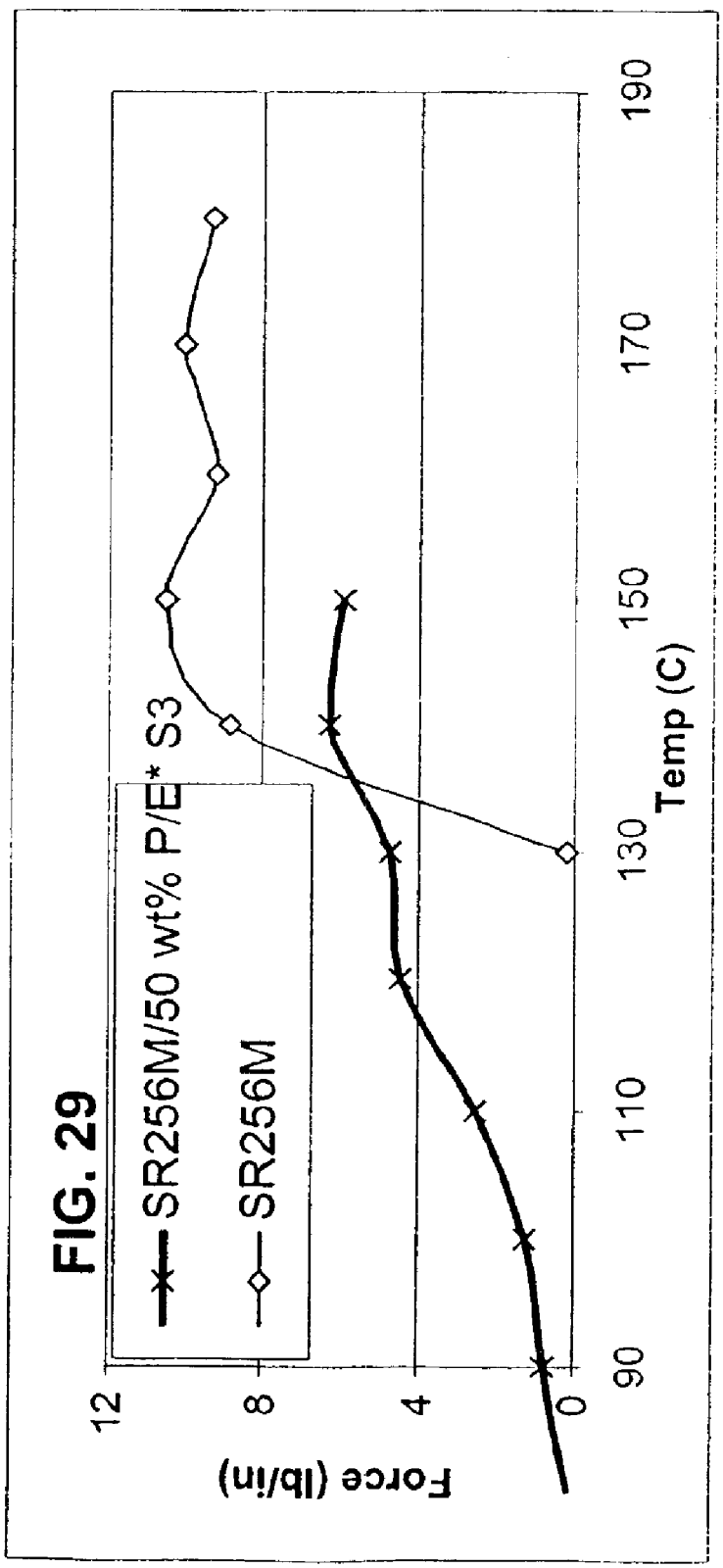
FIG. 29 shows the heat seal behavior for a blend of a P/E* copolymer with a random propylene-ethylene copolymer.
Figure 30:
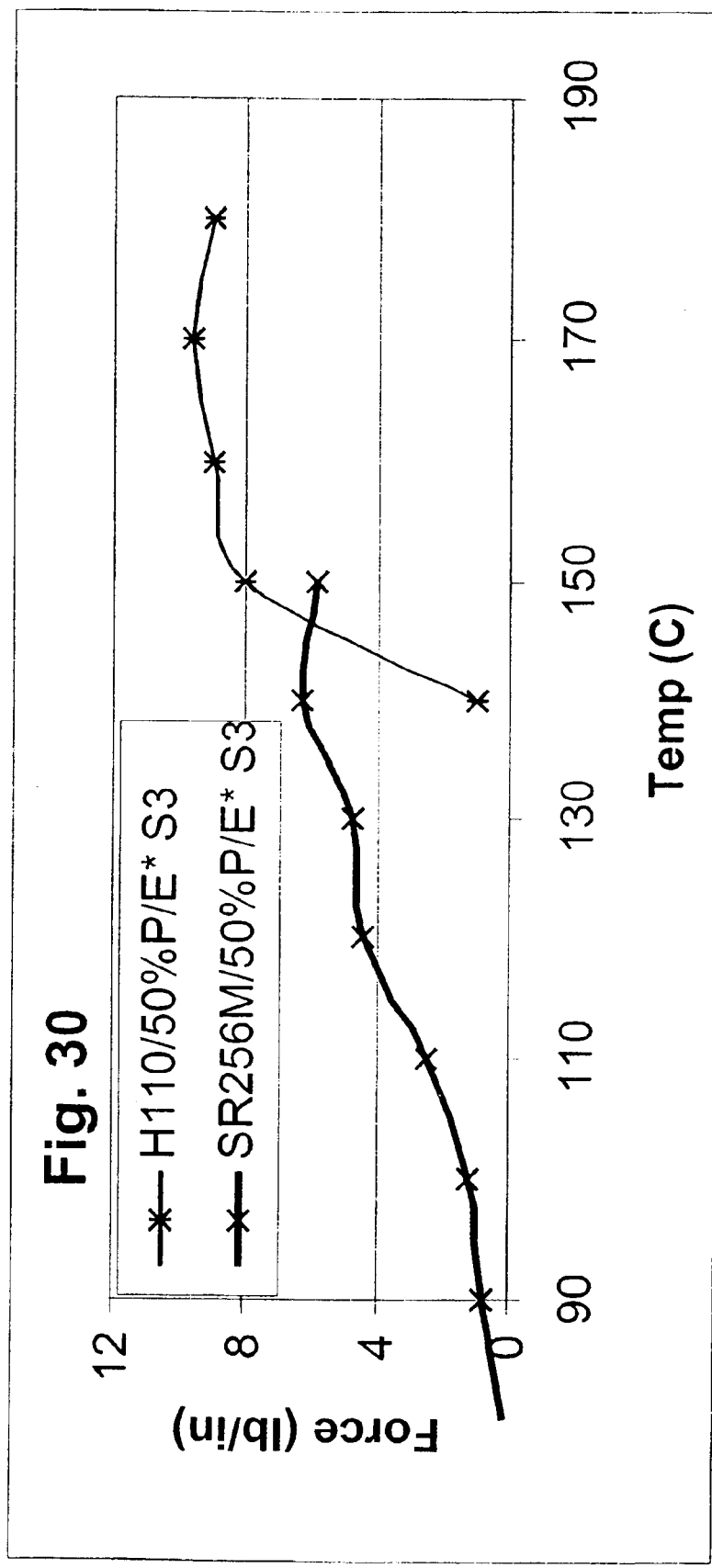
FIG. 30 compares the heat seal behavior of a blend of a P/E* copolymer with a random propylene-ethylene copolymer with the heat seal behavior of a blend of a P/E* copolymer with mini-random propylene-ethylene copolymer.

Now referring to FIGS. 29 and 30, it can be seen that blends of P/E* copolymers with random propylene-ethylene copolymers having greater than 1 wt % units derived from ethylene have greatly reduced seal initiation temperatures as compared to the random propylene-ethylene copolymer and as compared to a blend of a mini-random propylene-ethylene copolymer with P/E* copolymers.

Figure 31:
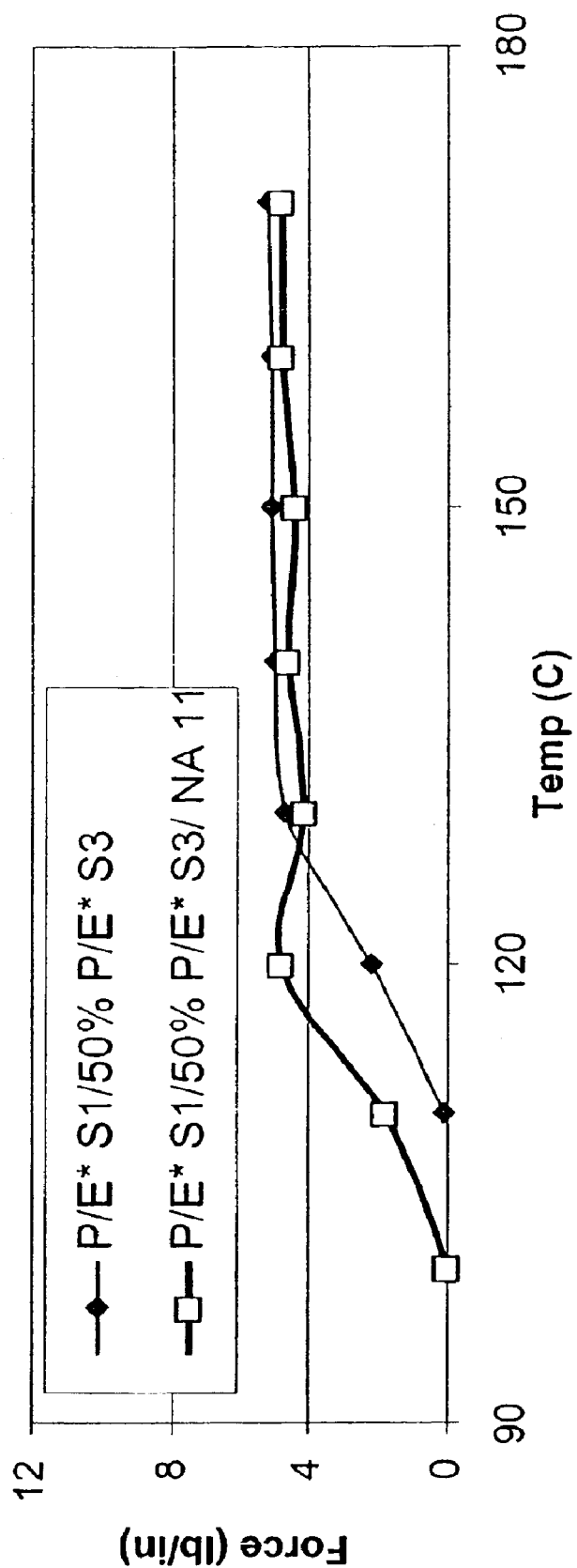
FIG. 31 shows the heat seal behavior for a blend of P/E* copolymer with and without an added nucleating agent.

FIG. 31 shows that nucleating agents, for example NA-11, are preferably added to blends of two or more P/E* copolymers to improve the heat seal behavior of such blends. Primarily such nucleating agents lower the seal initiation temperature while maintaining the seal strength.

Figure 32:
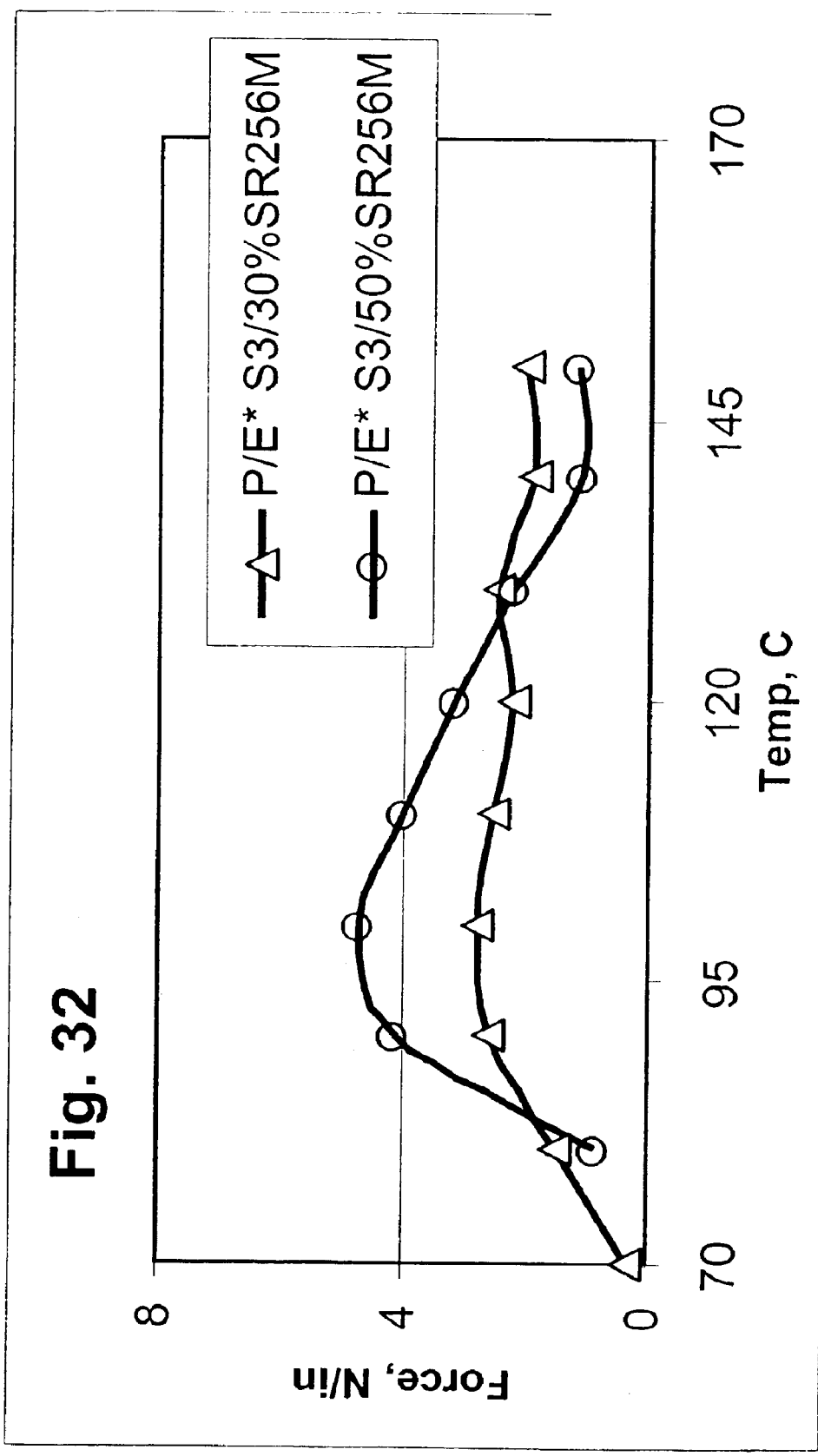
FIG. 32 shows the hot tack behavior of blends of P/E* copolymers with a random propylene-ethylene copolymer.

FIG. 32 shows that as the blends of P/E* copolymers having a weight percent of units derived from ethylene of from 5.5 to 6.5 wt % have very good hot tack performance.

FIGS. 32 and 33 show that blends of P/E* copolymers with mini-random propylene-ethylene copolymers have very good hot tack performance at higher temperatures, but worse hot tack performance at lower temperatures, as compared with random propylene-ethylene copolymers having greater than 2% by weight of units derived from ethylene.

EXAMPLE 18

Films made in accordance with the description of Example 13 were tested for oxygen permeability (O$_2$ Permeability) and water vapor transmission rate (WVTR). The O$_2$ permeability was measured in accordance with ASTM D3985-81 at an O$_2$ concentration of 1% at 1 atmosphere and 23° C. The WVTR was measured in accordance with ASTM F1249-90 at 37.8° C. The results are shown in Table 18.

As can be seen from Table 18, the P/E* polymers of the instant invention have a relatively higher WVTR and O$_2$ permeability than a comparative Z-N-catalyzed propylene-ethylene copolymer having equivalent ethylene levels. The enhanced permeability is particularly beneficial for film applications that take advantage of higher O$_2$ permeability and WVTR, such as fresh produce overwrap.

TABLE 18

| P/E* Ethylene % wt | O$_2$ permeability cc - Mil/100 in$^2$ × day @ 23° C. | WVTR gm - Mil/100 in$^2$ × day @ 37.8 C. |
| --- | --- | --- |
| 0% | — | 0.76 |
| 5 | 394 | 1.9 |
| 8 | 707 | 2.68 |

EXAMPLE 19

It is believed that the P/E* polymers will have lower shrink initiation temperatures than comparable Ziegler-Natta (Z-N) catalyzed propylene-ethylene copolymers having an equivalent amount of units derived from ethylene. In addition to the other physical properties listed for the P/E* polymers, this will lead to shrink films that are operable at a lower temperature. For example, this can be advantageous for food packaging preparation procedures. The shrink initiation temperature for this application is defined as the temperature that results in at least 20% shrinkage in either the cross-direction (CD) or machine direction (MD), as determined in accordance with ASTM 2732.

The good compatibility of the P/E* polymers with polyolefins (in particular polyethylenes) and the P/E* polymers excellent optical properties (as compared with typical Z-N-catalyzed polypropylenes) results in advantaged blends of P/E* polymers with polyolefins for shrink film applications. In particular, blends of P/E* polymers with low density polyethylene (LDPE) will provide shrink films having a better balance of optical and shrink properties compared to blends of LDPE with comparative Z-N-catalyzed propylene-ethylene copolymers.

Further, the same advantages set forth above will apply to multi-layer structures (such as multi-layer film structures) where the P/E* polymer and the polyolefin are not blended together, but are contained in adjacent layers of the multi-layer structure.

Although the invention has been described in considerable detail, this detail is for the purpose of illustration. Many variations and modifications can be made on the invention as described above without departing from the spirit and scope of the invention as described in the appended claims. All publications identified above, specifically including all U.S. patents and allowed U.S. patent applications, are incorporated in their entirety herein by reference.

What is claimed is:

1. A film comprising a first layer, the first layer having a machine direction tear of at least about 75 g/mil and comprising a first polymer, the first polymer comprising:
   (A) at least about 50 weight percent propylene, and
   (B) at least about 5 weight percent of at least one of ethylene and an unsaturated comonomer.

2. The film of claim 1 in which (B) component of the first polymer is at least one of ethylene, 1-butene, 4-methyl-1-pentene, 1-hexene, 1-heptene and 1-octene.

3. The film of claim 1 in which (B) component of the first polymer comprises ethylene.

4. The film of claim 1 in which the first layer has at least one of a haze value of less than about 10 percent, a 45 degree gloss of greater than about 60, and a dart value of greater than about 100 g/mil.

5. The film of claim 1 in which the first polymer of the first layer comprises at least about 60 weight percent of units derived from propylene and at least about 5 weight percent of units derived from a comonomer selected from the group consisting of ethylene and an unsaturated monomer other than ethylene, the first polymer further characterized as having at least one of the following properties: (i) $^{13}$C NMR peaks corresponding to a regio-error at about 14.6 and about 1.57 ppm, the peaks of about equal intensity, (ii) a skewness index, $S_{ix}$, greater than about −1.20, and (iii) a DSC curve with a $T_{me}$ that remains essentially the same and a $T_{max}$ that shifts to the left as the amount of comonomer in the copolymer is increased.

6. The film of claim 5 in which the first layer has at least one of a machine direction tear value of greater than about 100 g/mil, a haze value of less than about 9, a 45 degree gloss of greater than about 65, and a dart value of greater than about 150 g/mil.

7. The film of claim 5 in which the first layer has at least one of a machine direction tear value of greater than about 125 g/mil, a haze value of less than about 8, a 45 degree gloss of greater than about 70, and a dart value of greater than about 300 g/mil.

8. The film of claim 5 in which the (B) component comprises less than about 20 weight percent of the first polymer.

9. The film of claim 5 in which the first layer comprises a blend of the first polymer and a second polymer, the first polymer comprising at least about 50 weight percent of the first layer.

10. The film of claim 9 in which the second polymer of the first layer comprises at least one of an α-olefin homopolymer or copolymer.

11. The film of claim 9 comprising a second layer.

12. The film of claim 11 in which the composition of the second layer is different than the composition of the first layer.

13. The film of claim 12 in which the second layer comprises an α-olefin homopolymer or copolymer.

14. The film of claim 1 having a heat seal initiation temperature of less than about 110 C, and a minimum hot tack strength of 1 N/in at 100 C.

15. The film of claim 14 further characterized as exhibiting no substantial diminution of heat seal initiation temperature, hot tack initiation temperature, haze value or coefficient of friction due to contact with a chilling roll, air knife, machine direction stretching roller or a corona treatment during manufacture.

16. A film comprising a first layer, the first layer having a dart value of greater than about 100 g/mil and comprising a first polymer, the first polymer comprising:

(A) at least about 50 weight percent propylene, and (B) at least about 5 weight percent of at least one of ethylene and an unsaturated comonomer.

17. The film of claim 16 in which the (B) component of the first polymer is at least one of ethylene, 1-butane, 4-methyl-1-pentene, 1-hexene, 1-heptene and 1-octane.

18. The film of claim 16 in which the (B) component of the first polymer comprises ethylene.

19. The film of claim 18 in which the first layer has at least one of a haze value of less than about 10 percent and a 45 degree gloss of greater than about 65.

20. The film of claim 5 in which the polymer is further characterized as having an x-ray diffraction pattern that exhibits more gamma-form crystals than a copolymer comparable in all respects except that it is prepared with a Ziegler-Natta catalyst.

* * * * *

UNITED STATES PATENT AND TRADEMARK OFFICE
CERTIFICATE OF CORRECTION

PATENT NO. : 6,946,535 B2 Page 1 of 1
DATED : September 20, 2005
INVENTOR(S) : Li-Min Tau et al.

It is certified that error appears in the above-identified patent and that said Letters Patent is hereby corrected as shown below:

<u>Column 74,</u>
Line 56, replace "1.57" with -- 15.7 --.

Signed and Sealed this

Thirteenth Day of December, 2005

JON W. DUDAS
*Director of the United States Patent and Trademark Office*